US009132126B2

(12) United States Patent
Kim et al.

(10) Patent No.: US 9,132,126 B2
(45) Date of Patent: Sep. 15, 2015

(54) PHENYL-ISOXAZOLE DERIVATIVES AND PREPARATION PROCESS THEREOF

(75) Inventors: Dong Yeon Kim, Seoul (KR); Dae Jin Cho, Seoul (KR); Gong Yeal Lee, Seoul (KR); Hong Youb Kim, Seoul (KR); Seok Hun Woo, Gyeonggi-do (KR); Hae Un Lee, Gyeonggi-do (KR); Sung Moo Kim, Gyeonggi-do (KR); Choong Am Ahn, Gyeonggi-do (KR); Seung Bin Yoon, Seoul (KR)

(73) Assignee: IL-YANG PHARM. CO., LTD., Yongin-si (KR)

( * ) Notice: Subject to any disclaimer, the term of this patent is extended or adjusted under 35 U.S.C. 154(b) by 0 days.

(21) Appl. No.: 13/979,743

(22) PCT Filed: Mar. 30, 2012

(86) PCT No.: PCT/KR2012/002362
§ 371 (c)(1),
(2), (4) Date: Oct. 15, 2013

(87) PCT Pub. No.: WO2012/144752
PCT Pub. Date: Oct. 26, 2012

(65) Prior Publication Data
US 2014/0031364 A1    Jan. 30, 2014

(30) Foreign Application Priority Data
Apr. 19, 2011 (KR) .................. 10-2011-0036172

(51) Int. Cl.
| C07D 261/14 | (2006.01) |
| C07D 261/18 | (2006.01) |
| C07D 413/06 | (2006.01) |
| A61K 31/496 | (2006.01) |
| C07D 261/08 | (2006.01) |
| A61K 31/42 | (2006.01) |
| A61K 31/454 | (2006.01) |
| A61K 45/06 | (2006.01) |

(52) U.S. Cl.
CPC .............. *A61K 31/496* (2013.01); *A61K 31/42* (2013.01); *A61K 31/454* (2013.01); *A61K 45/06* (2013.01); *C07D 261/08* (2013.01); *C07D 261/18* (2013.01); *C07D 413/06* (2013.01)

(58) Field of Classification Search
None
See application file for complete search history.

(56) References Cited

U.S. PATENT DOCUMENTS

| 5,360,817 | A | 11/1994 | Von Itzstein et al. ......... 514/459 |
| 5,952,375 | A | 9/1999 | Bischofberger et al. ...... 514/459 |
| 6,699,871 | B2 | 3/2004 | Edmondson et al. ......... 514/249 |
| 6,809,204 | B2 | 10/2004 | Reddy et al. .................. 548/240 |
| 7,501,424 | B2 | 3/2009 | Kim et al. ................. 514/255.05 |
| 7,595,323 | B2 | 9/2009 | Kim et al. ................. 514/255.05 |
| 2004/0097734 | A1 | 5/2004 | Gerlach et al. ................ 544/323 |
| 2004/0248918 | A1 | 12/2004 | Kim et al. ................. 514/255.05 |
| 2008/0096899 | A1 | 4/2008 | Kim et al. ................. 514/255.05 |
| 2009/0163545 | A1 | 6/2009 | Goldfarb ....................... 514/312 |
| 2009/0192326 | A1 | 7/2009 | Perlman et al. .................. 560/37 |
| 2010/0297079 | A1* | 11/2010 | Almond et al. .............. 424/85.7 |
| 2010/0317856 | A1 | 12/2010 | Arjunan ........................ 544/350 |
| 2011/0071302 | A1 | 3/2011 | Kim et al. .................. 548/306.1 |
| 2012/0238539 | A1 | 9/2012 | Cianci et al. ............... 514/210.2 |
| 2012/0245176 | A1 | 9/2012 | Cianci et al. .................. 514/249 |

FOREIGN PATENT DOCUMENTS

| CA | 2812935 | 4/2012 |
| JP | A 2005-538968 | 12/2005 |
| JP | A 2011-507910 | 3/2011 |
| JP | A 2013-537193 | 9/2013 |
| JP | A 2013-542201 | 9/2013 |
| WO | WO 91/16320 | 10/1991 |
| WO | WO 96/26933 | 9/1996 |
| WO | WO 2004/002965 | 1/2004 |
| WO | WO 2005/051935 | 6/2005 |
| WO | WO 2007/008541 | 1/2007 |
| WO | WO 2008/011453 | 1/2008 |
| WO | WO 2010/018895 | 2/2010 |
| WO | WO 2011/015037 | 2/2011 |
| WO | WO 2011/041462 | 4/2011 |
| WO | WO 2013/147414 | 10/2013 |

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Vippagunta et al Advanced Drug Delivery Reviews, vol. 48, pp. 3-26 (2001).*
CA Registry No. 332174-85-3, entered into CA Registry File on Apr. 24, 2001, supplied by AsInEx.*
ASINEX Libraries, 1 page retrieved from the Internet at http://www.asinex.com/Libraries.html on Aug. 18, 2014.*
CA Registry No. 850471-96-4, entered into CA Registry File on May 16, 2005, supplied by Enamine.*
Enamine Product guide, 2 pages retrieved from the Internet at http://www.enamine.net/index.php?option=com_content&task=view &id=22 on Apr. 13, 2015.*
Letter/Written Disclosure of the Information Disclosure Statement for the above-referenced application, mailed on Oct. 2, 2013, 2 pages.
Su et al. "High-throughput identification of compounds targeting influenza RNA-dependent RNA polymerase activity," Proc. Natl. Acad. Sci. 107:19151-19156 (2010).
International Search Report, issued Sep. 24, 2012, in connection with International Patent Application No. PCT/KR2012/002362, 4 pages.
Letter/Written Disclosure of the Information Disclosure Statement for the above-referenced application, submitted on Feb. 25, 2015, 2 pages.

(Continued)

*Primary Examiner* — Emily Bernhardt
(74) *Attorney, Agent, or Firm* — Dentons US LLP; Stephanie Seidman; Frank J. Miskiel

(57) ABSTRACT

Disclosed are a phenyl-isoxazol derivative compound, which is useful as a treatment material for virus infection, especially, infection of an influenza virus, or its pharmaceutically acceptable derivative, a preparation method thereof, and an illness treatment pharmaceutical composition including the compound as an active ingredient.

2 Claims, No Drawings

(56) References Cited

OTHER PUBLICATIONS

Belshe et al., "Genetic basis of resistance to rimantadine emerging during treatment of influenza virus infection," J Virology 62(5): 1508-1512 (1988).

Chadha et al., "Characterization of solvatomorphs of methotrexate using thermoanalytical and other techniques," Acta Pharm. 59: 245-257 (2009).

de Jong et al., "Oseltamivir resistance during treatment of influenza A (H5N1) infection," N Eng J Med 353:2667-2672 (2005).

Giron, D., "Investigations of polymorphism and pseudo-polymorphism in pharmaceuticals by combined thermoanalytical techniques," J Thermal Analysis and Calorimetry 64:37-60 (2001).

Gubareva et al, "Influenza virus neuraminidase inhibitors," The Lancet 355:827-835 (2000).

Gubareva, "Molecular mechanisms of influenza virus resistance to neuraminidase inhibitors," Virus Research 103:199-203 (2004).

Hayden et al., "Use of the oral neuraminidase inhibitor oseltamivir in experimental human influenza: randomized controlled trials for prevention and treatment," JAMA 282(13):1240-1246 (1999).

Ives et al., "The H274Y mutation in the influenza A/H1N1 neuraminidase active site following oseltamivir phosphate treatment leave virus severely compromised both in vitro and in vivo," Antiviral Research 55: 307-317 (2002).

Kao et al., "Identification of influenza A nucleoprotein as an antiviral target," Nature Biotechnology 28(6):600-605 (2010).

Manek, R. and W. Kolling, "Influence of moisture on the crystal forms of niclosamide obtained from acetone and ethyl acetate," AAPS PharmSciTech. 5(1):Article 14, 8 pages (2004).

Morris et al., "Theoretical approaches to physical transformations of active pharmaceutical ingredients during manufacturing processes," Advanced Drug Delivery Reviews 48:91-114 (2001).

Palese et al., "Inhibition of influenza virus replication in tissue culture by 2-deoxy-2,3-dehydro-N-trifluoroacetylneuraminic acid (FANA): Mechanism of action," J. Gen. Virol. 33: 159-163 (1976).

Regoes et al., "Emergence of drug-resistant influenza virus: population dynamical considerations," Science 312:389-391 (2006).

Seifee et al., "Drug Polymorphism: A Review," Int J Health Res 2(4): 292-306 (2009).

International Preliminary Report on Patentability, issued Oct. 22, 2013, in connection with International Patent Application No. PCT/KR2012/002362, 5 pages.

Extended European Search Report, issued Aug. 5, 2014, in connection with corresponding European Patent Application No. 12 774 858.0, 7 pages.

Examiner's Report, issued Aug. 5, 2014, in connection with corresponding Canadian Patent Application No. 2,824,757, 3 pages.

Office Action, issued Aug. 15, 2014, and translation, in connection with corresponding Colombian Patent Application No. 13-169001-4, 24 pages.

Office Action, issued Oct. 7, 2014, and translation, in connection with corresponding Japanese Patent Application No. 2013-551922, 24 pages.

Response to Extended European Search Report, submitted Feb. 19, 2015, in connection with corresponding European Patent Application No. 12774858.0, 31 pages.

Examination Report, issued Feb. 20, 2015, in connection with Australian Patent Application No. 2011246914, 3 pages.

\* cited by examiner

PHENYL-ISOXAZOLE DERIVATIVES AND PREPARATION PROCESS THEREOF

RELATED APPLICATIONS

This application is the National Stage of International Application. No. PCT/KR2012/002362, filed 30 Mar. 2012, which claims benefit of priority to Korean Patent Application No. 10-2011-0036172, filed 19 Apr. 2011, the specification of which is incorporated by reference herein.

TECHNICAL FIELD

The present invention relates to a novel phenyl-isoxazol derivative having antiviral activity against an influenza virus and other similar viruses, which is useful in treatment and prevention of virus infection. Also, the present invention relates to a method using a compound for treating or preventing infection of an influenza virus and other similar viruses, a composition including the compound, a preparation method of the compound, and a synthesis intermediate used for the preparation method.

BACKGROUND ART

An influenza virus causes infectious acute febrile respiratory illness in a host. When the influenza virus is epidemic, it can easily spread across borders due to its strong infectiousness. Also, it may be unpredictably variously mutated, thereby causing interspecific infection. Thus, it is necessary to provide worldwide common countermeasures and monitoring systems.

An influenza virus is taxonomically defined as a member of Orthomyxovirus, and has three types of A, B, and C. Especially, A, and B types are epidemically spread. Type A influenza has a high mutatability, and zoonotically infects birds, pigs, and horses, as well as humans. Furthermore, the type A influenza includes various subtypes according to a combination of surface antigens (HA and NA). Unlike type A influenza, type B influenza causes relatively light symptoms, and infects humans and seals. Especially, in humans, it mainly causes an illness in children. Type C influenza can infect humans and pigs, but is known to have relatively low pathogenicity to humans. On the surface of these viruses, two kinds of surface antigens (that is, glycoproteins of Hemagglutinin (HA) and Neuraminidase (NA)) exist. Also, within the viruses, 8 fragmented RNAs exist. Hemagglutinin has a trimer structure including a head and a stem. The head region is related to most antigen mutations, which attaches the virus to a host cell by binding to a terminal sialic acid residue on the surface of the host cell, and sequentially allows the virus to penetrate the host cell. Neuraminidase is a mushroom-shaped tetramer with a head and a stem. On the surface of the head, an active region exists, which cleaves the alpha-ketosidic bond linking a terminal neuraminic acid residue to the oligosaccharide moiety on the cell surface. This cleavage performs an important role when a replicated and propagated virus within the infected cell comes out from the host cell and penetrates a respiratory organ mucous membrane cell. Surface antigens of a virus are mutated in the same subtype, and a new antigen mutant strain appears annually. Especially, from among influenza viruses, an avian influenza virus that has been problematic recently, infects various kinds of birds such as chickens, turkeys, ducks and wild birds through antigenic shift and quickly spreads. When chickens are infected with the virus, the morality rate is 80% or more. Thus, it is a virus causing serious damage and threatening the poultry farming industry worldwide. Further, it is reported that its ripple effect is not limited to the poultry farming industry. In other words, the virus may spread to humans by infecting a human body. Accordingly, research on the treatment of a virus may include inhibition of adsorption into an epithelial cell, inhibition of penetration into a cell, inhibition of transcription and replication of a gene, inhibition of protein synthesis, inhibition of release from a cell, and the like. Each of these is an objective of development of a novel antiviral drug.

TABLE 0

STRUCTURE 1. Amantadine

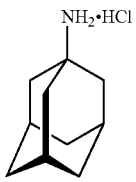

STRUCTURE 2. Rimantadine

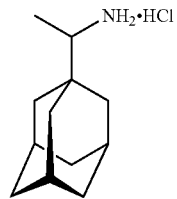

STRUCTURE 3. Oseltamivir Phosphate

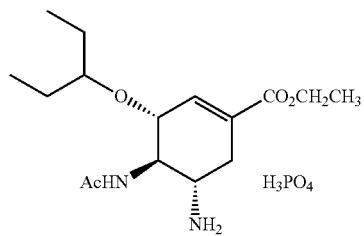

STRUCTURE 4. Zanamivir

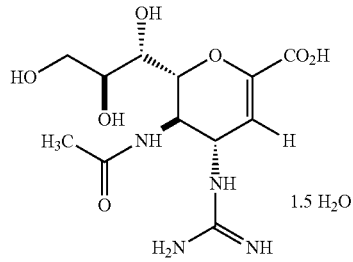 [SMILES: CC(=O)N[C@H]1[C@H]([C@@H](O)[C@@H](O)CO)OC(C(=O)O)=C[C@@H]1NC(=N)N]

Conventionally developed representative therapeutic agents for treating an influenza virus include 4 materials such as Amantadine, Rimantadine, Zanamivir, and Oseltamivir, which were approved by the US Food and Drug Administration (FDA) (see STRUCTURES 1 to 4). Amantadine or Rimantadine is an M2 ion channel blocker having activity only against a Hemagglutinin virus strain (an influenza virus), and interrupts replication of a virus particle introduced into a host cell. These drugs are effective in only type A influenza virus A. Also, since they have been used for 40 years, it is known that a virus resistant to the drugs has been generated, and the drugs cause serious side effects in the nervous system and the stomach. Meanwhile, Oseltamivir (Korean Patent Publication No. 10-1998-0703600) or Zanamivir (Korean Registered Patent 0169496) is a Neuraminidase inhibitor having activity only against a Neuraminidase virus strain (influenza virus) and interrupts a replicated virus from escaping from a host cell. The two kinds of therapeutic agents intervene in one process of influenza virus infection and interrupt the process, thereby inhibiting of the propagation of a virus. However, Zanamivir has a high antiviral effect, but has disadvantages such as a low bioavailability and a quick release from the kidney. Also, in Oseltamivir, there have been reported some side effects such as generation of a resistant virus, and serious emesis symptoms.

Following these drugs used as antiviral therapeutic agents, mutant viruses having serious side effects, tolerance, and strong resistance have rapidly appeared recently. Thus, their application requires great care. Also, in the development of a vaccine, there is a problem in that when an epidemic virus type does not correspond to a virus of the vaccine, the effect is insignificant. Accordingly, it is highly required to develop an improved drug that has a high effect in treatment and prevention of influenza infection, and has a high stability.

DISCLOSURE OF INVENTION

Technical Problem

Through research, the inventors of the present invention invented, as a better antiviral agent than a conventional agent, a novel phenyl-isoxazol compound having a high influenza virus inhibiting activity, and a high preventive effect of virus replication, which can treat or prevent an illness caused by an influenza virus.

The present invention has been made to solve the above mentioned disadvantages. As a result, the inventors found a compound represented by Formula 1, which has a different novel structure from a conventionally developed compound structure. Then, based on the finding, they completed this invention.

Solution to Problem

In accordance with an aspect of the present invention, there is provided a phenyl-isoxazol derivative represented by Formula 1 below, or its pharmaceutically acceptable salt, hydrate, solvate, prodrug, or composite.

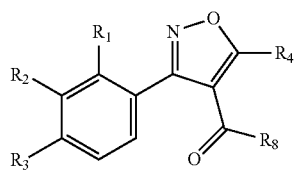

Formula 1

In Formula above, $R_1$, $R_2$ and $R_3$ each independently represents hydrogen, lower alkyl optionally substituted with halogen, lower alkoxy optionally substituted with halogen, or halogen, $R_4$ represents methyl or amine, and $R_8$ may be substituted with a radical of Formula 2 below, or substituted with a radical of Formula 3 below,

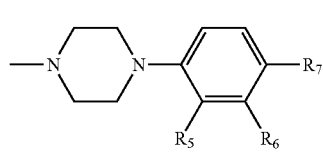

Formula 2

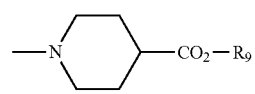

Formula 3 wherein, $R_5$, $R_6$ and $R_7$ each independently represents hydrogen, lower alkyl optionally substituted with halogen, hydroxy, lower alkoxy or halogen, and $R_9$ represents lower alkyl.

In accordance with another aspect of the present invention, there is provided a composition including the inventive compound, or its pharmaceutically acceptable salt, hydrate, solvate, prodrug, or composite, and a pharmaceutically acceptable carrier or excipient.

In accordance with a further aspect of the present invention, there is provided a pharmaceutical composition for treating or preventing virus infection, the composition includes the inventive compound, or its pharmaceutically acceptable salt, hydrate, solvate, prodrug, or composite, and a pharmaceutically acceptable carrier or excipient.

In accordance with a still further aspect of the present invention, there is provided the use of the preventive compound, or its pharmaceutically acceptable salt, hydrate, solvate, prodrug, or composite, for preparing a pharmaceutical composition for treatment or prevention of virus infection.

In accordance with a still yet further aspect of the present invention, there is provided a method for preventing or treating virus infection, the method including the step of administering a therapeutically effective amount of the inventive compound, or its pharmaceutically acceptable salt, hydrate, solvate, prodrug, or composite, to mammals, including humans, requiring virus infection treatment or prevention.

Mode for the Invention

Hereinafter, the present invention will be described in detail.

An influenza virus infection caused by an influenza virus is an illness frequently lethal to humans and animals. The influenza virus causes an infectious acute febrile respiratory organ illness in a host. When the influenza virus is epidemic, it can easily spread across borders due to its strong infectiousness. Also, it may be unpredictably variously mutated, thereby causing interspecific infection. Thus, it is necessary to provide worldwide common countermeasures and monitoring systems.

However, unlike an antifungal agent, etc. there exist only limited kinds of drugs applicable to influenza. For example, at present, representative therapeutic agents that have been recently used as Neuraminidase inhibitors include Oseltamivir and Zanamivir. These therapeutic agents perform a role of inhibiting the propagation of an influenza virus. However, Zanamivir has a high antiviral effect but has disadvantages such as a low bioavailability and a quick release from a kidney. Also, in Oseltamivir, there have been reported some side effects such as generation of a resistant virus, and serious emesis symptoms.

The inventors of the present invention found a compound represented by Formula 1 below, that is, a phenyl-isoxazol derivative, which has a higher antiviral activity against an influenza virus, and a higher susceptibility to a virus replication inhibitor inhibiting virus replication than its corresponding Oseltamivir phosphate.

Accordingly, the present invention provides a compound represented by Formula 1 below, and its pharmaceutically acceptable derivative.

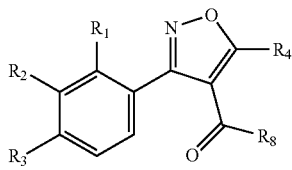

Formula 1

In Formula 1, $R_1$, $R_2$, $R_3$, $R_4$ and $R_8$ are the same as defined above.

In the present invention, it is understood that "a compound represented by Formula 1" (or "the inventive compound"), as long as not explicitly stated otherwise, includes its hydrate, solvate, pharmaceutically acceptable salt, prodrug, composite, and pharmaceutically acceptable derivative including diastereomer or enantiomer.

In the present invention, the term "lower alkyl" indicates a straight-chain or branched saturated aliphatic hydrocarbon radical that preferably includes 1 to 12 carbon atoms, alternatively 1 to 8 carbon atoms, or alternatively 1 to 6 carbon atoms. Examples of the alkyl radical may include methyl, ethyl, n-propyl, isopropyl, n-butyl, isobutyl, secondary-butyl, tertiary-butyl, pentyl, isoamyl, n-hexyl, and the like, but the present invention is not limited thereto. In the present invention, an alkyl group may be optionally substituted.

Also, the term "alkoxy" indicates oxygen added with an alkyl substituent. In the present invention, an alkoxy group may be optionally substituted.

Also, the term "lower halo alkyl" indicates a straight-chain or branched saturated aliphatic radical that preferably includes 1 to 12 carbon atoms, alternatively 1 to 8 carbon atoms, or alternatively 1 to 6 carbon atoms, in which hydrogen is substituted with halogen.

Also, the term "halogen" indicates an atom of fluoro, chlorine, bromine or iodine, and preferably indicates fluoro or chlorine. In the present invention, a halogen group may be optionally substituted.

The inventive compound also includes a salt within the scope of the present invention. It is understood that the inventive compound, e.g., the compound represented by Formula 1, as long as not explicitly stated otherwise, includes its salt.

In this specification, the term "salt" indicates an acidic and/or basic salt formed from inorganic and/or organic acid and base. The salt of the inventive compound may be, for example, formed by reacting the inventive compound with an acid or a base in the same amount as that of the compound in a medium or aqueous medium capable of precipitating the salt.

Non-limiting examples of the salt may include the following salts. The compound may be reacted with acetic acid, adipic acid, benzenesulfonic acid, benzoic acid, camphoric acid, camphorsulfonic acid, citric acid, cyclamate, ethane-1, 2-disulphonic acid, ethanesulfonic acid, 2-hydroxy ethanesulfonic acid, formic acid, fumaric acid, bromic acid, hydrochloric acid, sulfuric acid, nitric acid, phosphoric acid, malic acid, maleic acid, methanesulfonic acid, naphthalene-2-sulfonic acid, naphthalene-1,5-disulfonic acid, 1-hydroxy-2-naphthalate, nicotinic acid, trifluoroacetic acid, oxalic acid, p-toluene sulfonic acid, propionic acid, glycolic acid, succinic acid, tartaric acid, oxalic acid, amino acid (e.g., lysin), salicylic acid, 2,2-chloroacetic acid, L-aspartic acid, (+)-(1S)-camphor-10-sulfonic acid, 4-acetamido benzoic acid, caproic acid, cinnamic acid, gentistic acid, glutaric acid, malonic acid, mandelic acid, ortic acid, pamoate, aminosalicylic acid or the like to form an acid addition salt. When a lot of basic groups exist, a mono or poly acid addition salt may be formed.

Also, the compound represented by Formula 1 has ethylester as a functional group, and thus may form a carboxyl group. Under an acidic or basic condition, for example, at pH 11-12 (with a base such as sodium hydroxide, potassium hydroxide, sodium carbonate, sodium hydrogen carbonate, or ammonium hydroxide) or at pH 2-3 (with an acid such as hydrochloric acid or sulfuric acid), ethylester of the compound represented by Formula 1 may be hydrolyzed. The hydrolyzed compound represented by Formula 1 includes a carboxyl group, thereby forming a cation and a salt. There is no specific limitation in the kind of such a salt, as long as it is pharmaceutically acceptable. Examples of such a salt may include an alkaline metal salt, such as sodium, potassium and lithium salt an alkaline earth metal salt, such as calcium and magnesium salt other metal salts, such as aluminum, iron, zinc, copper nickel, and cobalt salt other inorganic salts, such as ammonium salt an amine salt, such as t-octylamine, dibenzylamine, morpholin, glucosamine, phenylglycine alkyl ester, ethylenediamine, methylglucamine, guanidine, diethylamine, triethylamine, dicyclohexylamine, N,N-dibenzylethylenediamine, chloroprocaine, procaine, diethaneolamine, benzylphenethylamine, piperazine, tetraethylammonium and tris(hydroxymethyl)aminomethane salt.

In this specification, the term "pharmaceutically acceptable derivative" indicates the inventive compounds hydrate, solvate, pharmaceutically acceptable salt, prodrug, or composite, which maintains the required biological activity of the compound and does not show an unwanted toxicological effect.

The present invention also includes a prodrug of the inventive compound. The term "prodrug" indicates a compound covalently bonded to a carrier. The prodrug may release an active ingredient while being administered to a mammal subject. The release of the active ingredient may occur within a living body, and the prodrug may be prepared by technologies known to a person skilled in the art. In such technologies, in a certain compound, an appropriate functional group is modified. However, the modified functional group regenerates an original functional group through a general operation or within a living body. Non-limiting examples of the prodrug include ester (e.g., acetate, formate, and benzoate derivative) and the like.

The inventive compound has an inhibiting activity against a strain of an influenza virus, and is highly effective in the treatment and the prevention of infection of influenza having susceptibility to a virus replication inhibitor inhibiting virus replication, and other similar viruses.

According to an embodiment of the present invention, in the compound represented by Formula 1, preferably, when the radical in Formula 2 is substituted for $R_8$, two from among $R_1$, $R_2$ and $R_3$ represent hydrogen, the remaining one represents lower alkyl optionally substituted with halogen, lower alkoxy optionally substituted with halogen, or halogen, preferably fluoro or chlorine. $R_4$ represents methyl, or amine, and from among $R_5$, $R_6$ and $R_7$, one or two each independently represents hydrogen, lower alkyl optionally substituted with halogen, hydroxy, lower alkoxy, or halogen or $R_1$ represents halogen, preferably chlorine, $R_4$ represents methyl or amine, $R_2$, $R_3$, $R_5$, and $R_7$ each represents hydrogen, and $R_6$ represents alkoxy, preferably methoxy. When the radical in Formula 3 is substituted for $R_8$, two from among $R_1$, $R_2$ and $R_3$ represent hydrogen, the remaining one represents lower alkyl optionally substituted with halogen, lower alkoxy optionally substituted with halogen, or halogen, $R_4$ represents amine, and $R_9$ represents lower alkyl.

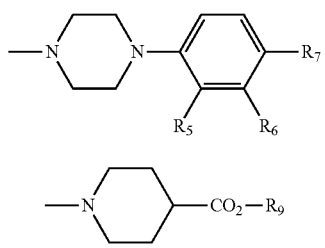

Formula 2

Formula 3

In another embodiment of the present invention, in the compound represented by Formula 1, more preferably, when the radical of Formula 2 is substituted for $R_8$, two from among $R_1$, $R_2$ and $R_3$ represent hydrogen, the other one represents trifluoromethyl, fluoro, or trifluoromethoxy, $R_4$ represents methyl or amine, from among $R_5$, $R_6$ and $R_7$, one or two each independently represents hydrogen, methoxy, chlorine, fluoro, trifluoromethyl or hydroxy; or $R_1$ represents halogen, preferably chlorine, $R_4$ represents methyl or amine, $R_2$, $R_3$, $R_5$, and $R_7$ each represents hydrogen, and $R_6$ represents alkoxy, preferably methoxy. When the radical of Formula 3 is substituted for $R_8$, $R_4$ represents amine, two from among $R_1$, $R_2$ and $R_3$ represent hydrogen, the remaining one represents trifluoromethyl, fluoro, or trifluoromethoxy, and $R_9$ represents methyl or ethyl. In view of inhibition of influenza virus, especially, when the radical of Formula 2 is substituted for $R_8$, $R_1$ represents trifluoromethyl, or trifluoromethoxy, $R_2$ and $R_3$ represent hydrogen, $R_4$ represents methyl, and from among $R_5$, $R_6$ and $R_7$, one or two each independently represents hydrogen, hydroxy, methoxy, or chlorine $R_1$ represents chlorine, $R_4$ represents methyl, $R_2$, $R_3$, $R_5$ and $R_7$ represent hydrogen, and $R_6$ represents methoxy or $R_2$ represents fluoro, trifluoromethyl, or trifluoromethoxy, $R_1$ and $R_3$ represent hydrogen, $R_4$ represents methyl or amine, and from among $R_5$, $R_6$ and $R_7$, one or two each independently represents hydrogen, hydroxy, methoxy, trifluoromethyl or chlorine. Meanwhile, when the radical of Formula 3 is substituted for $R_8$, $R_1$ represents trifluoromethoxy, $R_2$ and $R_3$ represent hydrogen, $R_4$ represents amine, and $R_9$ represents ethyl.

The inventive compound represented by Formula 1 may be prepared by the following synthesis process. The isomer and solvate (e.g., hydrate) of the compound represented by Formula 1 are also within the scope of the present invention. The solvation method is generally known in the art. Accordingly, the inventive compound may be used in the form of a pharmaceutically useful hydrate or salt, and obtained by the method described by Reaction Scheme below.

The inventive compound of Formula 1 is prepared by the steps of: reacting a compound represented by Formula 4 below preferably with hydroxylammoniumchloride in the presence of a base to produce a compound represented by Formula 5 below chlorinating the compound represented by Formula 5 so as to produce a compound represented by Formula 6 below cyclizing the compound represented by Formula 6 so as to produce a compound represented by Formula 7 below as an isoxazol compound removing $R_{10}$ as a protecting group of Formula 7 so as to produce a compound represented by Formula 8 and reacting the compound represented by Formula 8 with a compound represented by Formula 2 or Formula 3 so as to produce a compound represented by Formula 9a or Formula 9b.

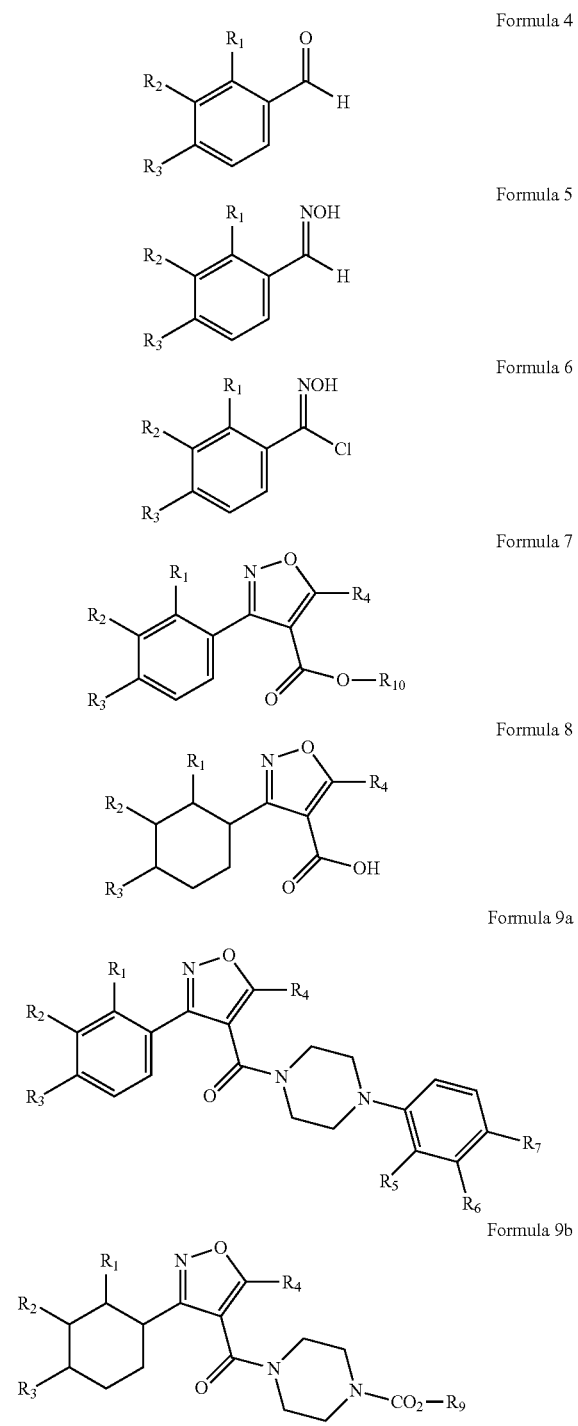

In Formulas above,
$R_1$ to $R_9$ are the same as defined above, and
$R_{10}$ represents lower alkyl, preferably methyl, ethyl or isopropyl group.

Reaction scheme 1

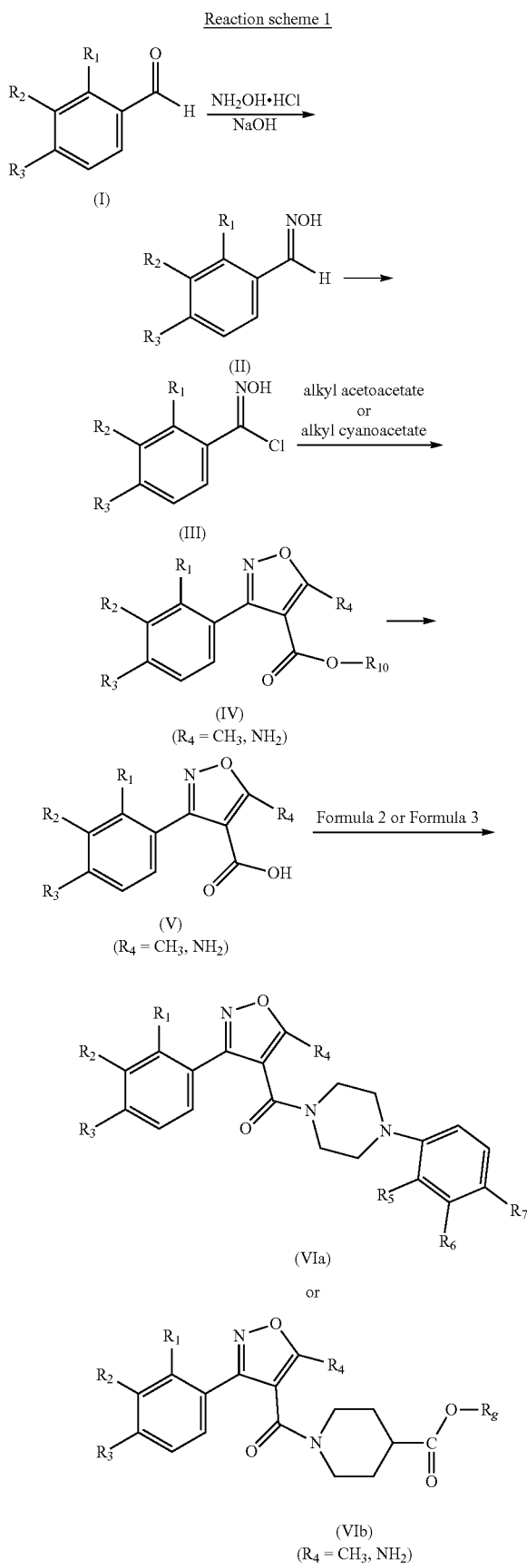

In Reaction scheme 1 above, $R_1$ to $R_{10}$ are the same as defined above.

A phenylaldehyde compound (I) having $R_1$, $R_2$ and $R_3$ substituted onto a benzene ring was commercially available. The phenylaldehyde compound (I) is reacted with hydroxylammoniumchloride or its equivalent in the presence of a base so as to synthesize a compound of benzaldehyde oxime (II). Then, through a chlorination reaction, a benzimidoyl chloride compound (III) is produced. An isoxazol compound (V) in which R is substituted with methyl or amine may be obtained through a generally used synthesis method (cyclization reaction) by using alkyl acetoacetate or alkyl cyanoacetate. From a phenyl-isoxazol derivative compound (V, $R_4$=methyl) or a compound (V, $R_4$=amine) including a carboxyl group and an amine group, a phenyl-isoxazol derivative compound (VIa or VIb) is produced by using 1-ethyl-3-(3'-dimethylaminopropyl)carbodiimidehydrochloride (EDCl) or hydroxybenzotriazol (HOBt) in the presence of a base.

The inventive preparation method may be carried out preferably in a solvent in the presence of a base or an acid. Herein, there is no specific limitation in a solvent, an acid, and a base as long as they have no adverse effect on the reaction. For example, the solvent may be at least one kind selected from the group consisting of tetrahydrofuran, methylenechloride, ethanol, N,N-dimethylformamide, N,N-dimethylacetamide, ethyllacetate, tert-butanol, toluene, and dioxane. The base may be at least one kind selected from the group consisting of pyridine, triethylamine, diethylamine, sodium carbonate, potassium carbonate, sodium hydroxide, potassium hydroxide, sodium hydride, sodium methoxide, sodium ethoxide, sodium tert-butoxide, potassium tert-butoxide, lithium aluminum hydride, lithium borohydride, and sodium nitrate, and cesium carbonate. The acid may be at least one kind selected from the group consisting of trifluoroacetic acid, hydrochloric acid, nitric acid, sulfuric acid, bromic acid, and acetic acid.

Starting materials used in the preparation of the inventive compounds according to the method are commercially available, or can be easily bought. The reaction may be generally carried out under a cooling or heating condition. After the reaction, through a general after-treatment process, such as column chromatography, recrystallization, etc. a final compound may be purified.

Meanwhile, the present invention is related to a pharmaceutical composition for treating or preventing virus infection, in which the compound represented by Formula 1, or its pharmaceutically acceptable derivative is administered in an effective amount to mammals, including humans. Especially, the composition is effective in inhibiting influenza infection, and thus may be effectively used in the treatment of such an illness.

When the inventive compounds determined to be effective in inhibiting the illness is administered, a single dose or a multiple dose generally ranges from 0.01 to 750 mg/kg per day, preferably ranges from 0.1 to 100 mg, and most preferably ranges from 0.5 to 25 mg. However, the specific dose for an individual patient may vary according to a specific compound, a patient's weight, sex, diet, a drug administration time, an administration method, a release ratio, a drug mixing ratio, a patient's state, age, etc.

The inventive compound may be administered without being processed in the treatment. However, the active ingredient is preferably provided as a pharmaceutical formulation.

Accordingly, the present invention provides a pharmaceutical formulation obtained by mixing a compound represented by Formula 1 or its pharmaceutically acceptable derivative with a pharmaceutically acceptable carrier and/or excipient.

Also, the inventive compound may be administered via any suitable route. However, preferably, the compound is administered by injection or in oral form.

An injection preparation, for example, a sterile injection aqueous or oily suspension, may be prepared by using an appropriate material such as a dispersant, a wetting agent or a suspension according to a known art. As a solvent, water, ringer's solution or isotonic NaCl solution may be used. Also, sterile fixed oil is also generally used as a solvent or a suspension medium. For this, any nonirritating fixed oil, including monoglyceride or di-glyceride, may be used. Also, fatty acid such as oleic acid may used in injection preparation.

A solid administration form for oral administration may include capsule, tablet, pill, powder and granule forms. Especially, capsule and tablet forms are preferred. Preferably, tablet and pill forms are prepared as intestinal drugs. The solid administration form may be prepared by mixing the inventive active compound represented by Formula 1 with at least one inert diluent (such as sucrose, lactose, starch), a lubricant (such as magnesium stearate), and a carrier (such as a disintegrating agent, a binding agent, etc.).

The inventive compound has an inhibiting activity against a strain of an influenza virus, and may be used to treat and prevent infection of influenza having susceptibility to a Neuraminidase inhibitor or a virus replication inhibitor inhibiting virus replication, and other similar viruses. Herein, it may be used in combination with a secondary therapeutic agent having an activity against the same virus. This compound, for example, may be used in combination with Zanamivir, Oseltamivir, Amantadine, Rimantadine or the like. The administration amount of each compound may be the same or different, compared to the administration amount of the compound alone.

Hereinafter, the present invention will be described in more detail with reference to Preparation Examples and Examples. However, Preparation Examples and Examples, as described below, are illustrative only, and do not limit the present invention.

PREPARATION EXAMPLE 1

Synthesis of 2-(trifluoromethyl)benzaldehydeoxime 2-(trifluoromethyl)benzaldehyde (34.82 g, 200.0 mmol) was dissolved in ethanol (200 mL), and added with sodium hydroxide (12.00 g, 300.0 mmol) dissolved in purified water (50 mL). Hydrochloric acid hydroxylamine (16.68 g, 240 mmol) dissolved in purified water (50 mL) was added thereto, followed by stirring for 3 hours. After the reaction was completed, the resultant product was added with ice. The produced solid was filtered, washed with purified water (600 mL), and dried so as to provide a white solid required compound (32.15 g, 171 mmol, 85%).

$^1$H-NMR (400 MHz, CDCl$_3$, δ)=7.23 (dd, 1H), 7.59 (dd, 1H), 7.76 (m, 2H), 8.39 (s, 1H), 11.63 (s, 1H)

PREPARATION EXAMPLE 2

Synthesis of 2-chlorobenzaldehydeoxime

In a similar manner as described in Preparation Example 1, by using 2-chlorobenzaldehyde (29.14 g, 200.0 mmol), sodium hydroxide (12.00 g, 300.0 mmol) and hydrochloric acid hydroxylamine (16.68 g, 240 mmol), a white solid required compound (29.73 g, 189 mmol, 95%) was obtained.

$^1$H-NMR (400 MHz, CDCl$_3$, δ)=7.37 (m, 2H), 7.48 (dd, 1H), 7.82 (dd, 1H), 8.37 (s, 1H), 11.28 (s, 1H)

PREPARATION EXAMPLE 3

Synthesis of 3-fluorobenzaldehydeoxime

In a similar manner as described in Preparation Example 1, by using 3-fluorobenzaldehyde (24.82 g, 200.0 mmol), sodium hydroxide (12.00 g, 300.0 mmol) and hydrochloric acid hydroxylamine (16.68 g, 240 mmol), a white solid required compound (22.48 g, 162 mmol, 81%) was obtained.

$^1$H-NMR (400 MHz, CDCl$_3$, δ)=7.32 (m, 1H), 7.56 (m, 3H), 8.20 (s, 1H)

PREPARATION EXAMPLE 4

Synthesis of 2-fluorobenzaldehydeoxime

In a similar manner as described in Preparation Example 1, by using 2-fluorobenzaldehyde (24.82 g, 200.0 mmol), sodium hydroxide (12.00 g, 300.0 mmol) and hydrochloric acid hydroxylamine (16.68 g, 240 mmol), a white solid required compound (25.96 g, 186 mmol, 93%) was obtained.

$^1$H-NMR (400 MHz, CDCl$_3$, δ)=7.22 (m, 1H), 7.45 (m, 1H), 7.65 (m, 2H), 8.15 (s, 1H)

PREPARATION EXAMPLE 5

Synthesis of 4-(trifluoromethoxy)benzaldehydeoxime

In a similar manner as described in Preparation Example 1, by using 4-(trifluoromethoxy)benzaldehyde (38.02 g, 200.0 mmol), sodium hydroxide (12.00 g, 300.0 mmol) and hydrochloric acid hydroxylamine (16.68 g, 240 mmol), a white solid required compound (38.68 g, 188 mmol, 94%) was obtained.

$^1$H-NMR (400 MHz, CDCl$_3$, δ)=7.38 (d, 2H), 7.72 (tt, 2H), 8.20 (s, 1H), 11.43 (s, 1H)

PREPARATION EXAMPLE 6

Synthesis of 2-(trifluoromethoxy)benzaldehydeoxime

In a similar manner as described in Preparation Example 1, by using 2-(trifluoromethoxy)benzaldehyde (38.03 g, 200.0 mmol), sodium hydroxide (12.00 g, 300.0 mmol) and hydrochloric acid hydroxylamine (16.6 g, 240 mmol), a white solid required compound (38.67 g, 188 mmol, 94%) was obtained.

$^1$H-NMR (400 MHz, CDCl$_3$, δ)=7.43 (m, 2H), 7.54 (m, 1H), 7.89 (m, 1H), 8.24 (s, 1H), 11.76 (s, 1H)

PREPARATION EXAMPLE 7

Synthesis of 3-(trifluoromethyl)benzaldehydeoxime

In a similar manner as described in Preparation Example 1, by using 3-(trifluoromethyl)benzaldehyde (34.82 g, 200.0 mmol), sodium hydroxide (12.00 g, 300.0 mmol) and hydrochloric acid hydroxylamine (16.68 g, 240 mmol), a white solid required compound (35.33 g, 187 mmol, 93%) was obtained.

$^1$H-NMR (400 MHz, CDCl$_3$, δ)=7.33 (m, 1H), 7.72 (m, 3H), 8.44 (s, 1H), 11.62 (s, 1H)

PREPARATION EXAMPLE 8

Synthesis of 3-(trifluoromethoxy)benzaldehydeoxime

In a similar manner as described in Preparation Example 1, by using 3-(trifluoromethoxy)benzaldehyde (38.03 g, 200.0 mmol), sodium hydroxide (12.00 g, 300.0 mmol) and hydrochloric acid hydroxylamine (16.6 g, 240 mmol), a white solid required compound (39.74 g, 193 mmol, 97%) was obtained.
$^1$H-NMR (400 MHz, CDCl$_3$, δ)=7.53 (m, 1H), 7.69 (m, 3H), 8.31 (s, 1H), 11.71 (s, 1H)

PREPARATION EXAMPLE 9

Synthesis of N-hydroxy-2-(trifluoromethyl)benzimidoylchloride 2-(trifluoromethyl)benzaldehydeoxime (30.0 g, 158.60 mmol) was dissolved in dimethylformimide (300 mL), and added with N-chlorosuccinimide (23.31 g, 174.46 mmol), followed by stirring for 15 hours. After the reaction was completed, the resultant solution was vacuum evaporated, added with ethylacetate (1,500 mL), washed with saturated sodium chloride aqueous solution (1,000 mL) and purified water (1,000 mL), respectively, dried with anhydrous sodium sulfate, and vacuum-evaporated to provide a pale yellow solid required compound (32.81 g, 146.70 mmol, 93%).
$^1$H-NMR (400 MHz, CDCl$_3$, δ)=7.73 (m, 2H), 7.80 (t, 1H), 7.86 (d, 1H), 12.61 (s, 1H)

PREPARATION EXAMPLE 10

Synthesis of 2-chloro-N-hydroxybenzimidoylchloride

In a similar manner as described in Preparation Example 9, by using dimethylformamide (240 mL), 2-chlorobenzaldehydeoxime (19.97 g, 128.32 mmol) and N-chlorosuccinimide (18.85 g, 141.14 mmol), a pale yellow solid required compound (20.04 g, 105.21 mmol, 82%) was obtained.
$^1$H-NMR (400 MHz, CDCl$_3$, δ)=7.46 (m, 1H), 7.54 (m, 1H), 7.58 (m, 2H), 12.54 (s, 1H)

PREPARATION EXAMPLE 11

Synthesis of 3-fluoro-N-hydroxybenzimidoylchloride

In a similar manner as described in Preparation Example 9, by using dimethylformamide (240 mL), 3-fluorobenzaldehydeoxime (20.0 g, 143.77 mmol) and N-chlorosuccinimide (21.12 g, 158.12 mmol), a pale yellow solid required compound (22.52 g, 129.79 mmol, 90%) was obtained.
$^1$H-NMR (400 MHz, CDCl$_3$, δ)=7.37 (m, 1H), 7.60 (m, 3H)

PREPARATION EXAMPLE 12

Synthesis of 2-fluoro-N-hydroxybenzimidoylchloride

In a similar manner as described in Preparation Example 9, by using dimethylformamide (240 mL), 2-fluorobenzaldehydeoxime (20.0 g, 143.76 mmol) and N-chlorosuccinimide (21.12 g, 158.12 mmol), a pale yellow solid required compound (23.32 g, 134.40 mmol, 94%) was obtained.
$^1$H-NMR (400 MHz, CDCl$_3$, δ)=7.29 (m, 1H), 7.47 (m, 1H), 7.62 (m, 2H)

PREPARATION EXAMPLE 13

Synthesis of N-hydroxy-4-(trifluoromethoxy)benzimidoylchloride

In a similar manner as described in Preparation Example 9, by using dimethylformamide (240 mL), 4-(trifluoromethoxy) benzaldehydeoxime (20.0 g, 97.51 mmol) and N-chlorosuccinimide (14.31 g, 107.26 mmol), a pale yellow solid required compound (21.10 g, 88.04 mmol, 90%) was obtained.
$^1$H-NMR (400 MHz, CDCl$_3$, δ)=7.47 (dd, 1H), 7.72 (tt, 2H), 12.60 (s, 1H)

PREPARATION EXAMPLE 14

Synthesis of N-hydroxy-2-(trifluoromethoxy)benzimidoylchloride

In a similar manner as described in Preparation Example 9, by using dimethylformamide (240 mL), 4-(trifluoromethoxy) benzaldehydeoxime (20.0 g, 97.50 mmol) and N-chlorosuccinimide (14.32 g, 107.26 mmol), a pale yellow solid required compound (19.48 g, 81.30 mmol, 83%) was obtained.
$^1$H-NMR (400 MHz, CDCl$_3$, δ)=7.49 (m, 1H), 7.62 (m, 1H), 7.68 (dd, 1H), 12.67 (s, 1H)

PREPARATION EXAMPLE 15

Synthesis of N-hydroxy-3-(trifluoromethyl)benzimidoylchloride

In a similar manner as described in Preparation Example 9, by using 3-(trifluoromethyl)benzaldehydeoxime (30.0 g, 158.60 mmol), dimethylformimide (300 mL) and N-chlorosuccinimide (23.31 g, 174.46 mmol), a pale yellow solid required compound (33.81 g, 151.22 mmol, 95%) was obtained.
$^1$H-NMR (400 MHz, CDCl$_3$, δ)=7.79 (m, 3H), 7.83 (m, 1H), 12.64 (s, 1H)

PREPARATION EXAMPLE 16

Synthesis of N-hydroxy-3-(trifluoromethoxy)benzimidoylchloride

In a similar manner as described in Preparation Example 9, by using dimethylformamide (240 mL), 3-(trifluoromethoxy) benzaldehydeoxime (20.0 g, 97.50 mmol) and N-chlorosuccinimide (14.32 g, 107.26 mmol), a pale yellow solid required compound (19.43 g, 81.10 mmol, 82%) was obtained.
$^1$H-NMR (400 MHz, CDCl$_3$, δ)=7.56 (m, 1H), 7.64 (m, 3H), 12.61 (s, 1H)

PREPARATION EXAMPLE 17

Synthesis of methyl-5-methyl-3-(2-(trifluoromethyl) phenyl)isoxazol-4-carboxylate N-hydroxy-2-(trifluoromethyl)benzimidoylchloride (8.0 g, 35.78 mmol) and methyllacetoacetate (8.30 g, 71.56 mmol) were dissolved in methanol (160 mL). The resultant solution was stirred for 30 minutes while the reactor was cooled to −10° C. Then, sodium methoxide (5.80 g, 107.34 mmol) was slowly added thereto. The resultant product was warmed up to room temperature, stirred for 3 hours, and vacuum-evaporated to remove methanol. Then, ethylacetate (200 mL) was added thereto. The resultant product was washed with purified water (200 mL) and saturated sodium chloride aqueous solution (200 mL), respectively, dried with anhydrous sodium sulfate, and vacuum-evaporated. Through column chromatography, a purified white solid required compound (5.79 g, 20.31 mmol, 57%) was obtained.

$^1$H-NMR (400 MHz, CDCl$_3$, δ)=2.75 (s, 3H), 3.58 (s, 3H), 7.56 (m, 1H), 7.78 (m, 1H), 7.90 (m, 1H)

PREPARATION EXAMPLE 18

Synthesis of methyl-3-(2-chlorophenyl)-5-methyl-isoxazol-4-carboxylate

In a similar manner as described in Preparation Example 17, by using methanol (160 mL), 2-chloro-N-hydroxybenzimidoylchloride (8.0 g, 42.10 mmol), methylacetoacetate (9.78 g, 84.20 mmol) and sodium methoxide (6.83 g, 126.30 mmol), a white solid required compound (6.32 g, 25.11 mmol, 60%) was obtained.

$^1$H-NMR (400 MHz, CDCl$_3$, δ)=2.59 (s, 3H), 3.86 (s, 3H), 7.62 (m, 3H)

PREPARATION EXAMPLE 19

Synthesis of methyl-3-(3-fluorophenyl)-5-methyl-isoxazol-4-carboxylate

In a similar manner as described in Preparation Example 17, by using methanol (160 mL), 3-fluoro-N-hydroxybenzimidoyl chloride (8.00 g, 46.09 mmol), methylacetoacetate (10.07 g, 92.18 mmol) and sodium methoxide (7.47 g, 138.27 mmol), a white solid required compound (7.60 g, 32.14 mmol, 70%) was obtained.

$^1$H-NMR (400 MHz, CDCl$_3$, δ)=2.58 (s, 3H), 3.91 (s, 3H), 7.21 (m, 1H), 7.42 (m, 3H)

PREPARATION EXAMPLE 20

Synthesis of methyl-3-(2-fluorophenyl)-5-methyl-isoxazol-4-carboxylate

In a similar manner as described in Preparation Example 17, by using methanol (160 mL), 2-fluoro-N-hydroxybenzimidoyl chloride (8.00 g, 46.09 mmol), methylacetoacetate (10.07 g, 92.18 mmol) and sodium methoxide (7.47 g, 138.27 mmol), a white solid required compound (7.84 g, 33.33 mmol, 72%) was obtained.

$^1$H-NMR (400 MHz, CDCl$_3$, δ)=2.59 (s, 3H), 3.92 (s, 3H), 7.22 (m, 1H), 7.43 (m, 1H), 7.55 (m, 2H)

PREPARATION EXAMPLE 21

Synthesis of methyl-5-methyl-3-(4-(trifluoromethoxy)phenyl)isoxazol-4-carboxylate In a similar manner as described in Preparation Example 17, by using methanol (160 mL), N-hydroxy-4-(trifluoromethoxy)benzimidoylchloride (8.00 g, 33.39 mmol), methylacetoacetate (7.76 g, 66.78 mmol) and sodium methoxide (5.41 g, 100.17 mmol), a white solid required compound (6.74 g, 22.36 mmol, 67%) was obtained.

$^1$H-NMR (400 MHz, CDCl$_3$, δ)=2.71 (s, 3H), 3.73 (s, 3H), 7.48 (d, 2H), 7.76 (d, 2H)

PREPARATION EXAMPLE 22

Synthesis of methyl-5-methyl-3-(2-(trifluoromethoxy)phenyl)isoxazol-4-carboxylate In a similar manner as described in Preparation Example 17, by using methanol (160 mL), N-hydroxy-4-(trifluoromethoxy)benzimidoylchloride (8.00 g, 33.39 mmol), methylacetoacetate (7.76 g, 66.78 mmol) and sodium methoxide (5.41 g, 100.17 mmol), a white solid required compound (7.04 g, 23.37 mmol, 70%) was obtained.

$^1$H-NMR (400 MHz, CDCl$_3$, δ)=2.73 (s, 3H), 3.64 (s, 3H), 7.53 (m, 1H), 7.61 (m, 1H), 7.69 (m, 1H)

PREPARATION EXAMPLE 23

Synthesis of methyl-5-methyl-3-(3-(trifluoromethyl)phenyl)isoxazol-4-carboxylate In a similar manner as described in Preparation Example 17, by using methanol (160 mL), N-hydroxy-3-(trifluoromethyl)benzimidoylchloride (8.0 g, 35.78 mmol), methylacetoacetate (8.30 g, 71.56 mmol) and sodium methoxide (5.80 g, 107.34 mmol), a white solid required compound (5.82 g, 20.41 mmol, 57%) was obtained.

$^1$H-NMR (400 MHz, CDCl$_3$, δ)=2.73 (s, 3H), 3.56 (s, 3H), 7.58 (m, 1H), 7.97 (m, 3H)

PREPARATION EXAMPLE 24

Synthesis of methyl-5-methyl-3-(3-(trifluoromethoxy)phenyl)isoxazol-4-carboxylate In a similar manner as described in Preparation Example 17, by using methanol (160 mL), N-hydroxy-3-(trifluoromethoxy)benzimidoylchloride (8.00 g, 33.39 mmol), methylacetoacetate (7.76 g, 66.78 mmol) and sodium methoxide (5.41 g, 100.17 mmol), a white solid required compound (6.82 g, 22.64 mmol, 68%) was obtained.

$^1$H-NMR (400 MHz, CDCl$_3$, δ)=2.76 (s, 3H), 3.62 (s, 3H), 7.54 (m, 1H), 7.61 (m, 3H)

PREPARATION EXAMPLE 25

Synthesis of 5-methyl-3-(2-(trifluoromethyl)phenyl)isoxazol-4-carboxylic acid methyl 5-methyl-3-(2-(trifluoromethyl)phenyl)isoxazol-4-carboxylate (6.0 g, 21.03 mmol) was dissolved in methanol (60 mL), added with 3% sodium hydroxide aqueous solution (60 mL), stirred at 30° C. for 7 hours, and vacuum-evaporated so as to remove methanol. The remaining solution was washed with ethyl acetate (20 mL), and the aqueous layer was neutralized by a hydrochloric acid aqueous solution. Then, the produced crystal was filtered, washed with purified water (50 mL), and dried so as to provide a white solid required compound (5.48 g, 20.12 mmol, 96%).

$^1$H-NMR (400 MHz, DMSO, δ)=2.69 (s, 3H), 7.49 (m, 1H), 7.72 (m, 1H), 7.83 (m, 1H), 13.12 (brs, 1H)

PREPARATION EXAMPLE 26

Synthesis of 3-(2-chlorophenyl)-5-methylisoxazol-4-carboxylic acid

In a similar manner as described in Preparation Example 25, by using methanol (60 mL), methyl-3-(2-chlorophenyl)-

5-methylisoxazol-4-carboxylate (6.0 g, 23.84 mmol) and 3% sodium hydroxide aqueous solution (60 mL), a white solid required compound (5.10 g, 21.44 mmol, 90%) was obtained.
$^1$H-NMR (400 MHz, DMSO, δ)=2.75 (s, 3H), 7.46 (m, 2H), 7.53 (m, 1H), 7.59 (m, 1H), 13.00 (brs, 1H)

PREPARATION EXAMPLE 27

Synthesis of 3-(3-fluorophenyl)-5-methylisoxazol-4-carboxylic acid

In a similar manner as described in Preparation Example 25, by using methanol (60 mL), methyl-3-(3-fluorophenyl)-5-methylisoxazol-4-carboxylate (6.0 g, 25.51 mmol) and 3% sodium hydroxide aqueous solution (60 mL), a white solid required compound (5.51 g, 24.92 mmol, 98%) was obtained.
$^1$H-NMR (400 MHz, DMSO, δ)=2.58 (s, 3H), 7.21 (m, 1H), 7.42 (m, 3H), 13.04 (brs, 1H)

PREPARATION EXAMPLE 28

Synthesis of 3-(3-fluorophenyl)-5-methylisoxazol-4-carboxylic acid

In a similar manner as described in Preparation Example 25, by using methanol (60 mL), methyl-3-(3-fluorophenyl)-5-methylisoxazol-4-carboxylate (6.0 g, 25.51 mmol) and 3% sodium hydroxide aqueous solution (60 mL), a white solid required compound (5.21 g, 23.44 mmol, 92%) was obtained.
$^1$H-NMR (400 MHz, DMSO, δ)=2.60 (s, 3H), 7.21 (m, 1H), 7.43 (m, 1H), 7.54 (m, 2H)

PREPARATION EXAMPLE 29

Synthesis of 5-methyl-3-(4-(trifluoromethoxy)phenyl)isoxazol-4-carboxylic acid

In a similar manner as described in Preparation Example 25, by using methanol (60 mL), methyl-5-methyl-3-(4-(trifluoromethoxy)phenyl)isoxazol-4-carboxylate (6.0 g, 19.91 mmol) and 3% sodium hydroxide aqueous solution (60 mL), a white solid required compound (5.55 g, 19.32 mmol, 97%) was obtained.
$^1$H-NMR (400 MHz, DMSO, δ)=2.71 (s, 3H), 7.48 (d, 2H), 7.76 (d, 2H), 13.15 (brs, 1H)

PREPARATION EXAMPLE 30

Synthesis of 5-methyl-3-(2-(trifluoromethoxy)phenyl)isoxazol-4-carboxylic acid

In a similar manner as described in Preparation Example 25, by using methanol (60 mL), methyl-5-methyl-3-(2-(trifluoromethoxy)phenyl)isoxazol-4-carboxylate (6.0 g, 19.91 mmol) and 3% sodium hydroxide aqueous solution (60 mL), a white solid required compound (5.34 g, 18.59 mmol, 93%) was obtained.
$^1$H-NMR (400 MHz, DMSO, δ)=2.72 (s, 3H), 7.50 (m, 2H), 7.58 (m, 1H), 7.67 (m, 1H), 13.62 (brs, 1H)

PREPARATION EXAMPLE 31

Synthesis of 5-methyl-3-(3-(trifluoromethyl)phenyl)isoxazol-4-carboxylic acid

In a similar manner as described in Preparation Example 25, by using methanol (60 mL), methyl-5-methyl-3-(3-(trifluoromethyl)phenyl)isoxazol-4-carboxylate (6.0 g, 21.03 mmol) and 3% sodium hydroxide aqueous solution (60 mL), a white solid required compound (5.37 g, 19.80 mmol, 94%) was obtained.
$^1$H-NMR (400 MHz, DMSO, δ)=2.67 (s, 3H), 7.48 (m, 1H), 7.80 (m, 3H), 13.11 (brs, 1H)

PREPARATION EXAMPLE 32

Synthesis of 5-methyl-3-(3-(trifluoromethoxy)phenyl)isoxazol-4-carboxylic acid

In a similar manner as described in Preparation Example 25, by using methanol (60 mL), methyl-5-methyl-3-(3-(trifluoromethoxy)phenyl)isoxazol-4-carboxylate (6.0 g, 19.91 mmol) and 3% sodium hydroxide aqueous solution (60 mL), a white solid required compound (5.47 g, 19.04 mmol, 96%) was obtained.
$^1$H-NMR (400 MHz, DMSO, δ)=2.71 (s, 3H), 7.48 (m, 2H), 7.64 (m, 2H), 13.57 (brs, 1H)

PREPARATION EXAMPLE 33

Synthesis of methyl-5-amino-3-(2-(trifluoromethyl)phenyl)isoxazol-4-carboxylate

In a similar manner as described in Preparation Example 17, by using methanol (160 mL), N-hydroxy-2-(trifluoromethyl)benzimidoyl chloride (8.00 g, 33.39 mmol), methylcyanoacetate (4.14 g, 41.74 mmol) and sodium methoxide (3.61 g, 66.78 mmol), a white solid required compound (8.13 g, 28.42 mmol, 85%) was obtained.
$^1$H-NMR (400 MHz, DMSO, δ)=3.59 (s, 3H), 6.12 (brs, 2H), 7.36 (m, 1H), 7.57 (m, 2H), 7.69 (m, 1H)

PREPARATION EXAMPLE 34

Synthesis of methyl-5-amino-3-(2-chlorophenyl)isoxazol-4-carboxylate

In a similar manner as described in Preparation Example 17, by using methanol (160 mL), 2-chloro-N-hydroxybenzimidoylchloride (8.00 g, 42.10 mmol), methylcyanoacetate (5.22 g, 52.63 mmol) and sodium methoxide (4.55 g, 84.20 mmol), a white solid required compound (9.40 g, 37.21 mmol, 88%) was obtained.
$^1$H-NMR (400 MHz, DMSO, δ)=3.65 (s, 3H), 6.20 (brs, 2H), 7.41 (m, 4H)

PREPARATION EXAMPLE 35

Synthesis of methyl 5-amino-3-(3-fluorophenyl)isoxazol-4-carboxylate

In a similar manner as described in Preparation Example 17, by using methanol (160 mL), 3-fluoro-N-hydroxybenzimidoyl chloride (8.00 g, 46.09 mmol), methylcyanoacetate (5.94 g, 59.92 mmol) and sodium methoxide (4.98 g, 92.18 mmol), a white solid required compound (8.42 g, 35.64 mmol, 77%) was obtained.
$^1$H-NMR (400 MHz, CDCl$_3$, δ)=3.92 (s, 3H), 6.30 (brs, 2H), 7.21 (m, 1H), 7.42 (m, 3H)

PREPARATION EXAMPLE 36

Synthesis of methyl-5-amino-3-(2-fluorophenyl)isoxazol-4-carboxylate

In a similar manner as described in Preparation Example 17, by using methanol (160 mL), 2-fluoro-N-hydroxybenzimidoyl chloride (8.00 g, 46.09 mmol), methylcyanoacetate (5.94 g, 59.92 mmol) and sodium methoxide (4.98 g, 92.18 mmol), a white solid required compound (8.23 g, 34.82 mmol, 76%) was obtained.

$^1$H-NMR (400 MHz, CDCl$_3$, δ)=3.89 (s, 3H), 6.31 (brs, 2H), 7.22 (m, 1H), 7.41 (m, 1H), 7.55 (m, 2H)

PREPARATION EXAMPLE 37

Synthesis of methyl 5-amino-3-(4-(trifluoromethoxy)phenyl)isoxazol-4-carboxylate In a similar manner as described in Preparation Example 17, by using methanol (160 mL), N-hydroxy-4-(trifluoromethoxy)benzimidoylchloride (8.00 g, 33.39 mmol), methylcyanoacetate (4.31 g, 43.41 mmol) and sodium methoxide (3.61 g, 66.78 mmol), a white solid required compound (8.27 g, 27.35 mmol, 82%) was obtained.

$^1$H-NMR (400 MHz, DMSO, δ)=3.51 (s, 3H), 6.21 (brs, 2H), 7.26 (d, 2H), 7.77 (d, 2H)

PREPARATION EXAMPLE 38

Synthesis of methyl 5-amino-3-(2-(trifluoromethoxy)phenyl)isoxazol-4-carboxylate In a similar manner as described in Preparation Example 17, by using methanol (160 mL), N-hydroxy-2-(trifluoromethoxy)benzimidoylchloride (8.00 g, 33.39 mmol), methylcyanoacetate (4.31 g, 43.41 mmol) and sodium methoxide (3.61 g, 66.78 mmol), a white solid required compound (9.07 g, 30.02 mmol, 90%) was obtained.

$^1$H-NMR (400 MHz, DMSO, δ)=3.38 (s, 3H), 6.18 (brs, 2H), 7.41 (m, 2H), 7.42 (m, 1H), 7.47 (m, 1H)

PREPARATION EXAMPLE 39

Synthesis of methyl-5-amino-3-(3-(trifluoromethyl)phenyl)isoxazol-4-carboxylate

In a similar manner as described in Preparation Example 17, by using methanol (160 mL), N-hydroxy-3-(trifluoromethyl)benzimidoylchloride (8.00 g, 33.39 mmol), methylcyanoacetate (4.14 g, 41.74 mmol) and sodium methoxide (3.61 g, 66.78 mmol), a white solid required compound (7.46 g, 26.06 mmol, 78%) was obtained.

$^1$H-NMR (400 MHz, DMSO, δ)=3.61 (s, 3H), 6.11 (brs, 2H), 7.32 (m, 1H), 7.62 (m, 3H)

PREPARATION EXAMPLE 40

Synthesis of methyl-5-amino-3-(3-(trifluoromethoxy)phenyl)isoxazol-4-carboxylate In a similar manner as described in Preparation Example 17, by using methanol (160 mL), N-hydroxy-3-(trifluoromethoxy)benzimidoylchloride (8.00 g, 33.39 mmol), methylcyanoacetate (4.31 g, 43.41 mmol) and sodium methoxide (3.61 g, 66.78 mmol), a white solid required compound (8.42 g, 27.87 mmol, 83%) was obtained.

$^1$H-NMR (400 MHz, DMSO, δ)=3.42 (s, 3H), 6.22 (brs, 2H), 7.46 (m, 2H), 7.53 (m, 2H)

PREPARATION EXAMPLE 41

Synthesis of 5-amino-3-(2-(trifluoromethyl)phenyl)isoxazol-4-carboxylic acid

In a similar manner as described in Preparation Example 25, by using methanol (60 mL), 5-amino-3-(2-(trifluoromethyl)phenyl)isoxazol-4-carboxylate (6.0 g, 20.96 mmol) and 3% sodium hydroxide aqueous solution (60 mL), a white solid required compound (4.06 g, 14.92 mmol, 71%) was obtained.

$^1$H-NMR (400 MHz, DMSO, δ)=7.40 (m, 1H), 7.70 (m, 2H), 7.76 (m, 1H), 7.81 (brs, 2H), 12.18 (brs, 1H)

PREPARATION EXAMPLE 42

Synthesis of 5-amino-3-(2-chlorophenyl)isoxazol-4-carboxylic acid

In a similar manner as described in Preparation Example 25, by using methanol (60 mL), methyl-5-amino-3-(2-chlorophenyl)isoxazol-4-carboxylate (6.0 g, 23.75 mmol) and 3% sodium hydroxide aqueous solution (60 mL), a white solid required compound (3.66 g, 15.33 mmol, 65%) was obtained.

$^1$H-NMR (400 MHz, DMSO, δ)=7.45 (m, 3H), 7.54 (m, 1H), 7.85 (brs, 2H), 12.04 (brs, 1H)

PREPARATION EXAMPLE 43

Synthesis of 5-amino-3-(3-fluorophenyl)isoxazol-4-carboxylic acid

In a similar manner as described in Preparation Example 25, by using methanol (60 mL), methyl-5-amino-3-(3-fluorophenyl)isoxazol-4-carboxylate (6.0 g, 25.40 mmol) and 3% sodium hydroxide aqueous solution (60 mL), a white solid required compound (3.08 g, 13.86 mmol, 55%) was obtained.

$^1$H-NMR (400 MHz, DMSO, δ)=6.28 (brs, 2H), 7.20 (m, 1H), 7.44 (m, 3H)

PREPARATION EXAMPLE 44

Synthesis of 5-amino-3-(2-fluorophenyl)isoxazol-4-carboxylic acid

In a similar manner as described in Preparation Example 25, by using methanol (60 mL), methyl-5-amino-3-(2-fluorophenyl)isoxazol-4-carboxylate (6.0 g, 25.40 mmol) and 3% sodium hydroxide aqueous solution (60 mL), a white solid required compound (3.18 g, 14.33 mmol, 56%) was obtained.

$^1$H-NMR (400 MHz, DMSO, δ)=6.22 (brs, 2H), 7.25 (m, 1H), 7.45 (m, 1H), 7.59 (m, 2H), 12.13 (brs, 1H)

PREPARATION EXAMPLE 45

Synthesis of 5-amino-3-(4-(trifluoromethoxy)phenyl)isoxazol-4-carboxylic acid

In a similar manner as described in Preparation Example 25, by using methanol (60 mL), methyl-5-amino-3-(4-(trifluoromethoxy)phenyl)isoxazol-4-carboxylate (6.0 g, 19.85 mmol) and 3% sodium hydroxide aqueous solution (60 mL), a white solid required compound (4.32 g, 15.02 mmol, 76%) was obtained.

$^1$H-NMR (400 MHz, DMSO, δ)=7.31 (d, 2H), 7.83 (d, 2H), 7.85 (brs, 2H), 12.01 (brs, 1H)

PREPARATION EXAMPLE 46

Synthesis of 5-amino-3-(2-(trifluoromethoxy)phenyl)isoxazol-4-carboxylic acid

In a similar manner as described in Preparation Example 25, by using methanol (60 mL), methyl-5-amino-3-(2-(trifluoromethoxy)phenyl)isoxazol-4-carboxylate (6.0 g, 19.85 mmol) and 3% sodium hydroxide aqueous solution (60 mL), a white solid required compound (4.00 g, 13.89 mmol, 70%) was obtained.
$^1$H-NMR (400 MHz, DMSO, δ)=7.45 (m, 3H), 7.59 (m, 1H), 7.82 (brs, 2H), 12.04 (brs, 1H)

PREPARATION EXAMPLE 47

Synthesis of 5-amino-3-(3-(trifluoromethyl)phenyl) isoxazol-4-carboxylic acid

In a similar manner as described in Preparation Example 25, by using methanol (60 mL), 5-amino-3-(3-(trifluoromethyl)phenyl)isoxazol-4-carboxylate (6.0 g, 20.96 mmol) and 3% sodium hydroxide aqueous solution (60 mL), a white solid required compound (4.14 g, 15.21 mmol, 73%) was obtained.
$^1$H-NMR (400 MHz, DMSO, δ)=7.34 (m, 1H), 7.68 (m, 3H), 7.87 (brs, 2H), 12.31 (brs, 1H)

PREPARATION EXAMPLE 48

Synthesis of 5-amino-3-(3-(trifluoromethoxy)phenyl)isoxazol-4-carboxylic acid

In a similar manner as described in Preparation Example 25, by using methanol (60 mL), methyl 5-amino-3-(3-(trifluoromethoxy)phenyl)isoxazol-4-carboxylate (6.0 g, 19.85 mmol) and 3% sodium hydroxide aqueous solution (60 mL), a white solid required compound (4.16 g, 14.43 mmol, 73%) was obtained.
$^1$H-NMR (400 MHz, DMSO, δ)=7.43 (m, 3H), 7.63 (m, 1H), 7.84 (brs, 2H), 12.04 (brs, 1H)

EXAMPLE 1

Synthesis of (4-(2-fluorophenyl)piperazine-1-yl)(5-methyl-3-(2-(trifluoromethyl)phenyl)isoxazol-4-yl)methanone 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol) were dissolved in dichloromethane (30 mL), and stirred at room temperature for 8 hours. The resultant solution was washed with saturated sodium carbonate aqueous solution (30 mL), purified water (30 mL) and saturated sodium chloride aqueous solution (30 mL), respectively. Then, the organic layer was dried with anhydrous sodium sulfate, concentrated, and purified with column chromatography so as to provide a white solid required compound (528 mg, 1.34 mmol, 73%).
$^1$H-NMR (400 MHz, CDCl$_3$, δ)=2.56 (s, 3H), 2.73 (brs, 2H), 3.01 (brs, 2H), 3.41 (brs, 2H), 3.72 (brs, 2H), 6.04 (m, 3H), 6.81 (t, 1H), 7.49 (m, 1H), 7.72 (m, 1H), 7.83 (m, 1H)

EXAMPLE 2

Synthesis of (4-(3,4-dichlorophenyl)piperazine-1-yl)(5-methyl-3-(2-(trifluoromethyl)phenyl)isoxazol-4-yl)methanone In a similar manner as described in Example 1, by using dichloromethane (30 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (644 mg, 1.33 mmol, 72%) was obtained.
$^1$H-NMR (400 MHz, CDCl$_3$, δ)=2.58 (s, 3H), 2.75 (brs, 2H), 3.03 (brs, 2H), 3.42 (brs, 2H), 3.74 (brs, 2H), 6.69 (dd, 1H), 6.89 (d, 1H), 7.28 (m, 1H), 7.55 (d, 1H), 7.64 (m, 2H), 7.82 (d, 2H)

EXAMPLE 3

Synthesis of (4-(3-methoxyphenyl)piperazine-1-yl) (5-methyl-3-(2-(trifluoromethyl)phenyl)isoxazol-4-yl)methanone In a similar manner as described in Example 1, by using dichloromethane (30 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a gel-like required compound (602 mg, 1.35 mmol, 73%) was obtained.
$^1$H-NMR (400 MHz, CDCl$_3$, δ)=2.64 (brs, 2H), 2.67 (s, 3H), 3.13 (brs, 2H), 3.38 (brs, 2H), 4.06 (brs, 2H), 6.43 (brs, 1H), 6.53 (m, 2H), 7.39 (dd, 1H), 7.49 (m, 1H), 7.70 (m, 1H), 7.80 (dd, 1H), 7.81 (m, 1H)

EXAMPLE 4

Synthesis of (4-(2-methoxyphenyl)piperazine-1-yl) (5-methyl-3-(2-trifluoromethyl)phenyl)isoxazol-4-yl)methanone In a similar manner as described in Example 1, by using dichloromethane (30 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (504 mg, 1.13 mmol, 62%) was obtained.
$^1$H-NMR (400 MHz, CDCl$_3$, δ)=2.59 (S, 3H), 2.75 (brs, 2H), 3.06 (brs, 2H), 3.42 (brs, 2H), 3.76 (brs, 2H), 3.82 (s, 3H), 6.49 (brs, 1H), 6.49 (m, 2H), 7.19 (t, 1H), 7.55 (d, 1H), 7.67 (m, 2H), 7.82 (d, 1H)

EXAMPLE 5

Synthesis of (5-methyl-3-(2-(trifluoromethyl)phenyl) isoxazol-4-yl)(4-(3-(trifluoromethyl)phenyl)piperazine-1-yl)methanone In a similar manner as described in Example 1, by using dichloromethane (30 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a gel-like required compound (593 mg, 1.23 mmol, 67%) was obtained.
$^1$H-NMR (400 MHz, CDCl$_3$, δ)=2.63 (brs, 2H), 2.69 (s, 3H), 3.15 (brs, 2H), 3.37 (brs, 2H), 3.39 (brs, 2H), 4.02 (brs, 2H), 6.91 (m, 2H), 7.03 (m, 1H), 7.26 (m, 1H), 7.51 (m, 1H), 7.70 (m, 2H), 7.82 (m, 1H)

EXAMPLE 6

Synthesis of (4-(4-hydroxyphenyl)piperazine-1-yl) (5-methyl-3-(2-(trifluoromethyl)phenyl)isoxazol-4-yl)methanone In a similar manner as described in Example 1, by using dimethylformimide (15 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (467 mg, 1.08 mmol, 59%) was obtained.

$^1$H-NMR (400 MHz, CDCl$_3$, δ)=2.64 (brs, H), 2.69 (s, 3H), 3.91 (brs, 4H), 6.78 (m, 4H), 7.49 (m, 2H), 7.72 (m, 1H), 7.83 (m, 1H)

EXAMPLE 7

Synthesis of (4-(2-hydroxyphenyl)piperazine-1-yl)(5-methyl-3-(2-(trifluoromethyl)phenyl)isoxazol-4-yl)methanone In a similar manner as described in Example 1, by using dimethylformimide (15 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (451 mg, 1.05 mmol, 57%) was obtained.

$^1$H-NMR (400 MHz, CDCl$_3$, δ)=2.49 (brs, 2H), 2.61 (s, 3H), 2.78 (brs, 2H), 3.50 (brs, 2H), 3.80 (brs, 2H), 6.93 (m, 3H), 7.13 (m, 1H), 7.58 (m, 1H), 7.70 (m, 2H), 7.86 (m, 1H)

EXAMPLE 8

Synthesis of (4-(4-fluorophenyl)piperazine-1-yl)(5-methyl-3-(2-trifluoromethyl)phenyl)isoxazol-4-yl)methanone In a similar manner as described in Example 1, by using dichloromethane (30 mL), 5-methyl-3-(2-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (548 mg, 1.26 mmol, 69%) was obtained.

$^1$H-NMR (400 MHz, CDCl$_3$, δ)=2.68 (s, 3H), 2.91 (brs, 4H), 3.42 (brs, 4H), 6.91 (m, 2H), 7.05 (m, 2H), 7.45 (m, 1H), 7.71 (m, 1H), 7.82 (m, 1H)

EXAMPLE 9

Synthesis of (3-(2-chlorophenyl)-5-methylisoxazol-4-yl)(4-(3-methoxyphenyl)piperazine-1-yl)methanone In a similar manner as described in Example 1, by using dichloromethane (30 mL), 3-(2-chlorophenyl)-5-methylisoxazol-4-carboxylic acid (437 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (576 mg, 1.40 mmol, 76%) was obtained.

$^1$H-NMR (400 MHz, CDCl$_3$, δ)=2.61 (s, 3H), 3.10 (brs, 2H), 3.33 (brs, 2H), 3.74 (brs, 4H), 3.79 (s, 3H), 6.36 (t, 1H), 6.46 (m, 2H), 7.18 (t, 1H), 7.41 (m, 2H), 7.50 (m, 1H), 7.56 (dd, 1H)

EXAMPLE 10

Synthesis of (3-(3-fluorophenyl)-5-methylisoxazol-4-yl)(4-(2-fluorophenyl)piperazine-1-yl)methanone In a similar manner as described in Example 1, by using dichloromethane (30 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (562 mg, 1.41 mmol, 76%) was obtained.

$^1$H-NMR (400 MHz, CDCl$_3$, δ)=2.56 (s, 3H), 2.70 (brs, 2H), 3.14 (brs, 2H), 3.28 (brs, 2H), 3.96 (brs, 2H), 6.70 (m, 2H), 7.02 (m, 2H), 7.17 (m, 1H), 7.45 (m, 3H)

EXAMPLE 11

Synthesis of (4-(3,4-dichlorophenyl)piperazine-1-yl)(3-(3-fluorophenyl)-5-methylisoxazol-4-yl)methanone In a similar manner as described in Example 1, by using dichloromethane (30 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (619 mg, 1.43 mmol, 78%) was obtained.

$^1$H-NMR (CDCl$_3$, 400 MHz, 5)=2.56 (s, 3H), 2.66 (brs, 2H), 3.16 (brs, 2H), 3.27 (brs, 2H), 3.91 (brs, 2H), 6.67 (dd, 1H), 6.88 (d, 1H), 7.19 (m, 1H), 7.29 (m, 1H), 7.44 (m, 3H)

EXAMPLE 12

Synthesis of (3-(3-fluorophenyl)-5-methylisoxazol-4-yl)(4-(3-methoxyphenyl)piperazine-1-yl)methanone In a similar manner as described in Example 1, by using dichloromethane (30 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (612 mg, 1.55 mmol, 84%) was obtained.

$^1$H-NMR (400 MHz, CDCl$_3$, δ)=2.56 (s, 3H), 2.73 (brs, 2H), 3.19 (brs, 2H), 3.30 (brs, 2H), 3.80 (s, 3H), 3.93 (brs, 2H), 6.41 (m, 1H), 6.49 (m, 2H), 7.18 (m, 2H), 7.46 (m, 3H)

EXAMPLE 13

Synthesis of (3-(3-fluorophenyl)-5-methylisoxazol-4-yl)(4-(2-methoxyphenyl)piperazine-1-yl)methanone In a similar manner as described in Example 1, by using dichloromethane (30 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (586 mg, 1.48 mmol, 81%) was obtained.

$^1$H-NMR (400 MHz, CDCl$_3$, δ)=2.56 (s, 3H), 2.61 (brs, 2H), 3.07 (brs, 2H), 3.34 (brs, 2H), 3.86 (s, 3H), 3.97 (brs, 2H), 6.53 (m, 1H), 6.90 (m, 2H), 7.18 (m, 1H), 7.05 (m, 1H), 7.46 (m, 3H)

EXAMPLE 14

Synthesis of (3-(3-fluorophenyl)-5-methylisoxazol-4-yl)(4-(3-(trifluoromethyl)phenyl)piperazine-1-yl)methanone In a similar manner as described in Example 1, by using dichloromethane (30 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (506 mg, 1.17 mmol, 64%) was obtained.

$^1$H-NMR (400 MHz, CDCl$_3$, δ)=2.56 (s, 3H), 2.59 (brs, 2H), 3.03 (brs, 2H), 3.32 (brs, 2H), 3.88 (brs, 2H), 6.99 (m, 1H), 7.21 (m, 4H), 7.42 (m, 3H)

EXAMPLE 15

Synthesis of (3-(3-fluorophenyl)-5-methylisoxazol-4-yl)(4-(4-hydroxyphenyl)piperazine-1-yl)methanone In a similar manner as described in Example 1, by using dimethylformimide (15 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (424 mg, 1.84 mmol), a white solid required compound (486 mg, 1.27 mmol, 69%) was obtained.

$^1$H-NMR (400 MHz, CDCl$_3$, δ)=2.56 (s, 3H), 2.61 (brs, 2H), 3.07 (brs, 2H), 3.32 (brs, 2H), 3.95 (brs, 2H), 6.78 (m, 4H), 7.19 (m, 1H), 7.45 (m, 3H)

EXAMPLE 16

Synthesis of (3-(3-fluorophenyl)-5-methylisoxazol-4-yl)(4-(2-hydroxyphenyl)piperazine-1-yl)methanone In a similar manner as described in Example 1, by using dimethylformimide (15 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (424 mg, 1.84 mmol), a white solid required compound (462 mg, 1.21 mmol, 66%) was obtained.

$^1$H-NMR (400 MHz, CDCl$_3$, δ)=2.58 (s, 3H), 2.63 (brs, 2H), 3.00 (brs, 2H), 3.39 (brs, 2H), 4.02 (brs, 2H), 6.89 (m, 1H), 7.01 (m, 2H), 7.17 (m, 1H), 7.24 (m, 1H), 7.45 (m, 1H), 7.51 (m, 2H)

EXAMPLE 17

Synthesis of (3-(3-fluorophenyl)-5-methylisoxazol-4-yl)(4-(4-fluorophenyl)piperazine-1-yl)methanone In a similar manner as described in Example 1, by using dichloromethane (30 mL), 3-(3-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (511 mg, 1.33 mmol, 72%) was obtained.

$^1$H-NMR (400 MHz, CDCl$_3$, δ)=2.55 (s, 3H), 2.66 (brs, 2H), 2.99 (brs, 2H), 3.44 (brs, 2H), 3.88 (brs, 2H), 6.74 (m, 2H), 7.03 (m, 2H), 7.17 (m, 1H), 7.45 (m, 3H)

EXAMPLE 18

Synthesis of (3-(2-fluorophenyl)-5-methylisoxazol-4-yl)(4-(2-fluorophenyl)piperazine-1-yl)methanone In a similar manner as described in Example 1, by using dichloromethane (30 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (578 mg, 1.51 mmol, 82%) was obtained.

$^1$H-NMR (400 MHz, CDCl$_3$, δ)=2.56 (s, 3H), 2.71 (brs, 2H), 3.06 (brs, 2H), 3.38 (brs, 2H), 3.75 (brs, 2H), 6.10 (m, 3H), 6.79 (t, 1H), 7.19 (m, 1H), 7.40 (m, 1H), 7.57 (m, 2H)

EXAMPLE 19

Synthesis of (4-(3,4-dichlorophenyl)piperazine-1-yl)(3-(2-fluorophenyl)-5-methylisoxazol-4-yl)methanone In a similar manner as described in Example 1, by using dichloromethane (30 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (587 mg, 1.35 mmol, 74%) was obtained.

$^1$H-NMR (CDCl$_3$, 400 MHz, δ)=2.57 (s, 3H), 2.79 (brs, 2H), 3.01 (brs, 2H), 3.40 (brs, 2H), 3.73 (brs, 2H), 6.65 (dd, 1H), 6.87 (d, 1H), 7.16 (m, 1H), 7.27 (m, 1H), 7.40 (m, 1H), 7.54 (m, 2H)

EXAMPLE 20

Synthesis of (3-(2-fluorophenyl)-5-methylisoxazol-4-yl)(4-(3-methoxyphenyl)piperazine-1-yl)methanone In a similar manner as described in Example 1, by using dichloromethane (30 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (622 mg, 1.57 mmol, 86%) was obtained.

$^1$H-NMR (400 MHz, CDCl$_3$, δ)=2.57 (s, 3H), 2.63 (brs, 2H), 3.11 (brs, 2H), 3.32 (brs, 2H), 3.83 (brs, 2H), 3.82 (s, 3H), 6.43 (brs, 1H), 6.48 (m, 2H), 7.19 (m, 1H), 7.42 (m, 1H), 7.46 (dd, 1H), 7.54 (m, 1H), 7.78 (dd, 2H)

EXAMPLE 21

Synthesis of (3-(2-fluorophenyl)-5-methylisoxazol-4-yl)(4-(2-methoxyphenyl)piperazine-1-yl)methanone In a similar manner as described in Example 1, by using dichloromethane (30 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (532 mg, 1.35 mmol, 73%) was obtained.

$^1$H-NMR (400 MHz, CDCl$_3$, δ)=2.56 (s, 3H), 2.61 (brs, 2H), 2.99 (brs, 2H), 3.31 (brs, 2H), 3.79 (brs, 2H), 3.83 (s, 3H), 6.78 (brs, 1H), 6.84 (t, 1H), 6.91 (t, 1H), 7.19 (m, 1H), 7.42 (m, 1H), 7.59 (m, 2H), 7.69 (dd, 1H)

EXAMPLE 22

Synthesis of (3-(2-fluorophenyl)-5-methylisoxazol-4-yl)(4-(3-(trifluoromethyl)phenyl)piperazine-1-yl)methanone In a similar manner as described in Example 1, by using dichloromethane (30 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (501 mg, 1.15 mmol, 63%) was obtained.
$^1$H-NMR (400 MHz, CDCl$_3$, δ)=2.55 (s, 3H), 2.62 (brs, 2H), 3.03 (brs, 2H), 3.38 (brs, 2H), 7.02 (m, 2H), 7.19 (m, 1H), 7.23 (m, 1H), 7.42 (m, 1H), 7.54 (m, 2H)

EXAMPLE 23

Synthesis of (3-(2-fluorophenyl)-5-methylisoxazol-4-yl)(4-(4-hydroxyphenyl)piperazine-1-yl)methanone In a similar manner as described in Example 1, by using dimethylformimide (15 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (424 mg, 1.84 mmol), a white solid required compound (542 mg, 1.42 mmol, 77%) was obtained.
$^1$H-NMR (400 MHz, CDCl$_3$, δ)=2.56 (s, 3H), 2.61 (brs, 2H), 3.07 (brs, 2H), 3.32 (brs, 2H), 3.95 (brs, 2H), 6.78 (m, 4H), 7.19 (m, 1H), 7.40 (m, 1H), 7.57 (m, 2H)

EXAMPLE 24

Synthesis of (3-(2-fluorophenyl)-5-methylisoxazol-4-yl)(4-(2-hydroxyphenyl)piperazine-1-yl)methanone In a similar manner as described in Example 1, by using dimethylformimide (15 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (424 mg, 1.84 mmol), a white solid required compound (433 mg, 1.13 mmol, 62%) was obtained.
$^1$H-NMR (400 MHz, CDCl$_3$, δ)=2.57 (s, 3H), 2.61 (brs, 2H), 3.04 (brs, 2H), 3.35 (brs, 2H), 4.01 (brs, 2H), 6.91 (m, 1H), 7.03 (m, 2H), 7.17 (m, 1H), 7.20 (m, 1H), 7.43 (m, 1H), 7.58 (m, 2H)

EXAMPLE 25

Synthesis of (3-(2-fluorophenyl)-5-methylisoxazol-4-yl)(4-(4-fluorophenyl)piperazine-1-yl)methanone In a similar manner as described in Example 1, by using dichloromethane (30 mL), 3-(2-fluorophenyl)-5-methylisoxazol-4-carboxylic acid (407 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (538 mg, 1.40 mmol, 76%) was obtained.
$^1$H-NMR (400 MHz, CDCl$_3$, δ)=2.55 (s, 3H), 2.87 (brs, 4H), 3.05 (brs, 4H), 6.91 (m, 2H), 7.04 (m, 2H), 7.19 (m, 1H), 7.43 (m, 1H), 7.59 (m, 2H)

EXAMPLE 26

Synthesis of (4-(2-fluorophenyl)piperazine-1-yl)(5-methyl-3-(4-(trifluoromethoxy)phenyl)isoxazol-4-yl)methanone In a similar manner as described in Example 1, by using dichloromethane (30 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (536 mg, 1.20 mmol, 65%) was obtained.
$^1$H-NMR (400 MHz, CDCl$_3$, δ)=2.56 (s, 3H), 2.63 (brs, 2H), 3.06 (brs, 2H), 3.33 (brs, 2H), 3.94 (brs, 2H), 6.80 (t, 1H), 6.04 (m, 3H), 7.32 (d, 2H), 7.76 (d, 2H)

EXAMPLE 27

Synthesis of (4-(3,4-dichlorophenyl)piperazine-1-yl)(5-methyl-3-(4-(trifluoromethoxy)phenyl)isoxazol-4-yl)methanone In a similar manner as described in Example 1, by using dichloromethane (30 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a gel-like required compound (589 mg, 1.17 mmol, 64%) was obtained.
$^1$H-NMR (400 MHz, CDCl$_3$, δ)=2.55 (s, 3H), 2.68 (brs, 2H), 3.15 (brs, 2H), 3.28 (brs, 2H), 3.89 (brs, 2H), 6.65 (dd, 1H), 6.87 (d, 1H), 7.28 (t, 1H), 7.32 (dd, 2H), 7.74 (dd, 2H)

EXAMPLE 28

Synthesis of (4-(3-methoxyphenyl)piperazine-1-yl)(5-methyl-3-(4-(trifluoromethoxy)phenyl)isoxazol-4-yl)methanone In a similar manner as described in Example 1, by using dichloromethane (30 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3-methoxyphenyl)piperazine (353 mg, 1.84 mmol), a white solid required compound (622 mg, 1.35 mmol, 73%) was obtained.
$^1$H-NMR (400 MHz, CDCl$_3$, δ)=2.59 (s, 3H), 2.64 (brs, 2H), 3.17 (brs, 2H), 3.29 (brs, 2H), 3.75 (brs, 2H), 3.80 (s, 3H), 6.42 (brs, 1H), 6.52 (m, 2H), 7.43 (dd, 1H), 7.47 (d, 2H), 7.75 (d, 2H), 7.78 (dd, 1H)

EXAMPLE 29

Synthesis of (4-(2-methoxyphenyl)piperazine-1-yl)(5-methyl-3-(4-(trifluoromethoxy)phenyl)isoxazol-4-yl)methanone In a similar manner as described in Example 1, by using dichloromethane (30 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(2-methoxyphenyl)piperazine (353 mg, 1.84 mmol), a white solid required compound (604 mg, 1.33 mmol, 72%) was obtained.

$^1$H-NMR (400 MHz, CDCl$_3$, δ)=2.60 (brs, 5H), 2.98 (brs, 2H), 3.31 (brs, 2H), 3.85 (s, 3H), 6.76 (s, 1H), 6.87 (t, 1H), 6.91 (t, 1H), 7.65 (dd, 1H), 7.43 (d, 2H), 7.73 (d, 2H), 7.78 (brs, 2H)

EXAMPLE 30

Synthesis of (5-methyl-3-(4-(trifluoromethoxy)phenyl)isoxazol-4-yl)(4-(3-(trifluoromethyl)phenyl)piperazine-1-yl)methanone In a similar manner as described in Example 1, by using dichloromethane (30 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a gel-like required compound (574 mg, 1.15 mmol, 63%) was obtained.

$^1$H-NMR (400 MHz, CDCl$_3$, δ)=2.61 (s, 3H), 2.65 (brs, 2H), 3.13 (brs, 2H), 3.32 (brs, 2H), 7.10 (m, 2H), 7.14 (d, 1H), 7.41 (m, 1H), 7.46 (d, 2H), 7.77 (d, 2H)

EXAMPLE 31

Synthesis of (4-(4-hydroxyphenyl)piperazine-1-yl)(5-methyl-3-(4-(trifluoromethoxy)phenyl)isoxazol-4-yl)methanone In a similar manner as described in Example 1, by using dimethylformimide (15 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (502 mg, 1.12 mmol, 61%) was obtained.

$^1$H-NMR (400 MHz, DMSO, δ)=2.60 (brs, 2H), 2.62 (s, 3H), 3.08 (brs, 2H), 3.29 (brs, 2H), 3.91 (brs, 2H), 6.74 (m, 2H), 6.74 (m, 2H), 7.46 (d, 2H), 7.78 (d, 2H)

EXAMPLE 32

Synthesis of (4-(2-hydroxyphenyl)piperazine-1-yl)(5-methyl-3-(4-(trifluoromethoxy)phenyl)isoxazol-4-yl)methanone In a similar manner as described in Example 1, by using dimethylformimide (15 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (538 mg, 1.02 mmol, 65%) was obtained.

$^1$H-NMR (400 MHz, DMSO, δ)=2.62 (s, 3H), 2.63 (brs, 2H), 3.01 (brs, 2H), 3.38 (brs, 2H), 4.02 (brs, 2H), 6.87 (m, 1H), 7.08 (m, 2H), 7.25 (m, 1H), 7.43 (d, 2H), 7.73 (d, 2H)

EXAMPLE 33

Synthesis of (4-(4-fluorophenyl)piperazine-1-yl)(5-methyl-3-(4-trifluoromethoxy)phenyl)isoxazol-4-yl)methanone In a similar manner as described in Example 1, by using dichloromethane (30 mL), 5-methyl-3-(4-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (610 mg, 1.35 mmol, 74%) was obtained.

$^1$H-NMR (400 MHz, CDCl$_3$, δ)=2.62 (s, 3H), 2.91 (brs, 4H), 4.47 (brs, 4H), 6.96 (m, 2H), 7.07 (m, 2H), 7.44 (d, 2H), 7.75 (d, 2H)

EXAMPLE 34

Synthesis of (4-(2-fluorophenyl)piperazine-1-yl)(5-methyl-3-(2-(trifluoromethoxy)phenyl)isoxazol-4-yl)methanone In a similar manner as described in Example 1, by using dichloromethane (30 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (593 mg, 1.32 mmol, 72%) was obtained.

$^1$H-NMR (400 MHz, CDCl$_3$, δ)=2.56 (brs, 2H), 2.61 (s, 3H), 3.01 (brs, 2H), 3.31 (brs, 2H), 3.81 (brs, 2H), 6.80 (t, 1H), 6.99 (m, 2H), 7.05 (m, 1H), 7.40 (m, 1H), 7.44 (dd, 1H), 7.55 (m, 1H), 7.77 (dd, 1H)

EXAMPLE 35

Synthesis of (4-(3,4-dichlorophenyl)piperazine-1-yl)(5-methyl-3-(2-(trifluoromethoxy)phenyl)isoxazol-4-yl)methanone In a similar manner as described in Example 1, by using dichloromethane (30 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3,4-dichlorophenyl)piperazine (381 mg, 1.84 mmol), a white solid required compound (652 mg, 1.30 mmol, 71%) was obtained.

$^1$H-NMR (400 MHz, CDCl$_3$, δ)=2.60 (s, 3H), 2.61 (brs, 2H), 3.09 (brs, 2H), 3.27 (brs, 2H), 3.70 (brs, 2H), 6.66 (dd, 1H), 6.86 (d, 1H), 7.29 (t, 1H), 7.39 (d, 1H), 7.43 (t, 1H), 7.55 (t, 1H), 7.66 (dd, 1H)

EXAMPLE 36

Synthesis of (4-(3-methoxyphenyl)piperazine-1-yl)(5-methyl-3-(2-trifluoromethoxy)phenyl)isoxazol-4-yl)methanone In a similar manner as described in Example 1, by using dichloromethane (30 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a gel-like required compound (564 mg, 1.22 mmol, 66%) was obtained.

$^1$H-NMR (400 MHz, CDCl$_3$, δ)=2.60 (s, 3H), 2.65 (brs, 2H), 3.12 (brs, 2H), 3.31 (brs, 2H), 3.79 (brs, 2H), 3.81 (s, 3H), 6.40 (brs, 1H), 6.50 (m, 2H), 7.19 (t, 1H), 7.39 (m, 1H), 7.44 (dd, 1H), 7.54 (m, 1H), 7.77 (dd, 1H)

EXAMPLE 37

Synthesis of (4-(2-methoxyphenyl)piperazine-1-yl)(5-methyl-3-(2-trifluoromethoxy)phenyl)isoxazol-4-yl)methanone In a similar manner as described in Example 1, by using dichloromethane (30 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (570 mg, 1.24 mmol, 67%) was obtained.

$^1$H-NMR (400 MHz, CDCl$_3$, δ)=2.60 (brs, 2H), 2.61 (S, 3H), 2.99 (brs, 2H), 3.33 (brs, 2H), 3.78 (brs, 2H), 3.85 (s, 3H), 6.77 (brs, 1H), 6.89 (t, 1H), 6.92 (t, 1H), 7.05 (t, 1H), 7.42 (m, 2H), 7.55 (t, 1H), 7.66 (dd, 1H)

EXAMPLE 38

Synthesis of (5-methyl-3-(2-(trifluoromethoxy)phenyl)isoxazol-4-yl)(4-(3-(trifluoromethyl)phenyl)piperazine-1-yl)methanone In a similar manner as described in Example 1, by using dichloromethane (30 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a gel-like required compound (486 mg, 0.97 mmol, 53%) was obtained.

$^1$H-NMR (400 MHz, CDCl$_3$, δ)=2.61 (s, 3H), 2.69 (brs, 2H), 3.17 (brs, 2H), 3.32 (brs, 2H), 3.82 (brs, 2H), 7.01 (d, 1H), 7.02 (s, 1H), 7.16 (d, 1H), 7.40 (m, 2H), 7.45 (t, 1H), 7.55 (t, 1H), 7.68 (dd, 1H)

EXAMPLE 39

Synthesis of (4-(4-hydroxyphenyl)piperazine-1-yl)(5-methyl-3-(2-(trifluoromethoxy)phenyl)isoxazol-4-yl)methanone In a similar manner as described in Example 1, by using dimethylformimide (15 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (502 mg, 1.12 mmol, 61%) was obtained.

$^1$H-NMR (400 MHz, DMSO, δ)=2.61 (brs, 2H), 2.64 (s, 3H), 3.04 (brs, 2H), 3.29 (brs, 2H), 3.91 (brs, 2H), 6.76 (m, 4H), 7.53 (m, 2H), 7.60 (m, 1H), 7.69 (m, 1H)

EXAMPLE 40

Synthesis of (4-(2-hydroxyphenyl)piperazine-1-yl)(5-methyl-3-(2-(trifluoromethoxy)phenyl)isoxazol-4-yl)methanone In a similar manner as described in Example 1, by using dimethylformimide (15 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (536 mg, 1.20 mmol, 65%) was obtained.

$^1$H-NMR (400 MHz, CDCl$_3$, δ)=2.39 (brs, 2H), 2.63 (s, 3H), 2.89 (brs, 2H), 3.36 (brs, 2H), 3.86 (brs, 2H), 6.89 (m, 1H), 6.98 (m, 2H), 7.15 (m, 1H), 7.47 (m, 2H), 7.76 (m, 1H), 7.68 (dd, 1H)

EXAMPLE 41

Synthesis of (4-(4-fluorophenyl)piperazine-1-yl)(5-methyl-3-(2-(trifluoromethoxy)phenyl)isoxazol-4-yl)methanone In a similar manner as described in Example 1, by using dichloromethane (30 mL), 5-methyl-3-(2-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (536 mg, 1.20 mmol, 65%) was obtained.

$^1$H-NMR (400 MHz, CDCl$_3$, δ)=2.63 (s, 3H), 2.91 (brs, 4H), 3.51 (brs, 4H), 6.94 (m, 2H), 7.07 (m, 2H), 7.53 (m, 2H), 7.63 (m, 1H), 7.74 (m, 1H)

EXAMPLE 42

Synthesis of (4-(2-fluorophenyl)piperazine-1-yl)(5-methyl-3-(3-(trifluoromethyl)phenyl)isoxazol-4-yl)methanone In a similar manner as described in Example 1, by using dichloromethane (30 mL), methyl-3-(3-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (536 mg, 1.24 mmol, 67%) was obtained.

$^1$H-NMR (400 MHz, CDCl$_3$, δ)=2.68 (s, 3H), 2.73 (brs, 2H), 3.01 (brs, 2H), 3.41 (brs, 2H), 3.72 (brs, 2H), 6.09 (m, 3H), 6.83 (t, 1H), 7.34 (m, 1H), 7.72 (m, 1H), 7.86 (m, 2H)

EXAMPLE 43

Synthesis of (4-(3,4-dichlorophenyl)piperazine-1-yl)(5-methyl-3-(3-(trifluoromethyl)phenyl)isoxazol-4-yl)methanone In a similar manner as described in Example 1, by using dichloromethane (30 mL), 5-methyl-3-(3-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (644 mg, 1.24 mmol, 68%) was obtained.

$^1$H-NMR (400 MHz, CDCl$_3$, δ)=2.62 (s, 3H), 2.73 (brs, 2H), 3.12 (brs, 2H), 3.48 (brs, 2H), 3.76 (brs, 2H), 6.70 (dd, 1H), 6.84 (d, 1H), 7.31 (m, 1H), 7.54 (d, 1H), 7.72 (m, 1H), 7.82 (m, 2H)

EXAMPLE 44

Synthesis of (4-(3-methoxyphenyl)piperazine-1-yl)(5-methyl-3-(3-(trifluoromethyl)phenyl)isoxazol-4-yl)methanone In a similar manner as described in Example 1, by using dichloromethane (30 mL), 5-methyl-3-(3-(trifluoromethyl)

phenyl)isoxazol-4-carboxylic acid (500 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a gel-like required compound (602 mg, 1.37 mmol, 75%) was obtained.

$^1$H-NMR (400 MHz, CDCl$_3$, δ)=2.61 (brs, 2H), 2.69 (s, 3H), 3.15 (brs, 2H), 3.46 (brs, 2H), 4.12 (brs, 2H), 6.48 (brs, 1H), 6.6.50 (m, 2H), 7.31 (dd, 1H), 7.37 (m, 1H), 7.75 (m, 1H), 7.85 (m, 2H)

EXAMPLE 45

Synthesis of (4-(2-methoxyphenyl)piperazine-1-yl) (5-methyl-3-(3-(trifluoromethyl)phenyl)isoxazol-4-yl)methanone In a similar manner as described in Example 1, by using dichloromethane (30 mL), 5-methyl-3-(3-(trifluoromethyl) phenyl)isoxazol-4-carboxylic acid (500 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (524 mg, 1.18 mmol, 64%) was obtained.

$^1$H-NMR (400 MHz, CDCl$_3$, δ)=2.59 (S, 3H), 2.73 (brs, 2H), 2.08 (brs, 2H), 3.41 (brs, 2H), 3.73 (brs, 2H), 3.84 (s, 3H), 6.47 (brs, 1H), 6.52 (m, 2H), 7.13 (t, 1H), 7.32 (m, 1H), 7.76 (m, 1H), 7.83 (m, 2H)

EXAMPLE 46

Synthesis of (5-methyl-3-(3-trifluoromethyl)phenyl) isoxazol-4-yl)(4-(3-(trifluoromethyl)phenyl)piperazine-1-yl)methanone In a similar manner as described in Example 1, by using dichloromethane (30 mL), 5-methyl-3-(3-(trifluoromethyl) phenyl)isoxazol-4-carboxylic acid (500 mg, 1.84 mmol), 1-ethyl-3-(dimethylaminopropyl)carbodiimide hydrochloride (388 mg, 2.02 mmol) and 1-(3-(trifluoromethyl)phenyl) piperazine (424 mg, 1.84 mmol), a gel-like required compound (501 mg, 1.04 mmol, 56%) was obtained.

$^1$H-NMR (400 MHz, CDCl$_3$, δ)=2.60 (brs, 2H), 2.62 (s, 3H), 3.28 (brs, 2H), 3.42 (brs, 2H), 3.54 (brs, 2H), 4.03 (brs, 2H), 6.92 (m, 2H), 7.04 (m, 1H), 7.32 (m, 1H), 7.76 (m, 2H), 7.85 (m, 2H)

EXAMPLE 47

Synthesis of (4-(4-hydroxyphenyl)piperazine-1-yl) (5-methyl-3-(3-(trifluoromethyl)phenyl)isoxazol-4-yl)methanone In a similar manner as described in Example 1, by using dimethylformimide (15 mL), 5-methyl-3-(3-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (438 mg, 1.02 mmol, 55%) was obtained.

$^1$H-NMR (400 MHz, CDCl$_3$, δ)=2.67 (s, 3H), 2.71 (brs, 4H), 3.89 (brs, 4H), 6.81 (m, 4H), 7.36 (m, 1H), 7.72 (m, 1H), 7.86 (m, 2H)

EXAMPLE 48

Synthesis of (4-(2-hydroxyphenyl)piperazine-1-yl) (5-methyl-3-(3-(trifluoromethyl)phenyl)isoxazol-4-yl)methanone In a similar manner as described in Example 1, by using dimethylformimide (15 mL), 5-methyl-3-(3-(trifluoromethyl)phenyl)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (466 mg, 1.08 mmol, 59%) was obtained.

$^1$H-NMR (400 MHz, CDCl$_3$, δ)=2.48 (brs, 2H), 2.64 (s, 3H), 2.77 (brs, 2H), 3.53 (brs, 2H), 3.87 (brs, 2H), 6.92 (m, 3H), 7.19 (m, 1H), 7.36 (m, 1H), 7.72 (m, 1H), 7.84 (m, 2H)

EXAMPLE 49

Synthesis of (4-(4-fluorophenyl)piperazine-1-yl)(5-methyl-3-(3-(trifluoromethyl)phenyl)isoxazol-4-yl) methanone In a similar manner as described in Example 1, by using dichloromethane (30 mL), 5-methyl-3-(3-(trifluoromethyl) phenyl)isoxazol-4-carboxylic acid (500 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (566 mg, 1.31 mmol, 71%) was obtained.

$^1$H-NMR (400 MHz, CDCl$_3$, δ)=2.68 (s, 3H), 2.94 (brs, 4H), 3.38 (brs, 4H), 6.94 (m, 2H), 7.06 (m, 2H), 7.39 (m, 1H), 7.75 (m, 1H), 7.84 (m, 2H)

EXAMPLE 50

Synthesis of (4-(2-fluorophenyl)piperazine-1-yl)(5-methyl-3-(3-(trifluoromethoxy)phenyl)isoxazol-4-yl) methanone In a similar manner as described in Example 1, by using dichloromethane (30 mL), 5-methyl-3-(3-(trifluoromethoxy) isoxazol-4-carboxylic acid (500 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (542 mg, 1.21 mmol, 65%) was obtained.

$^1$H-NMR (400 MHz, CDCl$_3$, δ)=2.53 (brs, 2H), 2.41 (s, 3H), 3.03 (brs, 2H), 3.48 (brs, 2H), 3.79 (brs, 2H), 6.84 (t, 1H), 7.02 (m, 2H), 7.06 (m, 2H), 7.42 (m, 2H), 7.61 (m, 2H)

EXAMPLE 51

Synthesis of (4-(3,4-dichlorophenyl)piperazine-1-yl) (5-methyl-3-(3-(trifluoromethoxy)phenyl)isoxazol-4-yl)methanone In a similar manner as described in Example 1, by using dichloromethane (30 mL), 5-methyl-3-(3-(trifluoromethoxy) isoxazol-4-carboxylic acid (500 mg, 1.84 mmol), 1-ethyl-3-(dimethylaminopropyl)carbodiimide hydrochloride (388 mg, 2.02 mmol) and 1-(3,4-dichlorophenyl)piperazine (381 mg, 1.84 mmol), a white solid required compound (602 mg, 1.20 mmol, 65%) was obtained.

¹H-NMR (400 MHz, CDCl₃, δ)=2.59 (brs, 2H), 2.72 (s, 3H), 3.12 (brs, 2H), 3.28 (brs, 2H), 3.70 (brs, 2H), 6.69 (dd, 1H), 6.82 (d, 1H), 7.20 (t, 1H), 7.44 (m, 2H), 7.58 (m, 2H)

EXAMPLE 52

Synthesis of (4-(3-methoxyphenyl)piperazine-1-yl) (5-methyl-3-(3-(trifluoromethoxy)phenyl)isoxazol-4-yl)methanone In a similar manner as described in Example 1, by using dichloromethane (30 mL), 5-methyl-3-(3-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a gel-like required compound (564 mg, 1.22 mmol, 66%) was obtained.

¹H-NMR (400 MHz, CDCl₃, δ)=2.69 (s, 3H), 2.72 (brs, 2H), 3.16 (brs, 2H), 3.33 (brs, 2H), 3.82 (brs, 2H), 3.83 (s, 3H), 6.42 (brs, 1H), 6.58 (m, 2H), 7.22 (t, 1H), 7.44 (m, 2H), 7.59 (m, 2H)

EXAMPLE 53

Synthesis of (4-(2-methoxyphenyl)piperazine-1-yl) (5-methyl-3-(3-(trifluoromethoxy)phenyl)isoxazol-4-yl)methanone In a similar manner as described in Example 1, by using dichloromethane (30 mL), 5-methyl-3-(3-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (633 mg, 1.37 mmol, 75%) was obtained.

¹H-NMR (400 MHz, CDCl₃, δ)=2.68 (brs, 2H), 2.70 (S, 3H), 2.98 (brs, 2H), 3.43 (brs, 2H), 3.87 (brs, 2H), 3.82 (s, 3H), 6.76 (brs, 1H), 6.91 (t, 1H), 6.96 (t, 1H), 7.04 (t, 1H), 7.41 (m, 2H), 7.65 (m, 2H)

EXAMPLE 54

Synthesis of (5-methyl-3-(3-(trifluoromethoxy)phenyl)isoxazol-4-yl)(4-(3-trifluoromethyl)phenyl)piperazine-1-yl)methanone In a similar manner as described in Example 1, by using dichloromethane (30 mL), 5-methyl-3-(3-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a gel-like required compound (501 mg, 1.00 mmol, 55%) was obtained.

¹H-NMR (400 MHz, CDCl₃, δ)=2.64 (s, 3H), 2.70 (brs, 2H), 3.21 (brs, 2H), 3.30 (brs, 2H), 3.84 (brs, 2H), 7.02 (d, 1H), 7.08 (s, 1H), 7.18 (d, 1H), 7.40 (m, 1H), 7.43 (m, 2H), 7.68 (m, 2H)

EXAMPLE 55

Synthesis of (4-(4-hydroxyphenyl)piperazine-1-yl) (5-methyl-3-(3-(trifluoromethoxy)phenyl)isoxazol-4-yl)methanone In a similar manner as described in Example 1, by using dimethylformimide (15 mL), 5-methyl-3-(3-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (502 mg, 1.12 mmol, 61%) was obtained.

¹H-NMR (400 MHz, DMSO, δ)=2.62 (brs, 4H), 2.69 (s, 3H), 3.49 (brs, 4H), 6.74 (m, 4H), 7.47 (m, 2H), 7.69 (m, 2H)

EXAMPLE 56

Synthesis of (4-(2-hydroxyphenyl)piperazine-1-yl) (5-methyl-3-(3-(trifluoromethoxy)phenyl)isoxazol-4-yl)methanone In a similar manner as described in Example 1, by using dimethylformimide (15 mL), 5-methyl-3-(3-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (536 mg, 1.20 mmol, 65%) was obtained.

¹H-NMR (400 MHz, CDCl₃, δ)=2.34 (brs, 2H), 2.63 (s, 3H), 2.85 (brs, 2H), 3.35 (brs, 2H), 3.84 (brs, 2H), 6.85 (m, 1H), 6.97 (m, 2H), 7.20 (m, 1H), 7.45 (m, 2H), 7.69 (m, 2H)

EXAMPLE 57

Synthesis of (4-(4-fluorophenyl)piperazine-1-yl)(5-methyl-3-(3-(trifluoromethoxy)phenyl)isoxazol-4-yl) methanone In a similar manner as described in Example 1, by using dichloromethane (30 mL), 5-methyl-3-(3-(trifluoromethoxy)isoxazol-4-carboxylic acid (500 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (536 mg, 1.20 mmol, 65%) was obtained.

¹H-NMR (400 MHz, CDCl₃, δ)=2.64 (s, 3H), 2.94 (brs, 4H), 3.58 (brs, 4H), 6.90 (m, 2H), 7.21 (m, 2H), 7.50 (m, 2H), 7.63 (m, H)

EXAMPLE 58

Synthesis of (5-amino-3-(2-chlorophenyl)isoxazol-4-yl)(4-(2-fluorophenyl)piperazine-1-yl)methanone In a similar manner as described in Example 1, by using dichloromethane (30 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (532 mg, 1.33 mmol, 72%) was obtained.

¹H-NMR (400 MHz, DMSO, δ)=2.73 (brs, 2H), 3.04 (brs, 2H), 3.45 (brs, 2H), 3.73 (brs, 2H), 6.09 (m, 3H), 6.86 (m, 1H), 7.41 (s, 2H), 7.44 (m, 3H), 7.54 (m, 1H)

EXAMPLE 59

Synthesis of (5-amino-3-(2-chlorophenyl)isoxazol-4-yl)(4-(3,4-dichlorophenyl)piperazine-1-yl)methanone In a similar manner as described in Example 1, by using dichloromethane (30 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (577 mg, 1.35 mmol, 73%) was obtained.

$^1$H-NMR (400 MHz, DMSO, δ)=2.98 (brs, 4H), 3.43 (brs, 4H), 6.86 (t, 1H), 7.10 (d, 1H), 7.40 (s, 2H), 7.50 (m, 5H)

EXAMPLE 60

Synthesis of (5-amino-3-(2-chlorophenyl)isoxazol-4-yl)(4-(3-methoxyphenyl)piperazine-1-yl)methanone In a similar manner as described in Example 1, by using dichloromethane (30 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (516 mg, 1.25 mmol, 68%) was obtained.

$^1$H-NMR (400 MHz, DMSO, δ)=2.88 (brs, 4H), 3.43 (brs, 4H), 3.71 (s, 3H), 6.38 (m, 2H), 6.46 (dd, 1H), 7.10 (m, 1H), 7.38 (s, 2H), 7.51 (m, 4H)

EXAMPLE 61

Synthesis of (5-amino-3-(2-chlorophenyl)isoxazol-4-yl)(4-(2-methoxyphenyl)piperazine-1-yl)methanone In a similar manner as described in Example 1, by using dichloromethane (30 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (523 mg, 1.27 mmol, 69%) was obtained.

$^1$H-NMR (400 MHz, DMSO, δ)=2.66 (brs, 4H), 3.40 (brs, 4H), 3.76 (s, 3H), 6.76 (d, 1H), 6.85 (t, 1H), 6.95 (m, 2H), 7.38 (s, 2H), 7.50 (m, 3H), 7.57 (m, 1H)

EXAMPLE 62

Synthesis of (5-amino-3-(2-chlorophenyl)isoxazol-4-yl)(4-(3-(trifluoromethyl)phenyl)piperazine-1-yl)methanone In a similar manner as described in Example 1, by using dichloromethane (30 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (633 mg, 1.40 mmol, 76%) was obtained.

$^1$H-NMR (400 MHz, DMSO, δ)=2.61 (brs, 2H), 3.14 (brs, 2H), 3.35 (brs, 2H), 7.15 (m, 2H), 7.17 (d, 1H), 7.46 (m, 1H), 7.39 (s, 2H), 7.54 (m, 3H), 7.59 (m, 1H)

EXAMPLE 63

Synthesis of (5-amino-3-(2-chlorophenyl)isoxazol-4-yl)(4-(4-hydroxyphenyl)piperazine-1-yl)methanone In a similar manner as described in Example 1, by using dimethylformimide (15 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (504 mg, 1.26 mmol, 69%) was obtained.

$^1$H-NMR (400 MHz, DMSO, δ)=2.62 (brs, 2H), 3.09 (brs, 2H), 3.31 (brs, 2H), 3.95 (brs, 2H), 6.80 (m, 4H), 7.31 (s, 2H), 7.50 (m, 3H), 7.53 (m, 1H)

EXAMPLE 64

Synthesis of (5-amino-3-(2-chlorophenyl)isoxazol-4-yl)(4-(2-hydroxyphenyl)piperazine-1-yl)methanone In a similar manner as described in Example 1, by using dimethylformimide (15 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (518 mg, 1.30 mmol, 71%) was obtained.

$^1$H-NMR (400 MHz, DMSO, δ)=2.60 (brs, 2H), 3.04 (brs, 2H), 3.32 (brs, 2H), 3.99 (brs, 2H), 6.87 (m, 1H), 7.00 (m, 2H), 7.19 (m, 1H), 7.41 (s, 2H), 7.54 (m, 3H), 7.56 (m, 1H)

EXAMPLE 65

Synthesis of (5-amino-3-(2-chlorophenyl)isoxazol-4-yl)(4-(4-fluorophenyl)piperazine-1-yl)methanone In a similar manner as described in Example 1, by using dichloromethane (30 mL), 5-amino-3-(2-chlorophenyl)isoxazol-4-carboxylic acid (440 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (561 mg, 1.40 mmol, 76%) was obtained.

$^1$H-NMR (400 MHz, DMSO, δ)=2.84 (brs, 4H), 3.45 (brs, 4H), 6.91 (m, 2H), 7.03 (m, 2H), 7.36 (s, 2H), 7.52 (m, 3H), 7.59 (m, 1H)

EXAMPLE 66

Synthesis of (5-amino-3-(3-fluorophenyl)isoxazol-4-yl)(4-(2-fluorophenyl)piperazine-1-yl)methanone In a similar manner as described in Example 1, by using dichloromethane (30 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (508 mg, 1.32 mmol, 72%) was obtained.

$^1$H-NMR (400 MHz, CDCl$_3$, δ)=2.72 (brs, 2H), 3.04 (brs, 2H), 3.39 (brs, 2H), 3.69 (brs, 2H), 6.05 (m, 3H), 6.83 (t, 1H), 7.26 (m, 1H), 7.35 (brs, 2H), 7.45 (m, 3H)

EXAMPLE 67

Synthesis of (5-amino-3-(3-fluorophenyl)isoxazol-4-yl)(4-(3,4-dichlorophenyl)piperazine-1-yl)methanone In a similar manner as described in Example 1, by using dichloromethane (30 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (596 mg, 1.37 mmol, 74%) was obtained.

$^1$H-NMR (400 MHz, CDCl$_3$, δ)=2.73 (brs, 2H), 3.02 (brs, 2H), 3.39 (brs, 2H), 3.69 (brs, 2H), 6.65 (dd, 1H), 6.87 (d, 1H), 7.20 (m, 1H), 7.21 (m, 1H), 7.36 (brs, 2H), 7.43 (m, 3H)

EXAMPLE 68

Synthesis of (5-amino-3-(3-fluorophenyl)isoxazol-4-yl)(4-(3-methoxyphenyl)piperazine-1-yl)methanone In a similar manner as described in Example 1, by using dichloromethane (30 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (601 mg, 1.52 mmol, 82%) was obtained.

$^1$H-NMR (400 MHz, CDCl$_3$, δ)=2.61 (brs, 2H), 3.14 (brs, 2H), 3.30 (brs, 2H), 3.78 (brs, 2H), 3.80 (s, 3H), 6.42 (brs, 1H), 6.53 (m, 2H), 7.19 (m, 1H), 7.37 (brs, 2H), 7.43 (m, 3H), 7.46 (dd, 1H), 7.76 (dd, 1H)

EXAMPLE 69

Synthesis of (5-amino-3-(3-fluorophenyl)isoxazol-4-yl)(4-(2-methoxyphenyl)piperazine-1-yl)methanone In a similar manner as described in Example 1, by using dichloromethane (30 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (482 mg, 1.21 mmol, 66%) was obtained.

$^1$H-NMR (400 MHz, CDCl$_3$, δ)=2.63 (brs, 2H), 3.02 (brs, 2H), 3.36 (brs, 2H), 3.76 (brs, 2H), 3.89 (brs, 2H), 6.75 (brs, 1H), 6.89 (m, 1H), 6.90 (m, 1H), 7.24 (m, 1H), 7.33 (brs, 2H), 7.45 (m, 3H), 7.65 (dd, 1H)

EXAMPLE 70

Synthesis of (5-amino-3-(3-fluorophenyl)isoxazol-4-yl)(4-(3-(trifluoromethyl)phenyl)piperazine-1-yl)methanone In a similar manner as described in Example 1, by using dichloromethane (30 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(3-trifluoromethyl)phenyl)piperazine (424 mg, 1.84 mmol), a white solid required compound (639 mg, 1.47 mmol, 80%) was obtained.

$^1$H-NMR (400 MHz, CDCl$_3$, δ)=2.61 (brs, 2H), 3.17 (brs, 2H), 3.35 (brs, 2H), 7.01 (m, 2H), 7.15 (d, 1H), 7.21 (m, 1H), 7.39 (brs, 2H), 7.42 (m, 3H), 7.45 (m, 1H)

EXAMPLE 71

Synthesis of (5-amino-3-(3-fluorophenyl)isoxazol-4-yl)(4-(4-hydroxyphenyl)piperazine-1-yl)methanone In a similar manner as described in Example 1, by using dimethylformimide (15 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (483 mg, 1.26 mmol, 68%) was obtained.

$^1$H-NMR (400 MHz, CDCl$_3$, δ)=2.60 (brs, 2H), 3.14 (brs, 2H), 3.36 (brs, 2H), 3.99 (brs, 2H), 6.83 (m, 4H), 7.20 (m, 1H), 7.39 (brs, 2H), 7.45 (m, 3H)

EXAMPLE 72

Synthesis of (5-amino-3-(3-fluorophenyl)isoxazol-4-yl)(4-(2-hydroxyphenyl)piperazine-1-yl)methanone In a similar manner as described in Example 1, by using dimethylformimide (15 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (312 mg, 1.84 mmol), a white solid required compound (381 mg, 0.81 mmol, 44%) was obtained.

$^1$H-NMR (400 MHz, CDCl$_3$, δ)=2.61 (brs, 2H), 3.06 (brs, 2H), 3.42 (brs, 2H), 4.02 (brs, 2H), 6.89 (m, 1H), 7.06 (m, 1H), 7.24 (m, 2H), 7.41 (brs, 2H), 7.48 (m, 3H)

EXAMPLE 73

Synthesis of (5-amino-3-(3-fluorophenyl)isoxazol-4-yl)(4-(4-fluorophenyl)piperazine-1-yl)methanone In a similar manner as described in Example 1, by using dichloromethane (30 mL), 5-amino-3-(3-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (576 mg, 1.50 mmol, 81%) was obtained.

$^1$H-NMR (400 MHz, DMSO, δ)=2.91 (brs, 4H), 3.50 (brs, 4H), 6.97 (m, 2H), 7.10 (m, 2H), 7.28 (m, 1H), 7.37 (brs, 2H), 7.46 (m, 3H)

EXAMPLE 74

Synthesis of (5-amino-3-(2-fluorophenyl)isoxazol-4-yl)(4-(2-fluorophenyl)piperazine-1-yl)methanone In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (533 mg, 1.39 mmol, 75%) was obtained.

$^1$H-NMR (400 MHz, CDCl$_3$, δ)=2.69 (brs, 2H), 2.92 (brs, 2H), 3.40 (brs, 2H), 3.85 (brs, 2H), 6.62 (m, 1H), 6.78 (m, 1H), 7.06 (m, 1H), 7.27 (m, 1H), 7.37 (brs, 2H), 7.47 (m, 1H), 7.56 (m, 2H)

EXAMPLE 75

Synthesis of (5-amino-3-(2-fluorophenyl)isoxazol-4-yl)(4-(3,4-dichlorophenyl)piperazine-1-yl)methanone In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (613 mg, 1.49 mmol, 81%) was obtained.

$^1$H-NMR (400 MHz, CDCl$_3$, δ)=2.63 (brs, 2H), 3.09 (brs, 2H), 3.22 (brs, 2H), 3.87 (brs, 2H), 6.66 (dd, 1H), 6.87 (d, 1H), 7.28 (m, 1H), 7.36 (s, 2H), 7.37 (m, 1H), 7.48 (m, 1H), 7.57 (m, 2H)

EXAMPLE 76

Synthesis of (5-amino-3-(2-fluorophenyl)isoxazol-4-yl)(4-(3-methoxyphenyl)piperazine-1-yl)methanone In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (558 mg, 1.41 mmol, 77%) was obtained.

$^1$H-NMR (400 MHz, CDCl$_3$, δ)=2.64 (brs, 2H), 3.19 (brs, 2H), 3.30 (brs, 2H), 3.80 (s, 3H), 3.93 (brs, 2H), 6.42 (m, 1H), 6.48 (m, 2H), 7.13 (m, 1H), 7.26 (m, 1H), 7.36 (brs, 2H), 7.47 (m, 1H), 7.61 (m, 2H)

EXAMPLE 77

Synthesis of (5-amino-3-(2-fluorophenyl)isoxazol-4-yl)(4-(2-methoxyphenyl)piperazine-1-yl)methanone In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (464 mg, 1,170.64 mmol, 77%) was obtained.

$^1$H-NMR (400 MHz, CDCl$_3$, δ)=2.57 (brs, 2H), 3.03 (brs, 2H), 3.32 (brs, 2H), 3.83 (s, 3H), 3.95 (brs, 2H), 6.55 (m, 1H), 6.90 (m, 2H), 7.04 (m, 1H), 7.25 (m, 1H), 7.37 (brs, 2H), 7.45 (m, 1H), 7.59 (m, 2H)

EXAMPLE 78

Synthesis of (5-amino-3-(2-fluorophenyl)isoxazol-4-yl)(4-(3-(trifluoromethyl)phenyl)piperazine-1-yl)methanone In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(3-trifluoromethyl)phenyl)piperazine (424 mg, 1.84 mmol), a white solid required compound (596 mg, 1.37 mmol, 75%) was obtained.

$^1$H-NMR (400 MHz, CDCl$_3$, δ)=2.62 (brs, 2H), 3.07 (brs, 2H), 3.33 (brs, 2H), 3.90 (brs, 2H), 7.00 (m, 1H), 7.24 (m, 4H), 7.32 (brs, 2H), 7.44 (m, 1H), 7.59 (m, 2H)

EXAMPLE 79

Synthesis of (5-amino-3-(2-fluorophenyl)isoxazol-4-yl)(4-(4-hydroxyphenyl)piperazine-1-yl)methanone In a similar manner as described in Example 1, by using dimethylformimide (15 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (412 mg, 1.08 mmol, 59%) was obtained.

$^1$H-NMR (400 MHz, CDCl$_3$, δ)=2.61 (brs, 2H), 3.07 (brs, 2H), 3.32 (brs, 2H), 3.95 (brs, 2H), 6.77 (m, 4H), 7.22 (m, 1H), 7.33 (brs, 2H), 7.50 (m, 1H), 7.63 (m, 2H)

EXAMPLE 80

Synthesis of (5-amino-3-(2-fluorophenyl)isoxazol-4-yl)(4-(2-hydroxyphenyl)piperazine-1-yl)methanone In a similar manner as described in Example 1, by using dimethylformimide (15 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (439 mg, 1.15 mmol, 62%) was obtained.

$^1$H-NMR (400 MHz, CDCl$_3$, δ)=2.62 (brs, 2H), 3.02 (brs, 2H), 3.38 (brs, 2H), 4.01 (brs, 2H), 6.60 (m, 1H), 6.83 (m, 3H), 7.25 (m, 1H), 7.33 (brs, 2H), 7.47 (m, 1H), 7.63 (m, 2H)

EXAMPLE 81

Synthesis of (5-amino-3-(2-fluorophenyl)isoxazol-4-yl)(4-(4-fluorophenyl)piperazine-1-yl)methanone In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (538 mg, 1.40 mmol, 76%) was obtained.

$^1$H-NMR (400 MHz, DMSO, δ)=2.89 (brs, 4H), 3.49 (brs, 4H), 6.92 (m, 2H), 7.06 (m, 2H), 7.31 (m, 2H), 7.33 (brs, 2H), 7.54 (m, 2H)

EXAMPLE 82

Synthesis of (5-amino-3-(2-(trifluoromethoxy)phenyl)isoxazol-4-yl)(4-(2-fluorophenyl)piperazine-1-yl)methanone In a similar manner as described in Example 1, by using dichloromethane (30 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (576 mg, 1.28 mmol, 70%) was obtained.

$^1$H-NMR (400 MHz, DMSO, δ)=2.71 (brs, 2H), 3.04 (brs, 2H), 3.43 (brs, 2H), 3.69 (brs, 2H), 6.07 (m, 3H), 6.79 (t, 1H), 7.31 (brs, 2H), 7.41 (m, 3H), 7.54 (m, 1H)

EXAMPLE 83

Synthesis of (5-amino-3-(2-(trifluoromethoxy)phenyl)isoxazol-4-yl)(3,4-dichlorophenyl)piperazine-1-yl)methanone In a similar manner as described in Example 1, by using dichloromethane (30 mL), 5-amino-3-(2-(trifluoromethoxy)

phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (713 mg, 1.42 mmol, 77%) was obtained.

$^1$H-NMR (400 MHz, DMSO, δ)=2.73 (brs, 2H), 3.03 (brs, 2H), 3.45 (brs, 2H), 3.71 (brs, 2H), 6.65 (dd, 1H), 6.87 (d, 1H), 7.29 (m, 1H), 7.31 (brs, 2H), 7.41 (m, 3H), 7.54 (m, 1H)

EXAMPLE 84

Synthesis of (5-amino-3-(2-(trifluoromethoxy)phenyl)isoxazol-4-yl)(4-(3-methoxyphenyl)piperazine-1-yl)methanone In a similar manner as described in Example 1, by using dichloromethane (30 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (592 mg, 1.28 mmol, 70%) was obtained.

$^1$H-NMR (400 MHz, DMSO, δ)=2.65 (brs, 2H), 3.12 (brs, 2H), 3.31 (brs, 2H), 3.79 (brs, 2H), 3.81 (s, 3H), 6.40 (brs, 1H), 6.50 (m, 2H), 7.32 (brs, 2H), 7.45 (m, 3H), 7.44 (dd, 1H), 7.59 (m, 1H), 7.77 (dd, 1H)

EXAMPLE 85

Synthesis of (5-amino-3-(2-(trifluoromethoxy)phenyl)isoxazol-4-yl)(4-(2-methoxyphenyl)piperazine-1-yl)methanone In a similar manner as described in Example 1, by using dichloromethane (30 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (559 mg, 1.21 mmol, 66%) was obtained.

$^1$H-NMR (400 MHz, DMSO, δ)=2.62 (brs, 2H), 2.95 (brs, 2H), 3.31 (brs, 2H), 3.75 (brs, 2H), 3.89 (s, 3H), 6.78 (brs, 1H), 6.86 (t, 1H), 6.91 (t, 1H), 7.32 (brs, 2H), 7.41 (m, 3H), 7.54 (m, 1H), 7.69 (dd, 1H)

EXAMPLE 86

Synthesis of (5-amino-3-(2-(trifluoromethoxy)phenyl)isoxazol-4-yl)(4-(3-(trifluoromethyl)phenyl)piperazine-1-yl)methanone In a similar manner as described in Example 1, by using dichloromethane (30 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (633 mg, 1.27 mmol, 69%) was obtained.

$^1$H-NMR (400 MHz, DMSO, δ)=2.61 (brs, 2H), 3.13 (brs, 2H), 3.35 (brs, 2H), 7.01 (m, 2H), 7.15 (d, 1H), 7.31 (brs, 2H), 7.45 (m, 4H), 7.58 (m, 1H)

EXAMPLE 87

Synthesis of (5-amino-3-(2-(trifluoromethoxy)phenyl)isoxazol-4-yl)(4-(4-hydroxyphenyl)piperazine-1-yl)methanone In a similar manner as described in Example 1, by using dimethylformimide (15 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (608 mg, 1.36 mmol, 73%) was obtained.

$^1$H-NMR (400 MHz, DMSO, δ)=2.60 (brs, 2H), 3.34 (brs, 2H), 3.29 (brs, 2H), 3.98 (brs, 2H), 6.71 (m, 4H), 7.31 (brs, 2H), 7.45 (m, 3H), 7.55 (m, 1H)

EXAMPLE 88

Synthesis of (5-amino-3-(2-(trifluoromethoxy)phenyl)isoxazol-4-yl)(4-(2-hydroxyphenyl)piperazine-1-yl)methanone In a similar manner as described in Example 1, by using dimethylformimide (15 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (551 mg, 1.23 mmol, 67%) was obtained.

$^1$H-NMR (400 MHz, DMSO, δ)=2.63 (brs, 2H), 3.04 (brs, 2H), 3.33 (brs, 2H), 4.03 (brs, 2H), 6.85 (m, 1H), 7.04 (m, 2H), 7.20 (m, 1H), 7.30 (brs, 2H), 7.47 (m, 3H), 7.61 (m, 1H)

EXAMPLE 89

Synthesis of (5-amino-3-(2-(trifluoromethoxy)phenyl)isoxazol-4-yl)(4-(4-fluorophenyl)piperazine-1-yl)methanone In a similar manner as described in Example 1, by using dichloromethane (30 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (607 mg, 1.35 mmol, 73%) was obtained.

$^1$H-NMR (400 MHz, DMSO, δ)=2.87 (brs, 4H), 3.47 (brs, 4H), 6.91 (m, 2H), 7.05 (m, 2H), 7.31 (brs, 2H), 7.44 (m, 3H), 7.62 (m, 1H)

EXAMPLE 90

Synthesis of (5-amino-3-(2-(trifluoromethyl)phenyl)isoxazol-4-yl)(4-(2-fluorophenyl)piperazine-1-yl)methanone In a similar manner as described in Example 1, by using dichloromethane (30 mL), 5-amino-3-(2-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (573 mg, 1.32 mmol, 72%) was obtained.

$^1$H-NMR (400 MHz, DMSO, δ)=2.72 (brs, 2H), 3.06 (brs, 2H), 3.39 (brs, 2H), 3.69 (brs, 2H), 6.04 (m, 3H), 6.83 (m, 1H), 7.42 (brs, 2H), 7.40 (m, 1H), 7.75 (m, 2H), 7.79 (m, 1H)

EXAMPLE 91

Synthesis of (5-amino-3-(2-(trifluoromethyl)phenyl)isoxazol-4-yl)(4-(3,4-dichlorophenyl)piperazine-1-yl)methanone In a similar manner as described in Example 1, by using dichloromethane (30 mL), 5-amino-3-(2-trifluoromethyl)

phenyl)isoxazol-4-carboxylic acid (501 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (633 mg, 1.30 mmol, 71%) was obtained.

$^1$H-NMR (400 MHz, DMSO, δ)=2.72 (brs, 2H), 3.09 (brs (brs, 2H), 3.38 (brs, 2H), 3.76 (brs, 2H), 6.66 (dd, 1H), 6.84 (d, 1H), 7.28 (m, 1H), 7.41 (brs, 2H), 7.40 (m, 1H), 7.73 (m, 2H), 7.78 (m, 1H)

EXAMPLE 92

Synthesis of (5-amino-3-(2-(trifluoromethyl)phenyl) isoxazol-4-yl)(4-(3-methoxyphenyl)piperazine-1-yl) methanone In a similar manner as described in Example 1, by using dichloromethane (30 mL), 5-amino-3-(2-trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (549 mg, 1.23 mmol, 67%) was obtained.

$^1$H-NMR (400 MHz, DMSO, δ)=2.62 (brs, 2H), 3.15 (brs, 2H), 3.33 (brs, 2H), 3.81 (brs, 2H), 3.87 (s, 3H), 6.43 (s, 1H), 6.51 (m, 2H), 7.40 (m, 1H), 7.43 (brs, 2H), 7.44 (dd, 1H), 7.73 (m, 2H), 7.79 (dd, 1H)

EXAMPLE 93

Synthesis of (5-amino-3-(2-(trifluoromethyl)phenyl) isoxazol-4-yl)(4-(2-methoxyphenyl)piperazine-1-yl) methanone In a similar manner as described in Example 1, by using dichloromethane (30 mL), 5-amino-3-(2-trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (473 mg, 1.06 mmol, 58%) was obtained.

$^1$H-NMR (400 MHz, DMSO, δ)=2.61 (brs, 2H), 3.02 (brs, 2H), 3.34 (brs, 2H), 3.75 (brs, 2H), 3.83 (s, 3H), 6.72 (brs, 1H), 6.89 (t, 1H), 6.92 (t, 1H), 7.43 (brs, 2H), 7.44 (m, 1H), 7.65 (dd, 1H), 7.72 (m, 2H), 7.75 (m, 1H)

EXAMPLE 94

Synthesis of 5-amino-3-(2-(trifluoromethyl)phenyl) isoxazol-4-yl)(4-(3-(trifluoromethyl)phenyl)piperazine-1-yl)methanone In a similar manner as described in Example 1, by using dichloromethane (30 mL), 5-amino-3-(2-trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol) and 1-(3-(trifluoromethyl)phenyl) piperazine (424 mg, 1.84 mmol), a white solid required compound (631 mg, 1.30 mmol, 71%) was obtained.

$^1$H-NMR (400 MHz, DMSO, δ)=2.65 (brs, 2H), 3.15 (brs, 4H), 3.37 (brs, 2H), 7.03 (m, 2H), 7.16 (d, 1H), 7.40 (m, 1H), 7.43 (brs, 2H), 7.44 (m, 1H), 7.70 (m, 2H), 7.76 (m, 1H)

EXAMPLE 95

Synthesis of (5-amino-3-(2-(trifluoromethyl)phenyl) isoxazol-4-yl)(4-(4-hydroxyphenyl)piperazine-1-yl) methanone In a similar manner as described in Example 1, by using dimethylformamide (15 mL), 5-amino-3-(2-trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (434 mg, 1.00 mmol, 55%) was obtained.

$^1$H-NMR (400 MHz, DMSO, δ)=2.61 (brs, 2H), 3.04 (brs, 2H), 3.32 (brs, 2H), 3.89 (brs, 2H), 6.79 (m, 4H), 7.38 (m, 1H), 7.46 (brs, 2H), 7.70 (m, 2H), 7.76 (m, 1H)

EXAMPLE 96

Synthesis of 5-amino-3-(2-(trifluoromethyl)phenyl) isoxazol-4-yl)(4-(2-hydroxyphenyl)piperazine-1-yl) methanone In a similar manner as described in Example 1, by using dimethylformamide (15 mL), 5-amino-3-(2-trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (471 mg, 1.09 mmol, 59%) was obtained.

$^1$H-NMR (400 MHz, DMSO, δ)=2.63 (brs, 2H), 3.01 (brs, 2H), 3.35 (brs, 2H), 4.09 (brs, 2H), 6.81 (m, 1H), 7.06 (m, 2H), 7.19 (m, 1H), 7.42 (brs, 2H), 7.48 (m, 1H), 7.73 (m, 2H), 7.78 (m, 1H)

EXAMPLE 97

Synthesis of (5-amino-3-(2-(trifluoromethyl)phenyl) isoxazol-4-yl)(4-(4-fluorophenyl)piperazine-1-yl) methanone In a similar manner as described in Example 1, by using dichloromethane (30 mL), 5-amino-3-(2-(trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (603 mg, 1.39 mmol, 75%) was obtained.

$^1$H-NMR (400 MHz, CDCl$_3$, δ)=2.86 (brs, 4H), 3.47 (brs, 4H), 6.90 (m, 2H), 7.04 (m, 2H), 7.43 (brs, 2H), 7.49 (m, 1H), 7.70 (m, 2H), 7.76 (m, 1H)

EXAMPLE 98

Synthesis of (5-amino-3-(4-(trifluoromethoxy)phenyl)isoxazol-4-yl)(4-(2-fluorophenyl)piperazine-1-yl)methanone In a similar manner as described in Example 1, by using dichloromethane (30 mL), 5-amino-3-(4-(trifluoromethoxy) phenyl)isoxazol-4-carboxylic acid (530 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (533 mg, 1.18 mmol, 64%) was obtained.

¹H-NMR (400 MHz, DMSO, δ)=2.72 (brs, 2H), 3.03 (brs, 2H), 3.43 (brs, 2H), 3.70 (brs, 2H), 6.08 (m, 3H), 6.79 (t, 1H), 7.31 (brs, 2H), 7.38 (d, 2H), 7.44 (d, 2H)

EXAMPLE 99

Synthesis of (5-amino-3-(4-(trifluoromethoxy)phenyl)isoxazol-4-yl)(3,4-dichlorophenyl)piperazine-1-yl)methanone In a similar manner as described in Example 1, by using dichloromethane (30 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (688 mg, 1.37 mmol, 75%) was obtained.

¹H-NMR (400 MHz, DMSO, δ)=2.72 (brs, 2H), 3.03 (brs, 2H), 3.47 (brs, 2H), 3.71 (brs, 2H), 6.64 (dd, 1H), 6.86 (d, 1H), 7.32 (brs, 2H), 7.33 (d, 2H), 7.45 (d, 2H), 7.54 (m, 1H)

EXAMPLE 100

Synthesis of (5-amino-3-(4-(trifluoromethoxy)phenyl)isoxazol-4-yl)(4-(3-methoxyphenyl)piperazine-1-yl)methanone In a similar manner as described in Example 1, by using dichloromethane (30 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (588 mg, 1.27 mmol, 69%) was obtained.

¹H-NMR (400 MHz, DMSO, δ)=2.65 (brs, 2H), 3.12 (brs, 2H), 3.31 (brs, 2H), 3.79 (brs, 2H), 3.81 (s, 3H), 6.40 (brs, 1H), 6.50 (m, 2H), 7.30 (brs, 2H), 7.36 (d, 2H), 7.44 (dd, 1H), 7.49 (d, 2H), 7.77 (dd, 1H)

EXAMPLE 101

Synthesis of (5-amino-3-(4-(trifluoromethoxy)phenyl)isoxazol-4-yl)(4-(2-methoxyphenyl)piperazine-1-yl)methanone In a similar manner as described in Example 1, by using dichloromethane (30 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (603 mg, 1.30 mmol, 71%) was obtained.

¹H-NMR (400 MHz, DMSO, δ)=2.62 (brs, 2H), 2.95 (brs, 2H), 3.31 (brs, 2H), 3.75 (brs, 2H), 3.89 (s, 3H), 6.78 (brs, 1H), 6.86 (t, 1H), 6.91 (t, 1H), 7.32 (brs, 2H), 7.36 (d, 2H), 7.45 (d, 2H), 7.69 (dd, 1H)

EXAMPLE 102

Synthesis of (5-amino-3-(4-(trifluoromethoxy)phenyl)isoxazol-4-yl)(4-(3-(trifluoromethyl)phenyl)piperazine-1-yl)methanone In a similar manner as described in Example 1, by using dichloromethane (30 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (597 mg, 1.19 mmol, 65%) was obtained.

¹H-NMR (400 MHz, DMSO, δ)=2.63 (brs, 2H), 3.12 (brs, 2H), 3.33 (brs, 2H), 7.02 (m, 2H), 7.14 (d, 1H), 7.33 (brs, 2H), 7.38 (d, 2H), 7.45 (m, 1H), 7.46 (d, 2H), 7.58 (m, 1H)

EXAMPLE 103

Synthesis of (5-amino-3-(4-(trifluoromethoxy)phenyl)isoxazol-4-yl)(4-(4-hydroxyphenyl)piperazine-1-yl)methanone In a similar manner as described in Example 1, by using dimethylformimide (15 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (566 mg, 1.26 mmol, 69%) was obtained.

¹H-NMR (400 MHz, DMSO, δ)=2.62 (brs, 2H), 3.29 (brs, 2H), 3.34 (brs, 2H), 3.94 (brs, 2H), 6.71 (m, 4H), 7.33 (brs, 2H), 7.37 (d, 2H), 7.42 (d, 2H)

EXAMPLE 104

Synthesis of (5-amino-3-(4-(trifluoromethoxy)phenyl)isoxazol-4-yl)(4-(2-hydroxyphenyl)piperazine-1-yl)methanone In a similar manner as described in Example 1, by using dimethylformimide (15 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (591 mg, 1.32 mmol, 72%) was obtained.

¹H-NMR (400 MHz, DMSO, δ)=2.63 (brs, 2H), 3.04 (brs, 2H), 3.33 (brs, 2H), 4.03 (brs, 2H), 6.85 (m, 1H), 7.03 (m, 2H), 7.22 (m, 1H), 7.31 (brs, 2H), 7.38 (d, 2H), 7.46 (d, 2H)

EXAMPLE 105

Synthesis of (5-amino-3-(4-(trifluoromethoxy)phenyl)isoxazol-4-yl)(4-(4-fluorophenyl)piperazine-1-yl)methanone In a similar manner as described in Example 1, by using dichloromethane (30 mL), 5-amino-3-(4-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (621 mg, 1.38 mmol, 75%) was obtained.

¹H-NMR (400 MHz, DMSO, δ)=2.83 (brs, 4H), 3.47 (brs, 4H), 6.91 (m, 2H), 7.05 (m, 2H), 7.31 (brs, 2H), 7.36 (d, 2H), 7.46 (d, 2H)

EXAMPLE 106

Synthesis of (5-amino-3-(3-(trifluoromethyl)phenyl)isoxazol-4-yl)(4-(2-fluorophenyl)piperazine-1-yl)methanone In a similar manner as described in Example 1, by using dichloromethane (30 mL), 5-amino-3-(3-trifluoromethyl)

phenyl)isoxazol-4-carboxylic acid (501 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (566 mg, 1.31 mmol, 71%) was obtained.

$^1$H-NMR (400 MHz, DMSO, δ)=2.73 (brs, 2H), 3.02 (brs, 2H), 3.31 (brs, 2H), 3.72 (brs, 2H), 6.14 (m, 3H), 6.87 (m, 1H), 7.29 (m, 1H), 7.49 (brs, 2H), 7.63 (m, 1H), 7.71 (m, 2H)

EXAMPLE 107

Synthesis of (5-amino-3-(3-(trifluoromethyl)phenyl)isoxazol-4-yl)(4-(3,4-dichlorophenyl)piperazine-1-yl)methanone In a similar manner as described in Example 1, by using dichloromethane (30 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (633 mg, 1.30 mmol, 71%) was obtained.

$^1$H-NMR (400 MHz, DMSO, δ)=2.73 (brs, 2H), 3.08 (brs (brs, 2H), 3.35 (brs, 2H), 3.72 (brs, 2H), 6.62 (dd, 1H), 6.84 (d, 1H), 7.24 (m, 1H), 7.31 (m, 1H), 7.44 (brs, 2H), 7.61 (m, 1H), 7.71 (m, 2H)

EXAMPLE 108

Synthesis of (5-amino-3-(3-(trifluoromethyl)phenyl)isoxazol-4-yl)(4-(3-methoxyphenyl)piperazine-1-yl)methanone In a similar manner as described in Example 1, by using dichloromethane (30 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (549 mg, 1.23 mmol, 67%) was obtained.

$^1$H-NMR (400 MHz, DMSO, δ)=2.63 (brs, 2H), 3.18 (brs, 2H), 3.30 (brs, 2H), 3.82 (brs, 2H), 3.85 (s, 3H), 6.39 (s, 1H), 6.48 (m, 2H), 7.29 (m, 1H), 7.37 (m, 1H), 7.40 (brs, 2H), 7.60 (m, 1H), 7.69 (m, 2H)

EXAMPLE 109

Synthesis of (5-amino-3-(3-(trifluoromethyl)phenyl)isoxazol-4-yl)(4-(2-methoxyphenyl)piperazine-1-yl)methanone In a similar manner as described in Example 1, by using dichloromethane (30 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (473 mg, 1.06 mmol, 58%) was obtained.

$^1$H-NMR (400 MHz, DMSO, δ)=2.63 (brs, 2H), 3.12 (brs, 2H), 3.37 (brs, 2H), 3.79 (brs, 2H), 3.81 (s, 3H), 6.74 (brs, 1H), 6.82 (t, 1H), 6.91 (t, 1H), 7.29 (m, 1H), 7.46 (m, 3H), 7.65 (m, 1H), 7.70 (m, 2H)

EXAMPLE 110

Synthesis of (5-amino-3-(3-(trifluoromethyl)phenyl)isoxazol-4-yl)(4-(3-(trifluoromethyl)phenyl)piperazine-1-yl)methanone In a similar manner as described in Example 1, by using dichloromethane (30 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (631 mg, 1.30 mmol, 71%) was obtained.

$^1$H-NMR (400 MHz, DMSO, δ)=2.69 (brs, 2H), 3.14 (brs, 4H), 3.35 (brs, 2H), 7.01 (m, 2H), 7.21 (d, 1H), 7.33 (m, 1H), 7.41 (m, 1H), 7.45 (brs, 2H), 7.63 (m, 1H), 7.70 (m, 2H)

EXAMPLE 111

Synthesis of (5-amino-3-(3-(trifluoromethyl)phenyl)isoxazol-4-yl)(4-(4-hydroxyphenyl)piperazine-1-yl)methanone In a similar manner as described in Example 1, by using dimethylformamide (15 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (460 mg, 106 mmol, 58%) was obtained.

$^1$H-NMR (400 MHz, DMSO, δ)=2.69 (brs, 4H), 3.82 (brs, 4H), 6.72 (m, 4H), 7.32 (m, 1H), 7.46 (brs, 2H), 7.64 (m, 1H), 7.73 (m, 1H)

EXAMPLE 112

Synthesis of (5-amino-3-(3-(trifluoromethyl)phenyl)isoxazol-4-yl)(4-(2-hydroxyphenyl)piperazine-1-yl)methanone In a similar manner as described in Example 1, by using dimethylformamide (15 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (492 mg, 1.14 mmol, 62%) was obtained.

$^1$H-NMR (400 MHz, DMSO, δ)=2.62 (brs, 2H), 3.02 (brs, 2H), 3.32 (brs, 2H), 4.09 (brs, 2H), 6.85 (m, 1H), 7.12 (m, 2H), 7.17 (m, 1H), 7.29 (m, 1H), 7.46 (brs, 2H), 7.63 (m, 1H), 7.71 (m, 2H)

EXAMPLE 113

Synthesis of (5-amino-3-(3-(trifluoromethyl)phenyl)isoxazol-4-yl)(4-(4-fluorophenyl)piperazine-1-yl)methanone In a similar manner as described in Example 1, by using dichloromethane (30 mL), 5-amino-3-(3-trifluoromethyl)phenyl)isoxazol-4-carboxylic acid (501 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (603 mg, 1.39 mmol, 75%) was obtained.

¹H-NMR (400 MHz, CDCl₃, δ)=2.89 (brs, 4H), 3.46 (brs, 4H), 6.91 (m, 2H), 7.05 (m, 2H), 7.31 (m, 1H), 7.47 (brs, 2H), 7.60 (m, 1H), 7.76 (m, 2H)

EXAMPLE 114

Synthesis of (5-amino-3-(3-(trifluoromethoxy)phenyl)isoxazol-4-yl)(4-(2-fluorophenyl)piperazine-1-yl)methanone In a similar manner as described in Example 1, by using dichloromethane (30 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(2-fluorophenyl)piperazine (332 mg, 1.84 mmol), a white solid required compound (538 mg, 1.19 mmol, 65%) was obtained.
¹H-NMR (400 MHz, DMSO, δ)=2.74 (brs, 2H), 3.06 (brs, 2H), 3.41 (brs, 2H), 3.69 (brs, 2H), 6.12 (m, 3H), 6.78 (t, 1H), 7.33 (brs, 2H), 7.36 (m, 2H), 7.53 (m, 1H), 7.69 (m, 1H)

EXAMPLE 115

Synthesis of (5-amino-3-(3-(trifluoromethoxy)phenyl)isoxazol-4-yl)(4-(3,4-dichlorophenyl)piperazine-1-yl)methanone In a similar manner as described in Example 1, by using dichloromethane (30 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3,4-dichlorophenyl)piperazine (425 mg, 1.84 mmol), a white solid required compound (652 mg, 1.31 mmol, 71%) was obtained.
¹H-NMR (400 MHz, DMSO, δ)=2.75 (brs, 2H), 3.09 (brs, 2H), 3.51 (brs, 2H), 3.78 (brs, 2H), 6.60 (dd, 1H), 6.89 (d, 1H), 7.36 (m, 1H), 7.37 (brs, 2H), 7.53 (m, 3H), 7.69 (m, 1H)

EXAMPLE 116

Synthesis of (5-amino-3-(3-(trifluoromethoxy)phenyl)isoxazol-4-yl)(4-(3-methoxyphenyl)piperazine-1-yl)methanone In a similar manner as described in Example 1, by using dichloromethane (30 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3-methoxyphenyl)piperazine (354 mg, 1.84 mmol), a white solid required compound (562 mg, 1.22 mmol, 66%) was obtained.
¹H-NMR (400 MHz, DMSO, δ)=2.63 (brs, 2H), 3.15 (brs, 2H), 3.29 (brs, 2H), 3.82 (brs, 2H), 3.82 (s, 3H), 6.43 (brs, 1H), 6.52 (m, 2H), 7.31 (brs, 2H), 7.36 (m, 2H), 7.51 (m, 1H), 7.70 (m, 1H), 7.77 (dd, 1H)

EXAMPLE 117

Synthesis of (5-amino-3-(3-(trifluoromethoxy)phenyl)isoxazol-4-yl)(4-(2-methoxyphenyl)piperazine-1-yl)methanone In a similar manner as described in Example 1, by using dichloromethane (30 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(2-methoxyphenyl)piperazine (354 mg, 1.84 mmol), a white solid required compound (622 mg, 1.35 mmol, 73%) was obtained.
¹H-NMR (400 MHz, DMSO, δ)=2.60 (brs, 2H), 2.99 (brs, 2H), 3.29 (brs, 2H), 3.74 (brs, 2H), 3.85 (s, 3H), 6.71 (brs, 1H), 6.85 (t, 1H), 6.93 (t, 1H), 7.31 (brs, 2H), 7.36 (m, 2H), 7.53 (m, 1H), 7.65 (m, 1H), 7.69 (dd, 1H)

EXAMPLE 118

Synthesis of (5-amino-3-(3-(trifluoromethoxy)phenyl)isoxazol-4-yl)(4-(3-trifluoromethyl)phenyl)piperazine-1-yl)methanone In a similar manner as described in Example 1, by using dichloromethane (30 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and 1-(3-(trifluoromethyl)phenyl)piperazine (424 mg, 1.84 mmol), a white solid required compound (542 mg, 1.19 mmol, 59%) was obtained.
¹H-NMR (400 MHz, DMSO, δ)=2.60 (brs, 2H), 3.10 (brs, 2H), 3.35 (brs, 2H), 7.01 (m, 2H), 7.15 (d, 1H), 7.31 (brs, 2H), 7.36 (m, 2H), 7.43 (m, 1H), 7.51 (m, 1H), 7.53 (m, 1H), 7.65 (m, 1H)

EXAMPLE 119

Synthesis of (5-amino-3-(3-(trifluoromethoxy)phenyl)isoxazol-4-yl)(4-(4-hydroxyphenyl)piperazine-1-yl)methanone In a similar manner as described in Example 1, by using dimethylformimide (15 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 4-(piperazine-1-yl)phenol (328 mg, 1.84 mmol), a white solid required compound (601 mg, 1.34 mmol, 72%) was obtained.
¹H-NMR (400 MHz, DMSO, δ)=2.61 (brs, 2H), 3.31 (brs, 2H), 3.32 (brs, 2H), 3.95 (brs, 2H), 6.69 (m, 4H), 7.31 (brs, 2H), 7.38 (m, 2H), 7.52 (m, 1H), 7.72 (m, 1H)

EXAMPLE 120

Synthesis of (5-amino-3-(3-(trifluoromethoxy)phenyl)isoxazol-4-yl)(4-(2-hydroxyphenyl)piperazine-1-yl)methanone In a similar manner as described in Example 1, by using dimethylformimide (15 mL), 5-amino-3-(3-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol), hydroxybenzotriazole (299 mg, 2.21 mmol) and 2-(piperazine-1-yl)phenol (328 mg, 1.84 mmol), a white solid required compound (588 mg, 1.31 mmol, 71%) was obtained.
¹H-NMR (400 MHz, DMSO, δ)=2.61 (brs, 2H), 3.06 (brs, 2H), 3.31 (brs, 2H), 4.02 (brs, 2H), 6.84 (m, 1H), 7.01 (m, 2H), 7.23 (m, 1H), 7.31 (brs, 2H), 7.38 (m, 2H), 7.54 (m, 1H), 7.66 (m, 1H)

EXAMPLE 121

Synthesis of (5-amino-3-(3-(trifluoromethoxy)phenyl)isoxazol-4-yl)(4-(4-fluorophenyl)piperazine-1-yl)methanone In a similar manner as described in Example 1, by using dichloromethane (30 mL), 5-amino-3-(3-(trifluoromethoxy)

phenyl)isoxazol-4-carboxylic acid (530 mg, 1.84 mmol), 1-ethyl-3-(dimethylaminopropyl)carbodiimide hydrochloride (388 mg, 2.02 mmol) and 1-(4-fluorophenyl)piperazine (332 mg, 1.84 mmol), a white solid required compound (609 mg, 1.35 mmol, 73%) was obtained.

$^1$H-NMR (400 MHz, DMSO, δ)=2.81 (brs, 4H), 3.45 (brs, 4H), 6.92 (m, 2H), 7.09 (m, 2H), 7.34 (brs, 2H), 7.39 (m, 2H), 7.51 (m, 1H), 7.68 (m, 1H)

EXAMPLE 122

Synthesis of ethyl-1-(5-amino-3-(2-chlorophenyl) isoxazol-4-carbonyl)piperidine-4-carboxylate In a similar manner as described in Example 1, by using dichloromethane (30 mL), 5-amino-3-(2-chlorophenyl)isoxazol-4-carboxylic acid (439 mg, 1.84 mmol), 1-ethyl-3-(dimethylaminopropyl)carbodiimide hydrochloride (388 mg, 2.02 mmol) and ethyl piperazine-4-carboxylate (289 mg, 1.84 mmol), a white solid required compound (422 mg, 1.12 mmol, 60%) was obtained.

$^1$H-NMR (400 MHz, CDCl$_3$, δ)=1.14 (m, 5H), 1.66 (m, 2H), 2.51 (m, 1H), 2.81 (q, 2H), 3.76 (d, 2H), 4.05 (q, 2H), 7.25 (s, 2H), 7.46 (m, 3H), 7.57 (m, 1H)

EXAMPLE 123

Synthesis of methyl-1-(5-amino-3-(2-fluorophenyl) isoxazol-4-carbonyl)piperidine-4-carboxylate In a similar manner as described in Example 1, by using dichloromethane (30 mL), 5-amino-3-(2-fluorophenyl)isoxazol-4-carboxylic acid (409 mg, 1.84 mmol), 1-ethyl-3-(dimethylaminopropyl)carbodiimide hydrochloride (388 mg, 2.02 mmol) and methyl piperazine-4-carboxylate (263 mg, 1.84 mmol), a white solid required compound (463 mg, 1.33 mmol, 72%) was obtained.

$^1$H-NMR (400 MHz, CDCl$_3$, δ)=1.58 (m, 2H), 1.81 (m, 2H), 2.03 (m, 2H), 2.29 (m, 1H), 7.76 (m, 2H), 3.71 (s, 3H), 7.26 (m, 1H), 7.45 (m, 1H), 7.64 (m, 2H)

EXAMPLE 124

Synthesis of ethyl-1-(5-amino-3-(2-trifluoromethoxy)phenyl)isoxazol-4-carbonyl)piperidine-4-carboxylate In a similar manner as described in Example 1, by using dichloromethane (30 mL), 5-amino-3-(2-(trifluoromethoxy)phenyl)isoxazol-4-carboxylic acid (530 mg, 1.84 mmol), 1-ethyl-3-(dimethylaminopropyl)carbodiimide hydrochloride (388 mg, 2.02 mmol) and ethyl piperazine-4-carboxylate (289 mg, 1.84 mmol), a white solid required compound (429 mg, 1.00 mmol, 55%) was obtained.

$^1$H-NMR (400 MHz, CDCl$_3$, δ)=1.16 (m, 5H), 1.65 (m, 2H), 2.54 (m, 1H), 2.83 (q, 2H), 3.74 (d, 2H), 4.06 (q, 2H), 7.41, (brs, 2H), 7.45 (m, 3H), 7.59 (m, 1H)

EXAMPLE 125

Synthesis of ethyl-1-(5-amino-3-(2-trifluoromethyl) phenyl)isoxazol-4-carbonyl)piperidine-4-carboxylate In a similar manner as described in Example 1, by using dichloromethane (30 mL), 5-amino-3-(2-(trifluoromethyl) phenyl)isoxazol-4-carboxylic acid (501 mg, 1.84 mmol), 1-ethyl-3-(dimethylaminopropyl)carbodiimide hydrochloride (388 mg, 2.02 mmol) and ethyl piperazine-4-carboxylate (289 mg, 1.84 mmol), a white solid required compound (495 mg, 1.20 mmol, 65%) was obtained.

$^1$H-NMR (400 MHz, CDCl$_3$, δ)=1.13 (m, 5H), 1.62 (m, 2H), 2.49 (m, 1H), 2.76 (q, 2H), 3.74 (d, 2H), 4.09 (q, 2H), 7.41 (m, 1H), 7.43 (brs, 2H), 7.78 (m, 2H), 7.81 (m, 1H)

EXAMPLE 126

Synthesis of (4-(3,4-dichlorophenyl)piperazine-1-yl) (5-methyl-3-(2-(trifluoromethoxy)phenyl)isoxazol-4-yl)methanone hydrochloric acid (4-(3,4-dichlorophenyl)piperazine-1-yl)(5-methyl-3-(2-(trifluoromethoxy)phenyl)isoxazol-4-yl)methanone (100 mg, 0.20 mmol) was dissolved in acetone (10 mL), cooled to 0° C. and slowly added with hydrochloric ethanol (10%, 73 mg, 0.20 mmol). The resultant product was stirred at room temperature for 8 hours, filtered, and dried so as to provide a white solid required compound (84 mg, 1.20 mmol, 78%).

$^1$H-NMR (400 MHz, DMSO, δ)=2.55 (s, 3H), 2.78 (brs, 2H), 3.14 (brs, 2H), 3.28 (brs, 2H), 3.58 (brs, 2H), 6.88 (dd, 1H), 7.10 (d, 1H), 7.40 (d, 1H), 7.56 (m, 2H), 7.68 (m, 2H)

EXAMPLE 127

Synthesis of (3-(2-chlorophenyl)-5-methylisoxazol-4-yl)(4-(3-methoxyphenyl)piperazine-1-yl)methanone hydrochloric acid In a similar manner as described in Example 126, by using acetone (10 mL), 3-(2-chlorophenyl)-5-methylisoxazol-4-yl)(4-(3-methoxyphenyl)piperazine-1-yl)methanone (82 mg, 0.20 mmol) and hydrochloric ethanol (10%, 73 mg, 0.20 mmol), a white solid required compound (58 mg, 0.13, 65%) was obtained.

$^1$H-NMR (400 MHz, DMSO, δ)=2.56 (s, 3H), 2.74 (brs, 2H), 3.06 (brs, 2H), 3.53 (brs, 2H), 3.72 (brs, 2H), 3.74 (s, 3H), 6.66 (m, 1H), 7.12 (m, 2H), 7.52 (m, 4H), 7.66 (m, 1H)

EXAMPLE 128

Synthesis of ethyl-1-(5-methyl-3-(2-(trifluoromethoxy)phenyl)isoxazol-4-carbomyl)piperazine-4-carboxylate hydrochloric acid In a similar manner as described in Example 126, by using acetone (10 mL), ethyl-1-(5-methyl-3-(2-(trifluoromethoxy) phenyl)isoxazol-4-carbomyl)piperazine-4-carboxylate (85 mg, 0.20 mmol) and hydrochloric ethanol (10%, 73 mg, 0.20 mmol), a white solid required compound (64 mg, 0.14 mmol, 69%) was obtained.

$^1$H-NMR (400 MHz, DMSO, δ)=1.18 (m, 5H), 1.70 (m, 2H), 2.53 (m, 1H), 2.82 (q, 2H), 3.70 (d, 2H), 4.18 (q, 2H), 7.42 (m, 3H), 7.63 (brs, 2H), 7.72 (m, 1H)

EXAMPLE 129

Synthesis of (4-(2-methoxyphenyl)piperazine-1-yl) (5-methyl-3-(2-(trifluoromethyl)phenyl)isoxazol-4-yl)methanone hydrochloric acid In a similar manner as described in Example 126, by using acetone (10 mL), (4-(2-methoxyphenyl)piperazine-1-yl)(5-methyl-3-(2-(trifluoromethyl)phenyl)isoxazol-4-yl)methanone (90 mg, 0.20 mmol) and hydrochloric ethanol (10%, 73 mg, 0.20 mmol), a white solid required compound (53 mg, 0.11 mmol, 55%) was obtained.

¹H-NMR (400 MHz, DMSO, δ)=2.36 (brs, 2H), 2.57 (s, 3H), 2.87 (brs, 2H), 3.31 (brs, 2H), 3.74 (brs, 2H), 3.82 (s, 3H), 6.39 (m, 2H), 7.12 (m, 2H), 7.71 (m, 2H), 7.87 (m, 1H)

EXAMPLE 130

Synthesis of (3-(3-fluorophenyl)-5-methylisoxazol-4-yl)(4-(2-hydroxyphenyl)piperazine-1-yl)methanone hydrochloric acid In a similar manner as described in Example 126, by using acetone (10 mL), 3-(3-fluorophenyl)-5-methylisoxazol-4-yl)(4-(2-hydroxyphenyl)piperazine-1-yl)methanone (76 mg, 0.20 mmol) and hydrochloric ethanol (10%, 73 mg, 0.20 mmol), a white solid required compound (48 mg, 0.12 mmol, 57%) was obtained.

¹H-NMR (400 MHz, DMSO, δ)=2.48 (brs, 2H), 2.53 (s, 3H), 2.86 (brs, 2H), 3.17 (brs, 2H), 3.84 (brs, 2H), 7.24 (m, 3H), 7.42 (m, 3H), 7.56 (m, 2H)

EXAMPLE 131

Synthesis of (5-amino-3-(2-chlorophenyl)isoxazol-4-yl)(4-(3-methoxyphenyl)piperazine-1-yl)methanone hydrochloric acid In a similar manner as described in Example 126, by using acetone (10 mL), (5-amino-3-(2-chlorophenyl)isoxazol-4-yl)(4-(3-methoxyphenyl)piperazine-1-yl)methanone (83 mg, 0.20 mmol) and hydrochloric ethanol (10%, 73 mg, 0.20 mmol), a white solid required compound (63 mg, 0.14 mmol, 70%) was obtained.

¹H-NMR (400 MHz, DMSO, δ)=2.58 (brs, 4H), 3.29 (brs, 2H), 3.53 (brs, 2H), 3.66 (s, 3H), 6.49 (m, 2H), 6.58 (m, 1H), 7.24 (m, 1H), 7.62 (s, 2H), 7.66 (m, 4H)

EXPERIMENTAL EXAMPLE 1

Reduction Assay Using GFP Expression Influenza Virus

Acell (MDCK) was infected with an influenza virus (K09) expressing GFP (Green fluorescence protein) for 1 hour, and cultured in a medium added with a compound with different concentrations. After 24 to 72 hours, through a fluorescent microscope, a GFP signal was observed. Then, a cell not treated with a virus and a compound at all, and a cell only infected with an influenza virus were used as control groups. If the compound has an antiviral effect, it can be observed that the GFP signal is decreased according to an increase of the concentration of the compound.

EXPERIMENTAL EXAMPLE 2

Virucidal Assay by Plaque Reduction Assay

In this experiment, before a cell is infected with a virus, the virus is directly treated with a compound so as to determine if the compound has an effect on the inhibition of the intracellular penetration of the influenza virus. For this, first, a compound with different concentrations was reacted with an influenza virus at room temperature for 1 hour. Then, an MDCK cell was infected with the virus for 1 hour, washed with PBS, and cultured in a medium including 2% oxoid agar. After 72 hours, the cell was dyed with crystal violet. Then, it was observed if a plaque was formed. At the positions added with the compound with different concentrations, the number and size of plaques were compared to those in the control groups. Then, through analysis of antiviral activity, EC50 was determined.

EXPERIMENTAL EXAMPLE 3

Cytotoxicity Assay Using MTT (3-(4,5-dimethylthiazol-2-yl)-2,5-diphenyl-2H-tetrazolium bromide)

In this experiment, a cell was infected with a virus, and then the virus was directly treated with a compound so as to determine if the virus-infected cell has toxicity. For this, a cell (MDCK) was infected with an influenza virus (K09) for 1 hour, and treated with the compound with different concentrations for 24 hours. Then, the cell was treated with a MTT reagent for 1 hour. After 1 hour, a formazan crystal produced by the MTT reagent was dissolved in DMSO, and the absorbance was measured by an ELISA reader so as to determine CC50.

The antiviral efficacy test of the inventive compound was carried out on compounds according to Examples of this specification through Experimental Example 1 to Experimental Example 3. As a result, it was found that the inventive compound has a Formula structure having antiviral activity.

From among compounds according to Examples of this specification, about 30 compounds were determined through reduction assay to show antiviral activity after intracellular infection of a virus.

These compounds were subjected to MTT assay, and reduction assay, and EC50, CC50, and SI (Selective index) values were measured. The results are noted in Table 1 below.

1) EC50 (Effective Concentration 50%):
measured by reduction assay. A minimum concentration of the compound, at which the number of plaques is reduced to half or more compared to that of a control group 2) CC50 (Cytotoxicity concentration 50%):
measured by MTT assay. A maximum concentration of the compound, at which the number of cells is reduced to half or more compared to that of a control group 3) SI (Selective Index): value indicated by CC50/EC50

TABLE 1

| | | Reduction assay result | | | |
| --- | --- | --- | --- | --- | --- |
| | | GFP reduction (Experimental Example 1) effect | Plaque reduction (Experimental Example 2) EC50 (µg/ml) | MTT assay (Experimental Example 3) CC50 (µg/ml) | SI value K09 |
| Control | Oseltamivir | X | 0.3905 | 625 to 1250 | 1600.51 to 3201.024 |
| 1 | Example 3 | ○ | 0.33 to 0.65 | 308 to 628 | 473.84 to 1903.03 |
| 2 | Example 4 | ○ | 12.5 to 25 | 78.12 to 156.25 | 3.125 to 12.5 |

TABLE 1-continued

|  |  | Reduction assay result | | MTT assay (Experimental Example 3) CC50 (µg/ml) | SI value K09 |
|---|---|---|---|---|---|
|  |  | GFP reduction (Experimental Example 1) effect | Plaque reduction (Experimental Example 2) EC50 (µg/ml) | | |
| 3 | Example 9 | ○ | 0.195 to 0.39 | 312.5 to 625 | 801.282 to 3205.128 |
| 4 | Example 11 | ○ | <0.16 | 287 to 625 | >1793 or >3906 |
| 5 | Example 12 | ○ | 3.125 | 78.125 to 156.25 | 25 to 50 |
| 6 | Example 16 | ○ | 0.39 | 78.12 | 200.321 |
| 7 | Example 27 | ○ | 2.4 to 3.9 | 9.77 to 19.53 | 2.5 to 8.13 |
| 8 | Example 35 | ○ | 0.395 to 0.781 | 312.5 to 625 | 400.128 to 1582.278 |
| 9 | Example 36 | ○ | 1.56 | 500< | 320< |
| 10 | Example 43 | X | X | 2500 | X |
| 11 | Example 51 | ○ | 2.4 to 3.9 | 15.25 to 25.92 | 3.91 to 10.80 |
| 12 | Example 53 | ○ | 3.12 | 500< | 160< |
| 13 | Example 60 | ○ | 0.1952 | 500< | 2560.82< |
| 14 | Example 61 | ○ | 0.39 | 62.5 to 125 | 159.94 to 319.89 |
| 15 | Example 67 | ○ | 2.4 to 3.9 | 10.12 to 21.25 | 2.59 to 8.85 |
| 16 | Example 68 | ○ | 17.5 to 29 | 88.12 to 136.75 | 3.03 to 7.81 |
| 17 | Example 72 | ○ | 25 to 50 | 15.62 to 31.25 | 0.31 to 1.25 |
| 18 | Example 75 | ○ | 50< | 625 to 1250 | 12.5 to 25.0 |
| 19 | Example 83 | ○ | 0.65 to 1.5 | 150.3 to 189.64 | 100.2 to 291.75 |
| 20 | Example 91 | ○ | 12.45 to 25.80 | 18.35 to 29.87 | 0.71 to 2.39 |
| 21 | Example 92 | ○ | 21 to 45 | 14.62 to 33.52 | 0.32 to 1.59 |
| 22 | Example 99 | ○ | 21 to 45 | 14.62 to 33.52 | 0.32 to 1.59 |
| 23 | Example 100 | ○ | 29 to 37 | 18.45 to 46.53 | 0.49 to 12.57 |
| 24 | Example 107 | ○ | 2.72 to 3.9 | 122.25 to 170.50 | 31.34 to 62.68 |
| 25 | Example 109 | ○ | 1.52 to 3.5 | 147.25 to 190.64 | 42.07 to 125.4 |
| 26 | Example 112 | ○ | 25 to 50 | 16.5 to 34.27 | 0.33 to 1.37 |
| 27 | Example 115 | ○ | 21 to 45 | 15.5 to 35.75 | 0.34 to 1.70 |
| 28 | Example 116 | ○ | 15 to 32 | 13.65 to 25.64 | 0.42 to 1.70 |
| 29 | Example 122 | ○ | 4.5 to 8.5 | 160.59 to 320.75 | 18.89 to 71.27 |
| 30 | Example 124 | ○ | 3.125 to 6.25 | 312.5 | 50 to 100 |

* ○ = effective, X = ineffective.

From among the compounds according to Examples of this specification, some compounds showing a high antiviral activity effect, from Example 3, Example 4, Example 9, Example 11, Example 12, Example 16, Example 35, Example 60 and Example 124, were subjected to antiviral drug efficacy assay of novel influenza virus (K09 and B/Field), H1N1 influenza virus (solomon) and Oseltamivir resistant strain virus, according to the method of Experimental Examples 2 and 3. The results are noted in Table 2 below.

TABLE 2

|  | EC50 (µg/ml) | CC50 (µg/ml) | SI value |
|---|---|---|---|
| Oseltamivir | | | |
| K09 | 0.3905 | 625 to 1250 | 1600.512 to 3201.024 |
| B/Field | 6.25 | | 200 to 100 |
| Solomon | 3.125 to 6.25 | | 100 to 400 |
| Oseltamivir resistant strain | 50 | | 12.5 to 25 |
| Example 3 | | | |
| K09 | 0.33 to 0.65 | 308 to 628 | 473.84 to 1903.03 |
| B/Field | 50< | | 6.16> or 12.56> |
| Solomon | 0.064 to 0.094 | | 3276.59 to 9812.50 |
| Oseltamivir resistant strain | 0.064 to 0.094 | | 3276.59 to 9812.50 |
| Example 4 | | | |
| K09 | 12.5 to 25 | 78.125 to 156.25 | 3.125 to 12.5 |
| B/Field | 50< | | 1.563> |
| Solomon | 12.5 | | 6.25 to 12.5 |
| Oseltamivir resistant strain | 50 | | 1.563 to 3.125 |
| Example 9 | | | |
| K09 | 0.195 to 0.39 | 312.5 to 625 | 801.282 to 3205.128 |
| B/Field | 50< | | 6.25> or 12.5> |
| Solomon | 0.048 to 0.097 | | 3221.649 to 13020.833 |

TABLE 2-continued

| | EC50 (μg/ml) | CC50 (μg/ml) | SI value |
|---|---|---|---|
| Oseltamivir resistant strain Example 11 | 0.048 to 0.097 | | 3221.649 to 13020.833 |
| K09 | <0.16 | 287 to 625 | >1793 or >3906 |
| B/Field | 4.25 | | 67.529 to 147.058 |
| Solomon | 0.087 to 0.199 | | 1442.211 to 7183.908 |
| Oseltamivir resistant strain Example 12 | 0.195 | | 1471.794 to 3205.128 |
| K09 | 3.125 | 78.125 to 156.25 | 25 to 50 |
| B/Field | 50< | | 1.563>or 3.125> |
| Solomon | 0.781 | | 100.032 to 200.064 |
| Oseltamivir resistant strain Example 16 | 1.562 | | 50.016 to 100.032 |
| K09 | 0.39 | 78.125 | 200.321 |
| B/Field | 25 | | 3.125 |
| Solomon | 0.097 to 0.195 | | 400.641 to 805.412 |
| Oseltamivir resistant strain Example 35 | 0.39 to 0.781 | | 100.032 to 200.321 |
| K09 | 0.395 to 0.781 | 312.5 to 625 | 400.128 to 1582.278 |
| B/Field | 6.25 | | 50 to 100 |
| Solomon | 0.097 to 0.195 | | 1602.564 to 6443.298 |
| Oseltamivir resistant strain Example 60 | 0.195 | | 1602.564 to 3205.128 |
| K09 | 0.1952 | 500< | 2560.82< |
| B/Field | 6.25 | | 80< |
| Solomon | 0.053 to 0.094 | | 5319.148< or 9433.962< |
| Oseltamivir resistant strain Example 124 | 0.053 to 0.094 | | 5319.148< or 9433.962< |
| K09 | 3.125 to 6.25 | 312.5 | 50 to 100 |
| B/Field | 50< | | 6.25> |
| Solomon | 6.25 | | 50 |
| Oseltamivir resistant strain | 25 | | 12.5 |

As noted in Table 1, it can be seen from the results that the SI value obtained by EC50 and CC50 was the highest in the compounds from Example 11, Example 35 and Example 60. Especially, most of the compounds according to Examples of this specification showed a high effect in inhibition of propagation of an intracellular infected virus.

At present, Oseltamivir (tamiflu) and Zanamivir (relenza) used as an influenza virus therapeutic agent are drugs which inhibit Neuraminidase related to the release of an influenza virus, thereby inhibiting movement of the virus to non-infected cells. Also, as other therapeutic agents, M2 ion channel inhibitors of an influenza virus such as Amantadine and Rimantadine are used. However, at present, from some research results, it has been reported that a mutant influenza virus resistant to Oseltamivir was discovered. This is because the influenza virus is an RNA virus that can be more easily mutated than DNA viruses. Accordingly, as advents and side effects of a virus resistant to Oseltamivir have increased, it is urgently required to develop an effective novel influenza virus therapeutic agent.

Accordingly, compounds showing a high antiviral activity effect on a virus strain resistant to Oseltamivir (tamiflu), from Example 3, Example 4, Example 9, Example 11, Example 12, Example 16, Example 35, Example 60, and Example 124, and their derivatives are very useful drugs in the development of an effective novel influenza virus therapeutic agent.

EXPERIMENTAL EXAMPLE 4

An Acute Toxicity Test Through Oral Administration in a Rat

The acute toxicity of the inventive compound was determined through oral administration in a rat. Since the compound is expected to be orally administered in a clinical situation, an oral administration route was selected. A male rat aged 6 weeks (SD-Rat, 220±30 g) was subjected to quarantine, and acclimated for 1 week under a condition of lighting of 12 hours (08:00~20:00), and luminance of 150-300 Lux at 22±3° C. at a relative humidity of 50±20%, while being freely fed with feed and water. Each of a control group and an experimental group include 8 rats. The control group was orally administered with 0.5% HPMC, and the experimental group was orally administered with a material (different concentrations) suspended in 0.5% HPMC, by using a sonde in an amount in proportion to the measured weight of each individual.

The concentration of the drug administered to the experimental group was set as 2000 mg/kg (the highest concentration for a single dose administration in a non-clinical test), and 1000 mg/kg, and 500 mg/kg (with a common ratio). For 14 days from drug administration, clinical symptoms were observed while the weight change was measured. Test animals that died during the test were subjected to autopsy, and abnormalities of main organs (heart, liver, lung, spleen, kidney, and large intestine) were observed and recorded. On the last day of the test (on the 14th day from the administration), all individuals were subjected to autopsy, and the changes of the organs caused by a test material were observed and compared to those in the control group. In the control group, no rats had died, and abnormalities were not observed through autopsy.

Each group was orally administered in a concentration of 500 mg/kg, 1000 mg/kg, and 2000 mg/kg. For 14 days from the administration, according to the test method, clinical symptoms were observed. On the last day of the test (on the 14th day from the administration), changes of the organs were observed with a naked eye through autopsy. The control group, and experimental groups administered with 500 mg/kg, 1000 mg/kg, and 2000 mg/kg did not show any premonitory symptoms right after administration. Also, in the groups administered in various amounts, no individuals died. Also, all administration groups showed a similar weight increase ratio irrespective of the amount of a drug during the observation period. Further, no abnormal responses were observed, and from the autopsy results, no peculiarities were observed. The results of this experiment are noted in Table 3, from which it was found that the compounds of Examples have an LD50 value of 2000 mg/kg or more in oral administration. From this result, it can be determined that the inventive compound is a safe material in view of acute toxicity.

TABLE 3

|  | Example No. | LD50 |
| --- | --- | --- |
| Control | Oseltamivir | 2,000< |
| 1 | 3 | 2,000< |
| 2 | 4 | 2,000< |
| 3 | 9 | 2,000< |
| 4 | 11 | 2,000< |
| 5 | 12 | 2,000< |
| 6 | 16 | 2,000< |
| 7 | 27 | 2,000< |
| 8 | 35 | 2,000< |
| 9 | 60 | 2,000< |
| 10 | 61 | 2,000< |
| 11 | 83 | 2,000< |
| 12 | 107 | 2,000< |
| 13 | 109 | 2,000< |
| 14 | 122 | 2,000< |
| 15 | 124 | 2,000< |

INDUSTRIAL APPLICABILITY

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:
1. A compound or a pharmaceutically acceptable salt, hydrate, solvate, or an acetate, formate or benzoate ester thereof, selected from among: (4-(2-fluorophenyl)-piperazine-1-yl)(5-methyl-3-(2-(trifluoromethyl)-phenyl)isoxazol-4-yl)methanone, (4-(3,4-dichlorophenyl)piperazine-1-yl)(5-methyl-3-(2-(trifluoromethyl)-phenyl)isoxazol-4-yl) methanone, (4-(3-methoxyphenyl)piperazine-1-yl)(5-methyl-3-(2-(trifluoromethyl)-phenyl)isoxazol-4-yl) methanone, (4-(2-methoxyphenyl)-piperazine-1-yl)(5-methyl-3-(2-trifluoromethyl)phenyl)isoxazol-4-yl) methanone, (5-methyl-3-(2-(trifluoromethyl)-phenyl)isoxazol-4-yl)(4-(3-(trifluoromethyl)phenyl)piperazine-1-yl)-methanone, (4-(4-hydroxyphenyl)piperazine-1-yl)(5-methyl-3-(2-(trifluoromethyl)phenyl)-isoxazol-4-yl) methanone, (4-(2-hydroxyphenyl)piperazine-1-yl)(5-methyl-3-(2-(trifluoro-methyl)-phenyl)isoxazol-4-yl) methanone, (4-(4-fluorophenyl)piperazine-1-yl)(5-methyl-3-(2-trifluoromethyl)phenyl)isoxazol-4-yl)methanone, (3-(2-chlorophenyl)-5-methylisoxazol-4-yl)(4-(3-methoxyphenyl)piperazine-1-yl)methanone, (3-(3-fluorophenyl)-5-methylisoxazol-4-yl)(4-(2-fluorophenyl) piperazine-1-yl)methanone, (4-(3,4-dichlorophenyl) piperazine-1-yl)(3-(3-fluorophenyl)-5-methylisoxazol-4-yl) methanone, (3-(3-fluorophenyl)-5-methylisoxazol-4-yl)(4-(3-methoxyphenyl)piperazine-1-yl)methanone, (3-(3-fluorophenyl)-5-methylisoxazol-4-yl)(4-(2-methoxyphenyl) piperazine-1-yl)methanone, (3-(3-fluorophenyl)-5-methylisoxazol-4-yl)(4-(3-(trifluoromethyl)phenyl) piperazine-1-yl)methanone, (3-(3-fluorophenyl)-5-methyl-isoxazol-4-yl)(4-(4-hydroxyphenyl)piperazine-1-yl) methanone, (3-(3-fluorophenyl)-5-methylisoxazol-4-yl)(4-(2-hydroxyphenyl)piperazine-1-yl)methanone, (3-(3-fluorophenyl)-5-methylisoxazol-4-yl)(4-(4-fluorophenyl) piperazine-1-yl)methanone, (3-(2-fluorophenyl)-5-methylisoxazol-4-yl)(4-(2-fluorophenyl)piperazine-1-yl) methanone, (4-(3,4-dichlorophenyl)-piperazine-1-yl)(3-(2-fluorophenyl)-5-methylisoxazol-4-yl)methanone, (3-(2-fluorophenyl)-5-methylisoxazol-4-yl)(4-(3-methoxyphenyl) piperazine-1-yl)methanone, (3-(2-fluorophenyl)-5-methylisoxazol-4-yl)(4-(2-methoxyphenyl)piperazine-1-yl) methanone, (3-(2-fluorophenyl)-5-methylisoxazol-4-yl)(4-(3-(trifluoromethyl)phenyl)piperazine-1-yl)methanone, (3-(2-fluoro-phenyl)-5-methylisoxazol-4-yl)(4-(4-hydroxyphenyl)piperazine-1-yl)methanone, (3-(2-fluoro-phenyl)-5-methylisoxazol-4-yl)(4-(2-hydroxyphenyl) piperazine-1-yl)methanone, (3-(2-fluoro-phenyl)-5-methylisoxazol-4-yl)(4-(4-fluorophenyl)piperazine-1-yl) methanone, (4-(2-fluoro-phenyl)piperazine-1-yl)(5-methyl-3-(4-(trifluoromethoxy)phenyl)isoxazol-4-yl)-methanone, (4-(3,4-dichlorophenyl)piperazine-1-yl)(5-methyl-3-(4-(trifluoromethoxy)-phenyl)isoxazol-4-yl)methanone, (4-(3-methoxyphenyl)piperazine-1-yl)(5-methyl-3-(4-(trifluoromethoxy)-phenyl)isoxazol-4-yl)methanone, (4-(2-methoxyphenyl)piperazine-1-yl)(5-methyl-3-(4-(trifluoromethoxy)phenyl)isoxazol-4-yl)methanone, (5-methyl-3-(4-(trifluoromethoxy)-phenyl)isoxazol-4-yl)(4-(3-(trifluoromethyl)phenyl)piperazine-1-yl)methanone, (4-(4-hydroxyphenyl)piperazine-1-yl)(5-methyl-3-(4-(trifluoromethoxy)phenyl)isoxazol-4-yl)-methanone, (4-(2-hydroxyphenyl)piperazine-1-yl)(5-methyl-3-(4-(trifluoromethoxy)-phenyl)isoxazol-4-yl)methanone, (4-(4-fluorophenyl)piperazine-1-yl)(5-methyl-3-(4-trifluoromethoxy)phenyl)isoxazol-4-yl)methanone, (4-(2-fluorophenyl)piperazine-1-yl)(5-methyl-3-(2-(trifluoromethoxy)phenyl)isoxazol-4-yl)methanone, (4-(3,4-dichlorophenyl)-piperazine-1-yl)(5-methyl-3-(2-(trifluoromethoxy)phenyl)isoxazol-4-yl)methanone, (4-(3-methoxyphenyl)piperazine-1-yl)(5-methyl-3-(2-(trifluoromethoxy)phenyl)isoxazol-4-yl)-methanone, (4-(2-methoxyphenyl)piperazine-1-yl)(5-methyl-3-(2-trifluoromethoxy)-phenyl)isoxazol-4-yl)methanone, (5-methyl-3-(2-(trifluoromethoxy)phenyl)isoxazol-4-yl)(4-(3-(trifluoromethyl)phenyl)piperazine-1-yl)methanone, (4-(4-hydroxyphenyl)piperazine-1-yl)(5-methyl-3-(2-(trifluoromethoxy)phenyl)isoxazol-4-yl)methanone, (4-(2-hydroxyphenyl)-piperazine-1-yl)(5-methyl-3-(2-(trifluoromethoxy)phenyl)isoxazol-4-yl)methanone, (4-(4- fluorophenyl)piperazine-1-yl)(5-methyl-3-(2-(trifluoromethoxy)phenyl)isoxazol-4-yl)-methanone, (4-(2-fluorophenyl)piperazine-1-yl)(5-methyl-3-(3-(trifluoromethyl)phenyl)-isoxazol-4-yl)methanone, (4-(3,4-dichlorophenyl)piperazine-1-yl)(5-methyl-3-(3-(trifluoromethyl)phenyl)isoxazol-4-yl)methanone, (4-(3-methoxyphenyl)piperazine-1-yl)(5-methyl-3-(3-(trifluoromethyl)phenyl)isoxazol-4-yl)methanone, (4-(2-methoxyphenyl)piperazine-1-yl)-(5-methyl-3-(3-(trifluoromethyl)phenyl)isoxazol-4-yl)methanone, (5-methyl-3-(3-trifluoro-methyl)phenyl)isoxazol-4-yl)(4-(3-(trifluoromethyl)phenyl)piperazine-1-yl)-methanone, (4-(4-hydroxyphenyl)piperazine-1-yl)(5-methyl-3-(3-(trifluoromethyl)phenyl)-isoxazol-4-yl)methanone, (4-(2-hydroxyphenyl)piperazine-1-yl)(5-methyl-3-(3-(trifluoromethyl)-phenyl)isoxazol-4-yl)methanone, (4-(4-fluorophenyl)piperazine-1-yl)(5-methyl-3-(3-(trifluoromethyl)phenyl)isoxazol-4-yl)methanone, (4-(2-fluorophenyl)piperazine-1-yl)(5-methyl-3-(3-(trifluoromethoxy)phenyl)isoxazol-4-yl)methanone, (4-(3,4-dichlorophenyl)-piperazine-1-yl)(5-methyl-3-(3-(trifluoromethoxy)phenyl)isoxazol-4-yl)methanone, (4-(3-methoxyphenyl)piperazine-1-yl)(5-methyl-3-(3-(trifluoromethoxy)phenyl)isoxazol-4-yl)-methanone, (4-(2-methoxyphenyl)piperazine-1-yl)(5-methyl-3-(3-(trifluoromethoxy)-phenyl)isoxazol-4-yl)methanone, (5-methyl-3-(3-(trifluoromethoxy)phenyl)isoxazol-4-yl)(4-(3-trifluoromethyl)phenyl)piperazine-1-yl)methanone, (4-(4-hydroxyphenyl)piperazine-1-yl)-(5-methyl-3-(3-(trifluoromethoxy)phenyl)isoxazol-4-yl)methanone, (4-(2-hydroxyphenyl)-piperazine-1-yl)(5-methyl-3-(3-(trifluoromethoxy)phenyl)isoxazol-4-yl)methanone, (4-(4-fluorophenyl)piperazine-1-yl)(5-methyl-3-(3-(trifluoromethoxy)phenyl)isoxazol-4-yl)-methanone, (5-amino-3-(2-chlorophenyl)isoxazol-4-yl)(4-(2-fluorophenyl)piperazine-1-yl)-methanone, (5-amino-3-(2-chlorophenyl)isoxazol-4-yl)(4-(3,4-dichlorophenyl)piperazine-1-yl)methanone, (5-amino-3-(2-chlorophenyl)isoxazol-4-yl)(4-(3-methoxyphenyl)piperazine-1-yl)methanone, (5-amino-3-(2-chlorophenyl)isoxazol-4-yl)(4-(2-methoxyphenyl)piperazine-1-yl)methanone, (5-amino-3-(2-chlorophenyl)isoxazol-4-yl)(4-(3-(trifluoromethyl)phenyl)-piperazine-1-yl)methanone, (5-amino-3-(2-chlorophenyl)isoxazol-4-yl)(4-(4-hydroxyphenyl)-piperazine-1-yl)methanone, (5-amino-3-(2-chlorophenyl)isoxazol-4-yl)(4-(2-hydroxyphenyl)-piperazine-1-yl)methanone, (5-amino-3-(2-chlorophenyl)isoxazol-4-yl)(4-(4-fluorophenyl)-piperazine-1-yl)methanone, (5-amino-3-(3-fluorophenyl)isoxazol-4-yl)(4-(2-fluorophenyl)-piperazine-1-yl)methanone, (5-amino-3-(3-fluorophenyl)isoxazol-4-yl)(4-(3,4-dichloro-phenyl)piperazine-1-yl)methanone, (5-amino-3-(3-fluorophenyl)isoxazol-4-yl)(4-(3-methoxy-phenyl)piperazine-1-yl)methanone, (5-amino-3-(3-fluorophenyl)isoxazol-4-yl)(4-(2-methoxy-phenyl)piperazine-1-yl)methanone, (5-amino-3-(3-fluorophenyl)isoxazol-4-yl)(4-(3-(trifluoro-methyl)phenyl)piperazine-1-yl)methanone, (5-amino-3-(3-fluorophenyl)isoxazol-4-yl)(4-(4-hydroxyphenyl)piperazine-1-yl)methanone, (5-amino-3-(3-fluorophenyl)isoxazol-4-yl)(4-(2-hydroxyphenyl)piperazine-1-yl)methanone, (5-amino-3-(3-fluorophenyl)isoxazol-4-yl)(4-(4-fluorophenyl)piperazine-1-yl)methanone, (5-amino-3-(2-fluorophenyl)isoxazol-4-yl)(4-(2-fluorophenyl)piperazine-1-yl)methanone, (5-amino-3-(2-fluorophenyl)isoxazol-4-yl)(4-(3,4-dichlorophenyl)piperazine-1-yl)methanone, (5-amino-3-(2-fluorophenyl)isoxazol-4-yl)(4-(3-methoxyphenyl)piperazine-1-yl)methanone, (5-amino-3-(2-fluorophenyl)isoxazol-4-yl)(4-(2-methoxyphenyl)piperazine-1-yl)methanone, (5-amino-3-(2-fluorophenyl)isoxazol-4-yl)(4-(3-(trifluoromethyl)phenyl)piperazine-1-yl)methanone, (5-amino-3-(2-fluorophenyl)-isoxazol-4-yl)(4-(4-hydroxyphenyl)piperazine-1-yl)methanone, (5-amino-3-(2-fluorophenyl)-isoxazol-4-yl)(4-(2-hydroxyphenyl)piperazine-1-yl)methanone, (5-amino-3-(2-fluorophenyl)-isoxazol-4-yl)(4-(4-fluorophenyl)piperazine-1-yl)methanone, (5-amino-3-(2-(trifluoro-methoxy)phenyl)-isoxazol-4-yl)(4-(2-fluorophenyl)piperazine-1-yl)methanone, (5-amino-3-(2-(trifluoro-methoxy)phenyl)isoxazol-4-yl)(3,4-dichlorophenyl)piperazine-1-yl)methanone, (5-amino-3-(2-(trifluoromethoxy)phenyl)isoxazol-4-yl)(4-(3-methoxyphenyl)piperazine-1-yl)methanone, (5-amino-3-(2-(trifluoromethoxy)phenyl)isoxazol-4-yl)(4-(2-methoxyphenyl)-piperazine-1-yl)methanone, (5-amino-3-(2-(trifluoromethoxy)phenyl)isoxazol-4-yl)(4-(3-(trifluoromethyl)phenyl)piperazine-1-yl)methanone, (5-amino-3-(2-(trifluoromethoxy)-phenyl)isoxazol-4-yl)(4-(4-hydroxyphenyl)piperazine-1-yl)methanone, (5-amino-3-(2-(trifluoromethoxy)phenyl)isoxazol-4-yl)(4-(2-hydroxyphenyl)piperazine-1-yl)methanone, (5-amino-3-(2-(trifluoromethoxy)phenyl)isoxazol-4-yl)(4-(4-fluorophenyl)piperazine-1-yl)-methanone, (5-amino-3-(2-(trifluoromethyl)phenyl)isoxazol-4-yl)(4-(2-fluorophenyl)-piperazine-1-yl)methanone, (5-amino-3-(2-(trifluoromethyl)phenyl)isoxazol-4-yl)(4-(3,4-dichlorophenyl)piperazine-1-yl)methanone, (5-amino-3-(2-trifluoromethyl)phenyl)isoxazol-4-yl)(4-(3-methoxyphenyl)piperazine-1-yl)methanone, (5-amino-3-(2-(trifluoromethyl)-phenyl)isoxazol-4-yl)(4-(2-methoxyphenyl)piperazine-1-yl)methanone, 5-amino-3-(2-(trifluoromethyl)phenyl)isoxazol-4-yl)(4-(3-(trifluoromethyl)phenyl)piperazine-1-yl)-methanone, (5-amino-3-(2-(trifluoromethyl)phenyl)isoxazol-4-yl)(4-(4-hydroxyphenyl)-piperazine-1-yl)methanone, (5-amino-3-(2-(trifluoromethyl)phenyl)isoxazol-4-yl)(4-(2-hydroxyphenyl)piperazine-1-yl)methanone, (5-amino-3-(2-(trifluoromethyl)phenyl)isoxazol-4-yl)(4-(4-fluorophenyl)piperazine-1-yl)methanone, (5-amino-3-(4-(trifluoromethoxy)-phenyl)isoxazol-4-yl)(4-(2-fluorophenyl)piperazine-1-yl)methanone, (5-amino-3-(4-(trifluoromethoxy)phenyl)isoxazol-4-yl)(4-(3,4-dichlorophenyl)piperazine-1-yl)methanone, (5-amino-3-(4-(trifluoromethoxy)phenyl)isoxazol-4-yl)(4-(3-methoxyphenyl)piperazine-1-yl)methanone, (5-amino-3-(4-(trifluoromethoxy)phenyl)isoxazol-4-yl)(4-(2-methoxyphenyl)-piperazine-1-yl)methanone, (5-amino-3-(4-(trifluoromethoxy)phenyl)isoxazol-4-yl)(4-(3-(trifluoromethylphenyl)piperazine-1-yl)methanone, (5-amino-3-(4-(trifluoromethoxy)-phenyl)isoxazol-4-yl)(4-(4-hydroxyphenyl)piperazine-1-yl)methanone, (5-amino-3-(4-(trifluoromethoxy)phenyl)isoxazol-4-yl)(4-(2-hydroxyphenyl)piperazine-1-yl)methanone, (5-amino-3-(4-(trifluoromethoxy)phenyl)isoxazol-4-yl)(4-(4-fluorophenyl)piperazine-1-yl)-methanone, (5-amino-3-(3-(trifluoromethyl)phenyl)isoxazol-4-yl)(4-(2-fluorophenyl)-piperazine-1-yl)methanone, (5-amino-3-(3-(trifluoromethyl)phenyl)isoxazol-4-yl)(4-(3,4-dichlorophenyl)piperazine-1-yl)methanone, (5-amino-3-(3-(trifluoromethyl)phenyl)isoxazol-4-yl)(4-(3-methoxyphenyl)piperazine-1-yl)methanone, (5-amino-3-(3-(trifluoromethyl)-phenyl)isoxazol-4-yl)(4-(2-methoxyphenyl)piperazine-1-yl)methanone, (5-amino-3-(3-(trifluoromethyl)phenyl)isoxazol-4-yl)(4-(3-(trifluoromethyl)phenyl)piperazine-1-yl)-methanone, (5-amino-3-(3-(trifluoromethyl)phenyl)isoxazol-4-yl)(4-(4-hydroxyphenyl)-piperazine-1-yl)methanone, (5-amino-3-(3-(trifluoromethyl)phenyl)

isoxazol-4-yl)(4-(2-hydroxyphenyl)piperazine-1-yl)methanone, (5-amino-3-(3-(trifluoromethyl)phenyl)isoxazol-4-yl)(4-(4-fluorophenyl)piperazine-1-yl)methanone, (5-amino-3-(3-(trifluoromethoxy)-phenyl)isoxazol-4-yl)(4-(2-fluorophenyl)piperazine-1-yl)methanone, (5-amino-3-(3-(trifluoromethoxy)phenyl)isoxazol-4-yl)(4-(3,4-dichlorophenyl)piperazine-1-yl)methanone, (5-amino-3-(3-(trifluoromethoxy)phenyl)isoxazol-4-yl)(4-(3-methoxyphenyl)piperazine-1-yl)-methanone, (5-amino-3-(3-(trifluoromethoxy)phenyl)isoxazol-4-yl)(4-(2-methoxyphenyl)-piperazine-1-yl)methanone, (5-amino-3-(3-(trifluoromethoxy)phenyl)isoxazol-4-yl)(4-(3-trifluoromethyl)phenyl)piperazine-1-yl)methanone, (5-amino-3-(3-(trifluoromethoxy)phenyl)-isoxazol-4-yl)(4-(4-hydroxyphenyl)piperazine-1-yl)methanone, (5-amino-3-(3-(trifluoro-methoxy)phenyl)isoxazol-4-yl)(4-(2-hydroxyphenyl)piperazine-1-yl)methanone, (5-amino-3-(3-(trifluoromethoxy)phenyl)isoxazol-4-yl)(4-(4-fluorophenyl)piperazine-1-yl)methanone, ethyl-1-(5-amino-3-(2-chlorophenyl)isoxazol-4-carbonyl)piperidine-4-carboxylate, methyl-1-(5-amino-3-(2-fluorophenyl)isoxazol-4-carbonyl)piperidine-4-carboxylate, ethyl-1-(5-amino-3-(2-trifluoromethoxy)phenyl)isoxazol-4-carbonyl)piperidine-4-carboxylate, or ethyl-1-(5-amino-3-(2-(trifluoromethyl)phenyl)isoxazol-4-carbonyl)piperidine-4-carboxylate.

2. A compound or a pharmaceutically acceptable salt, hydrate, solvate, or an acetate, formate or benzoate ester thereof, selected from among (4-(3-methoxyphenyl)-piperazine-1-yl)(5-methyl-3-(2-(trifluoromethyl)-phenyl)isoxazol-4-yl)methanone, (4-(2-methoxyphenyl)piperazine-1-yl)(5-methyl-3-(2-trifluoromethyl-phenyl)isoxazol-4-yl)-methanone, (3-(2-chlorophenyl)-5-methyl-isoxazol-4-yl)(4-(3-methoxyphenyl)piperazine-1-yl)methanone, (4-(3,4-dichlorophenyl)-piperazine-1-yl)(3-(3-fluorophenyl)-5-methyl-isoxazol-4-yl)methanone, (3-(3-fluorophenyl)-5-methylisoxazol-4-yl)(4-(3-methoxyphenyl)-piperazine-1-yl)methanone, (3-(3-fluorophenyl)-5-methylisoxazol-4-yl)(4-(2-hydroxy-phenyl)piperazine-1-yl)methanone, (4-(3,4-dichloro-phenyl)piperazine-1-yl)(3-(2-fluoro-phenyl)-5-methylisoxazol-4-yl)methanone, (3-(2-fluoro-phenyl)-5-methylisoxazol-4-yl)(4-(3-methoxyphenyl)piperazine-1-yl)methanone, (4-(3,4-dichlorophenyl)piperazine-1-yl)(5-methyl-3-(4-(trifluoromethoxy)phenyl)isoxazol-4-yl)-methanone, (4-(3,4-dichlorophenyl)-piperazine-1-yl)(5-methyl-3-(2-(trifluoromethoxy)-phenyl)isoxazol-4-yl)methanone, (3-(2-fluorophenyl)-5-methylisoxazol-4-yl)(4-(3-methoxy-phenyl)piperazine-1-yl)methanone, (4-(3-methoxyphenyl)piperazine-1-yl)(5-methyl-3-(3-(trifluoromethyl)phenyl)isoxazol-4-yl)methanone, (4-(2-hydroxyphenyl)piperazine-1-yl)(5-methyl-3-(3-(trifluoromethyl)-phenyl)isoxazol-4-yl)methanone, (4-(3,4-dichlorophenyl)-piperazine-1-yl)(5-methyl-3-(3-(trifluoromethoxy)phenyl)isoxazol-4-yl)methanone, (4-(3-methoxyphenyl)piperazine-1-yl)(5-methyl-3-(3-(trifluoromethoxy)phenyl)isoxazol-4-yl)-methanone, (5-amino-3-(2-chloro-phenyl)isoxazol-4-yl)(4-(3-methoxyphenyl)piperazine-1-yl)methanone, (5-amino-3-(2-chlorophenyl)isoxazol-4-yl)(4-(2-methoxyphenyl)piperazine-1-yl)methanone, (5-amino-3-(3-fluorophenyl)isoxazol-4-yl)(4-(3,4-dichlorophenyl)piperazine-1-yl)methanone, (5-amino-3-(3-fluorophenyl)isoxazol-4-yl)(4-(2-hydroxyphenyl)piperazine-1-yl)methanone, (5-amino-3-(2-fluorophenyl)isoxazol-4-yl)(4-(3,4-dichlorophenyl)-piperazine-1-yl)methanone, (5-amino-3-(2-fluorophenyl)isoxazol-4-yl)(4-(3-methoxy-phenyl)piperazine-1-yl)methanone, (5-amino-3-(2-(trifluoromethoxy)phenyl)isoxazol-4-yl)(3,4-dichlorophenyl)piperazine-1-yl)methanone, (5-amino-3-(2-(trifluoromethoxy)-phenyl)isoxazol-4-yl)(4-(3-methoxyphenyl)piperazine-1-yl)methanone, (5-amino-3-(2-(trifluoromethyl(phenyl)isoxazol-4-yl)(4-(3,4-dichlorophenyl)piperazine-1-yl)methanone, (5-amino-3-(2-trifluoromethyl)-phenyl)-isoxazol-4-yl)(4-(3-methoxyphenyl)piperazine-1-yl)-methanone, (5-amino-3-(3-(trifluoro-methyl)phenyl)isoxazol-4-yl)(4-(3,4-dichlorophenyl)-piperazine-1-yl)methanone, (5-amino-3-(3-(trifluoromethyl)phenyl)isoxazol-4-yl)(4-(3-methoxyphenyl)piperazine-1-yl)methanone, (5-amino-3-(3-(trifluoromethyl)phenyl)isoxazol-4-yl)(4-(2-hydroxyphenyl)piperazine-1-yl)-methanone, (5-amino-3-(3-(trifluoromethoxy)-phenyl)isoxazol-4-yl)(4-(3,4-dichlorophenyl)-piperazine-1-yl)methanone, (5-amino-3-(3-(trifluoromethoxy)phenyl)isoxazol-4-yl)(4-(3-methoxyphenyl)piperazine-1-yl)methanone, (5-amino-3-(3-(trifluoromethoxy)phenyl)-isoxazol-4-yl)(4-(2-hydroxyphenyl)piperazine-1-yl)-methanone, ethyl-1-(5-amino-3-(2-chlorophenyl)isoxazol-4-carbonyl)piperidine-4-carboxylate, or ethyl-1-(5-amino-3-(2-trifluoromethoxy)phenyl)isoxazol-4-carbonyl)-piperidine-4-carboxylate.

\* \* \* \* \*

UNITED STATES PATENT AND TRADEMARK OFFICE
CERTIFICATE OF CORRECTION

PATENT NO. : 9,132,126 B2
APPLICATION NO. : 13/979743
DATED : September 15, 2015
INVENTOR(S) : Dong Yeon Kim et al.

It is certified that error appears in the above-identified patent and that said Letters Patent is hereby corrected as shown below:

IN THE TITLE PAGES:

In Item (57) Abstract, at page 1, column II, line 44, please replace "phenyl-isoxazol" with —phenyl-isoxazole—.

IN THE SPECIFICATION:

At column 1, line 14, please replace "phenyl-isoxazol" with —phenyl-isoxazole—;
at column 3, line 32, please replace "phenyl-isoxazol" with —phenyl-isoxazole—;
at column 3, line 47, please replace "phenyl-isoxazol" with —phenyl-isoxazole—;
at column 4, line 67, please replace "phenyl-isoxazol" with —phenyl-isoxazole—;
at column 8, line 1, please replace "isoxazol compound" with —isoxazole compound—;
at column 9, line 56, please replace " 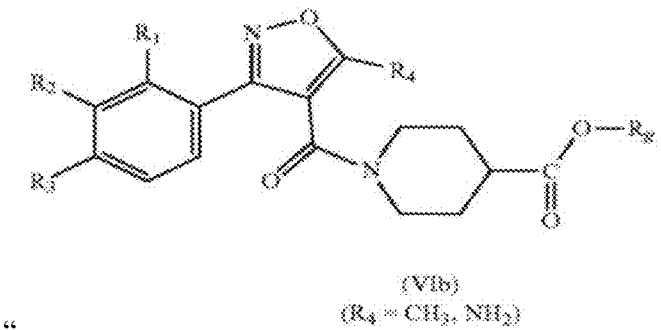 "

Signed and Sealed this
Fifteenth Day of March, 2016

Michelle K. Lee
*Director of the United States Patent and Trademark Office* with —

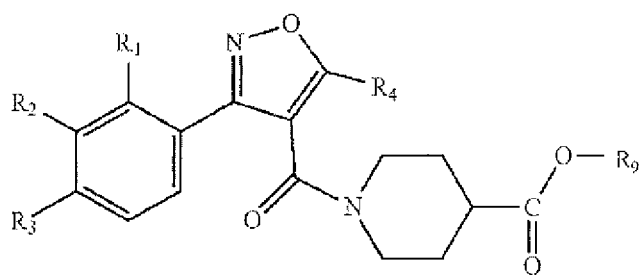

(VIb)
($R_4$ = $CH_3$, $NH_2$)

—;

at column 10, line 9, please replace "isoxazol compound" with —isoxazole compound—;

at column 10, line 10, please replace "R" with —$R_4$—;

at column 10, line 13, please replace "phenyl-isoxazol" with —phenyl-isoxazole—;

at column 10, line 15, please replace "phenyl-isoxazol" with —phenyl-isoxazole—;

at column 10, line 26, please replace "ethyllacetate" with —ethylacetate—; and at column 14, line 63, please replace "methyllacetoacetate" with —methylacetoacetate—.